United States Patent [19]

Sessler et al.

[11] Patent Number: 5,733,903
[45] Date of Patent: Mar. 31, 1998

[54] TREATMENT OF NEOPLASTIC TISSUE BY WATER-SOLUBLE TEXAPHYRINE METAL COMPLEXES

[75] Inventors: Jonathan L. Sessler; Gregory W. Hemmi; Tarak D. Mody, all of Austin, Tex.

[73] Assignee: Board of Regents, The University of Texas System, Austin, Tex.

[21] Appl. No.: 679,162

[22] Filed: Jul. 10, 1996

Related U.S. Application Data

[60] Continuation of Ser. No. 98,514, Jul. 28, 1993, Pat. No. 5,569,759, which is a division of Ser. No. 822,964, Jan. 21, 1992, Pat. No. 5,252,720.

[51] Int. Cl.$^6$ .................. A61K 31/715; C07D 487/22
[52] U.S. Cl. .................. 514/185; 540/465; 540/472; 540/145; 534/11; 534/15; 534/16
[58] Field of Search .................. 534/11, 15, 16; 514/185; 540/465, 472, 145

[56] References Cited

U.S. PATENT DOCUMENTS

| | | | |
|---|---|---|---|
| 3,920,692 | 11/1975 | Wiersdorff et al. | 260/314 |
| 5,250,668 | 10/1993 | Morgan et al. | 540/145 |
| 5,252,720 | 10/1993 | Sessler et al. | 534/11 |
| 5,257,970 | 11/1993 | Dougherty | 604/20 |
| 5,457,183 | 10/1995 | Sessler et al. | 534/11 |
| 5,559,207 | 9/1996 | Sessler et al. | 530/300 |

FOREIGN PATENT DOCUMENTS

| | | |
|---|---|---|
| 94/29316 | 12/1994 | WIPO . |
| 95/21845 | 8/1995 | WIPO . |
| 96/09315 | 3/1996 | WIPO . |

OTHER PUBLICATIONS

Maiya et al. J. Phy.Chem. 1989, 93, p. 8111–8115.

Sessle et al., Topics in Current Chemistry, vol. 161, p. 205.

Sessler and Burrell, "Expanded Porphyrins," *Topics in Current Chemistry*, 161:180–273, 1991.

Sessler *et al.*, "Synthesis and Structural Characterization of Lanthanide(III) Texaphyrins," *Inorgnaic chemistry*, 32(14):3175–3187, 1993.

Sessler, Jonathan L., "Texas–Sized Molecule," *Discovery*, 13(1):44–49, 1993.

Sessler et al., "Photodynamic Inactivation of Enveloped Viruses Using Sapphyrin, a 22 II–Electron Expanded Porphyrin: Possible Approaches to Prophylactic Blood Purificatiion Protocols," *SPIE Photodynamic Therapy: Mechanisms II.* 1203L233–245, 1990.

Maiya *et al.*, "Ground–and Excited–State Spectral and Redox Properties of Cadmium(II) Texaphryrin," *Journal of Physical Chemistry*, 93(24) :8111–8115, 1989.

Sessler et al., "Texaphyrins: Synthesis and Applications," *Accounts of Chemical Research*, 27(2) :43–50, 1994.

Leff, "Texas 'Son–of–Porphyrin' Molecule Lassos Europium to Kill Drug Resistance Gene," *BioWorld Today*, 5(156):1, 1994.

Young et al., "Preclinical Evaluation of Gadolinium (III) Texaphyrin Complex. A New Paramagnetic Contrast Agent for Magnetic Resonance Imaging," *Investigative Radiology*, 29(3) :330–338, 1994.

Furuta et al., "Enhanced Transport of Nucleosides and Nucleoside Analogues with Complementary Base–Pairing Agents."*Journal of the American Chemical Society*, 113:4706–4707, 1991.

Sessler et al., "Anion Binding: A New Direction In Porphyrin–Related Research," *Pure & Applied Chem.*, 65(3) :393–398, 1993.

Sessler et al., "Synthesis and Binding Properties of Monomeric and Dimeric Guanine and Cytosine Amine Derivatives," *J. Org. Chem.*, 1992, 57:818–826.

T.D. Mody et al., "Lutetium (III) Texaphyrin: A Novel Photodynamic Therapy Agent," Abstract, *22nd Annual American Society for Photobiology*, Scottsdale, AZ, Jun. 25–29, 1994.

Sessler et al., "Gadolinium (III) Texaphyrin: A Novel MRI Contrast Agent," *Journal of the American Chemical Society*, 115(22):10368–10369, 1993.

Iverson et al., "Interactions Between Expanded Porphyrins and Nucleic Acids," *Pure Applied Chemistry*, 66(4):845–850, 1994.

Magda et al., "Site–Specific Hydrolysis of RNA by Europium (III) Texaphyrin Conjugated to a Synthetic Oligodeoxyribonucleotide," *Journal of the American Chemical Society*, 116(16):7439–7440, 1994.

Koenig et al., "PDT of Tumor–Bearing Mice Using Liposome Delivered Texaphyrins," International Conference, Milan, Italy, biosis citation only, Jun. 24–27, 1992.

Mastruzzo et al., "Targeted Photochemical Modification of HIV–Derived Oligoribonucleotides by Antisense Oligodeoxynucleotides Linked to Porphyrins," *Photochemistry and Photobiology*, vol. 60, No. 4, pp. 316–322, 1994.

Magda et al., "Sequence–Specific Photocleavage of DNA by an Expanded Porphyrin with Irradiation Above 700 nm," *J. Am. Chem. Soc.*, 117:3629–3630, 1995.

Sessler et al., "Expanded Porphyrins. Receptors for Cationic, Anionic, and Neutral Substrates," in Transition Metals in Supramolecular Chemistry, L. Fabbrizzi and A. Poggi, Editors, NATO ASI Series, Kluwer, Amsterdam, pp. 391–408, 1994.

PCT/US94/11491 International Search Report mailed Feb. 23, 1995.

PCT/US94/06284 International Search Report mailed Dec. 6, 1994.

PCT/US93/09994 International Search Report mailed Feb. 22, 1994.

PCT/US93/09994 International Search Report mailed Feb. 3, 1994.

(List continued on next page.)

*Primary Examiner*—Mukund J. Shah
*Assistant Examiner*—Pavanaram K. Sripada
*Attorney, Agent, or Firm*—Jacqueline S. Larson

[57] ABSTRACT

The present invention relates to the use of water-soluble texaphyrin-diamagnetic metal complexes retaining lipophilicity as photosensitizers in the treatment of benign and malignant neoplastic tissue.

19 Claims, 25 Drawing Sheets

OTHER PUBLICATIONS

Ehrenberg et al., "Spectroscopy, Photokinetics and Cellular Effect of FarRed and Near Infrared Absorbing Photosensitizers," *Proc. SPIE–Int. Soc. Opt. Eng 1992, 1645 (Proc. Opt. Methods Tumor Treat. dect.: Mech. Tech. Photodyn. Ther. . . . , 259–263, 1992.*

Thaller et al., "Potential Use of Radiolabelled Porphyrins for Tumor Scanning," *Porphyrin Photosensitization*, Kessel and Dougherty, Eds., Plenum Press, New York and London, Publisher, pp. 265–278, 1981.

Brown and Truscott, "New Light on Cancer Therapy," *Chemistry in Britain*, 955–958, 1993.

Ehrenberg et al., "The Binding and Photosensitization Effects of Tetrabenzoporphyrins and Texaphyrin in Bacterial Cells," *Lasers in Medical Science*, 8:197–203, 1993.

Morgan and Skalkos, "Second Generation Sensitizers: Where are We and Where Should We Be Going?" *Proc. SPIE Int. Soc. Opt. Eng. Ser.*, 6:87–106, 1990.

Horstman, "Study to examine skin cancer drug activated by light," *Stanford University Campus Report*, Mar. 1996.

Biolo, et al., "Photodynamic Therapy of B16 Pigmented Melanoma With Liposome–Delivered Si(IV)–Naphthalocyanine," *Photochemistry and Photobiology*, vol. 59, No. 3, pp. 362–265, 1994.

Haylett, et al., "Pharmacokinetic and therapeutic outcome in melanoma cells, of the administration of symmetric and asymmetric cationic photosensitizers," *Cancer Letters* 88, pp. 191–199, 1995.

Leunig, et al., "Tumour localisation kinetics of photofrin and three synthetic porphyrioids in an amelanotic melanoma of the hamster," *Br. J. Cancer*, 68, pp. 225–234, 1993.

Nelson, et al., "Photodynamic Therapy of Human Malignant Melanoma Xenografts in Athymic Nude Mice," *Jurnal of the National Cancer Institute*, vol. 80, No. 1, Mar. 2, 1988.

Sealy, et al., "Photosensitization of Melanin: An Electron Spin Resonance Study of Sensitized Radical Production and Oxygen Consumption," *Photochemistry and Photobiology*, vol. 40, No. 4, pp. 453–459, 1984.

Dialog Search, 1996.

PCT/US90/01208 International Search Report mailed Aug. 2, 1990.

PCT/US95/12312 International Search Report mailed Feb. 9, 1996.

König et al., "PDT of Tumor–Bearing Mice Using Liposome Delivered Texaphyrins", International Conference on Photodynamic Therapy and Medical Laser Applications, Milan, Italy, Photodynamic Therapy and Biomedical Lasers, ed. Spinelli et al., Elsevier Science Publishers B.V., pp. 802–805, 1992.

König et al., "Photodynamic Activity of Liposome–Delivered Cd–Texaphyrin Using Tumor–Bearing Nude Mice", *Lasers in Surgery and Medicine* 13:522–527, 1993.

Pharmacyclics' Press Release, "Pharmacyclics Expands Photodynamic Therapy Trial to Stanford," Mar. 28, 1996.

Fieser & Fieser, "Reagents for Organic Synthesis," John Wiley & Sons, Inc., vol. I, eratta sheet and p. 215, 1967.

PCT/US96/08262 International Search Report mailed Sep. 10, 1996.

Dialog Search, 1995.

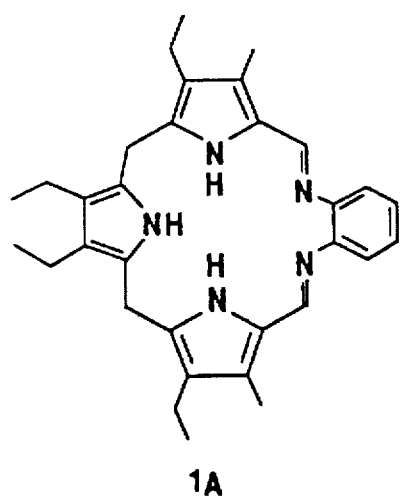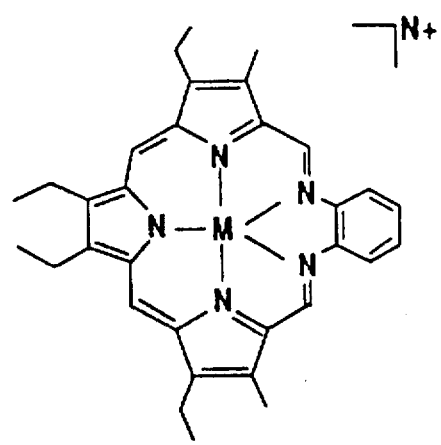
1B  M = H, n = 0
1C  M = Cd, n = 1
FIG. 1A
FIG. 1B

5A  R = CH₃

5B  M = H,  R = CH₃, n = 2
5C  M = Gd, R = CH₃, n = 2
5D  M = Eu, R = CH₃, n = 2
5E  M = Sm, R = CH₃, n = 2

19G

Gd(OAc)₃·4H₂O
Triethylamine
Air
MeOH

19H  M = Gd, N=2

5,733,903

TREATMENT OF NEOPLASTIC TISSUE BY WATER-SOLUBLE TEXAPHYRINE METAL COMPLEXES

CROSS REFERENCE TO RELATED APPLICATIONS

This application is a continuation of application Ser. No. 08/098,514, filed Jul. 28, 1993, now U.S. Pat. No. 5,569,759, which is a division of application Ser. No. 07/822,964, filed Jan. 21, 1992, now U.S. Pat. No. 5,252,720; and benefit of the filing date of said earlier filed applications are claimed under 35 U.S.C. §120.

The government has certain rights in the present invention pursuant to National Institutes of Health contract AI28845.

BACKGROUND OF THE INVENTION

The porphyrins and related tetrapyrrole macrocycles are among the most versatile of tetradentate ligands[1]. Attempts to stabilize higher coordination geometries with larger porphyrin-like aromatic macrocycles have met with little success.[2-13] Only the uranyl complex of "superphthalocyanine" has been isolated and characterized structurally,[2] although several other large porphyrin-like aromatic macrocycles, including the "sapphyrins",[3,6] "oxosapphyrins",[6,7] "platyrins",[8] "pentaphyrin",[9] and "[26] porphyrin",[10] have been prepared in their metal free forms. Large, or "expanded" porphyrin-like systems are of interest for several reasons: They could serve as aromatic analogues of the better studied porphyrins[2-10] or serve as biomimetic models for these or other naturally occurring pyrrole-containing systems.[36,13a] In addition, large pyrrole containing systems offer possibilities as novel metal binding macrocycles.[2,4,5,13b,35,14] For instance, suitably designed systems could act as versatile ligands capable of binding larger metal cations and/or stabilizing higher coordination geometries[2] than those routinely accommodated within the normally. tetradentate ca. 2.0 Å radius porphyrin core.[21] The resulting complexes could have important application in the area of heavy metal chelation therapy, serve as contrast agents for magnetic resonance imaging (MRI) applications, act as vehicles for radioimmunological labeling work, or serve as new systems for extending the range and scope of coordination chemistry.[14,39] In addition, the free-base (metal-free) and/or diamagnetic metal-containing materials could serve as useful photosensitizers for photodynamic therapeutic applications. In recent years a number of pentadentate polypyrrolic aromatic systems, including the "sapphyrins",[3,6] "oxosapphyrins",[7] "smaragdyrins",[3,6] "platyrins",[8] and "pentaphyrin"[9] have been prepared and studied as their metal-free forms. For the most part, however, little or no information is available for the corresponding metallated forms. Prior to this invention the uranyl complex of "superphthalocyanine" was the only metal-containing pentapyrrolic system which has been prepared and characterized structurally.[2] The "superphthalocyanine" system is not capable of existence in either its free-base or other metal-containing forms.[2] Thus, prior to the present invention, no versatile, structurally characterized, pentadentate aromatic ligands were available,[13b] although a number of nonaromatic pyridine-derived pentadentate systems had previously been reported.[37,38]

Gadolinium(III) complexes derived from strongly binding anionic ligands, such as diethylenetriamine pentaacetic acid (DTPA),[40-42] 1,4,7,10-tetraazacyclododecane N,N',N'',N'''-tetraacetic acid (DOTA),[40,43,44] and 1,10-diaza-4,7,13,16-tetraoxacyclooctadecane-N,N'-diacetic acid (dacda),[40,45] are among the most promising of the paramagnetic contrast agents currently being developed for use in magnetic resonance imaging (MRI)[40] The complex, [Gd.DTPA]$^-$, is now being used clinically in the United States in certain enhanced tumor detection and other imaging protocols.[40] Nonetheless, the synthesis of other gadolinium(III) complexes remains of interest since such systems might have greater kinetic stability, superior relaxivity, or better biodistribution properties than this or other carboxylate-based contrast agents. The water-soluble porphyrin derivatives, such as tetrakis(4-sulfonatophenyl)porphyrin (TPPS) cannot accommodate completely the large gadolinium(III) cation $^{47}$ within the relatively small porphyrin binding core (r≅2.0 Å$^{48}$), and, as a consequence, gadolinium porphyrin complexes are invariably hydrolytically unstable.[33,34,46,49,50] Larger porphyrin-like ligands may offer a means of circumventing this problem.[51-59]

A promising new modality for use in the control and treatment of tumors is photodynamic therapy (PDT).[60-64] This technique uses of a photosensitizing dye, which localizes at, or near, the tumor site, and when irradiated in the presence of oxygen serves to produce cytotoxic materials, such as singlet oxygen ($O_2(^1\Delta_g)$), from benign precursors (e.g. ($O_2(^3\Sigma_g^-)$). Diamagnetic porphyrins and their derivatives are the dyes of choice for PDT. It has been known for decades that porphyrins, such as hematoporphyrin, localize selectively in rapidly growing tissues including sarcomas and carcinomas. The hematoporphyrin derivative (HPD),[61,64,66,80] is an incompletely characterized mixture of monomeric and oligomeric porphyrins.[81-86] The oligomeric species, which are believed to have the best tumor-localizing ability,[82,85] are marketed under the trade name Photofrin II® (PII) and are currently undergoing phase III clinical trials for obstructed endobronchial tumors and superficial bladder tumors. The mechanism of action is thought to be the photoproduction of singlet oxygen ($O_2(^1\Delta_g)$), although involvement of superoxide anion or hydroxyl and/or porphyrin-based radicals cannot be entirely ruled out.[87-92] Promising as HPD is, it and other available photosensitizers (e.g., the phthalocyanines and naphthalocyanines) suffer from serious disadvantages.

While porphyrin derivatives have high triplet yields and long triplet lifetimes (and consequently transfer excitation energy efficiently to triplet oxygen),[101b,g] their absorption in the Q-band region parallels that of heme-containing tissues. Phthalocyanines and naphthalocyanines absorb in a more convenient spectral range but have significantly lower triplet yields;[102] moreover, they tend to be quite insoluble in polar protic solvents, and are difficult to functionalize. Thus the development of more effective photochemotherapeutic agents requires the synthesis of compounds which absorb in the spectral region where living tissues are relatively transparent (i.e., 770-1000 nm),[99d] have high triplet quantum yields, and are minimally toxic. The present inventors have recently reported[103] (see Example 1) the synthesis of a new class of aromatic porphyrin-like macrocycles, the tripyrroledimethine-derived "texaphyrins", which absorb strongly in the tissue-transparent 730-770 nm range. The photophysical properties of metallotexaphyrins parallel those of the corresponding metalloporphyrins and the diamagnetic complexes sensitize the production of $^1O_2$ in high quantum yield.

Acquired immunodeficiency syndrome (AIDS) is among the most serious public health problems facing our nation today. AIDS, first reported in 1981 as occurring among male homosexuals,[60] is a fatal human disease which has now reached pandemic proportions. At present, sexual relations and needle-sharing are the dominant mechanisms for the spread of AIDS.[60] Since the testing of blood supplies began, the percentage of AIDS infections due to blood transfusions has dropped considerably.[60,104,107] However, an absolutely fail-proof means must be developed to insure that all stored blood samples are free of the AIDS virus (and ideally all other blood-borne pathogens). Serologic tests for HIV-1 are insufficient to detect all infected blood samples, in particular, those derived from donors who have contracted the disease but not yet produced detectable antibodies.[104-107]

Any blood purification procedure used to remove AIDS virus or other blood-borne pathogens should operate without introducing undesirable toxins, damaging normal blood components, or inducing the formation of harmful metabolites. This precludes the use of common antiviral systems such as those based on heating, UV irradiation, or purely chemical means. A promising approach is the photodynamic one alluded to above. Here, preliminary studies, carried out by researchers at the Baylor Research Foundation, Dr. Matthews and his team,[93-96] and others,[97,98] have served to show that HPD and PII, in far lower dosages than are required for tumor treatment, act as efficient photosensitizers for the photo-deactivation of cell-free HIV-1, herpes simplex (HSV), hepatitis and other enveloped viruses. The success of this procedure derives from the fact that these dyes localize selectively at or near the morphologically characteristic, and physiologically essential, viral membrane ("envelope") and catalyze the formation of singlet oxygen upon photoirradiation. The singlet oxygen destroys the essential membrane envelope. This kills the virus and eliminates infectivity. Photodynamic blood purification procedures, therefore, rely on the use of photosensitizers which localize selectively at viral membranes, just as more classic tumor treatments require dyes that are absorbed or retained preferentially at tumor sites. Simple enveloped DNA viruses like HSV-1 are good models for testing putative photosensitizers for potential use in killing the far more hazardous HIV-1 retrovirus. This correspondence holds only as far as freely circulating (as opposed to intracellular) viruses are concerned. Complete prophylactic removal of HIV-1 from blood products will require the destructive removal of the virus from within monocytes and T lymphocytes.[108]

This "first generation" of dyes suffers from a number of serious deficiencies which may militate against their eventual use in biomedical applications. Each of these deficiencies has important clinical consequences. Since HPD and PII do not contain a single chemically well-defined constituent, coupled with the fact that the active components have yet to be identified with certainty,[82-86] means that the effective concentrations vary from preparation to preparation. Thus the dosage, and the light fluence, cannot be optimized and predetermined for any particular application. Since they are not metabolized rapidly, significant quantities of these dyes remain in stored blood units after prophylactic photoinduced HIV-1 removal and remain in patients' bodies long after photodynamic tumor treatment. The latter retention problem, in particular, is known to be serious; HPD and PII localize in the skin and induce photosensitivity in patients for weeks after administration.[64,109] Since the longest wavelength absorption maximum for these dyes falls at 630 nm, most of the incipient energy used in photo-treatment is dispersed or attenuated before reaching the center of a deep-seated tumor and as a result, little of the initial light is available for singlet oxygen production and therapy.[110-112] A study using a mouse model with a 3 mm tumor implanted beneath the skin indicated that as much as 90% of the energy is lost by the base of the tumor.[110] More effective treatment of deep-seated or large tumors may be possible if photosensitizers could be developed which absorb in the >700 nm region, provided, of course, they retain the desirable features of HPD and PII (e.g. selective localization in target tissues and low dark toxicity). One aspect of the present invention involves development of such improved photosensitizers for use in photodynamic tumor treatment and blood purification protocols.

The following list summarizes features which would be desirable in biomedical photosensitizers:

1. Easily available
2. Low intrinsic toxicity
3. Long wavelength absorption
4. Efficient photosensitizer for singlet oxygen production
5. Fair solubility in water
6. Selective up-take in tumor tissue and/or
7. Showing high affinity for enveloped viruses
8. Quick degradation and/or elimination after use
9. Chemically pure and stable
10. Easily subject to synthetic modification In recent years, considerable effort has been devoted to the synthesis and study of new photosensitizers which might meet these desiderata. Although a few of these have consisted of classic dyes such as those of the rhodamine and cyanine classes,[113-115] many have been porphyrin derivatives with extended $\pi$ networks.[116-126] Included in this latter category are the purpurins and verdins[116] of Morgan and other chlorophyll-like species,[117-119] the benz-fused porphyrins of Dolphin et al.,[120] and the sulfonated phthalocyanines and napthophthalocyanines studied by Ben-Hur,[121] Rodgers, 122 and others.[123-127] Of these only the napthophthalocyanines absorb efficiently in the most desirable >700 nm spectral region. These particular dyes are difficult to prepare in a chemically pure, water soluble form and are relatively inefficient photosensitizers for singlet oxygen production, perhaps even acting photodynamically via other oxygen derived toxins (e.g. superoxide). Thus a search continues for yet a "third generation" of photosensitizers which might better meet the ten critical criteria listed above.

It is an important aspect of the present invention that an improved "third generation" of photosensitizers is obtained using large, pyrrole-containing "expanded porphyrins". These systems, being completely synthetic, can be tuned so as to incorporate any desired properties. In marked contrast to the literature of the porphyrins, and related tetrapyrrolic systems (e.g. phthalocyanines, chlorins, etc.), there are only a few reports of larger pyrrole-containing systems, and only a few of these meet the criterion of aromaticity deemed essential for long-wavelength absorption and singlet oxygen photosensitization.[128] In addition to the present inventors' studies of texaphyrin $1_B$,[129] (see FIGS. 1 and 2), and "sapphyrin", first produced by the groups of Woodward[3] and Johnson[6], there appear to be only three large porphyrin-like systems which might have utility as photosensitizers. These are the "platyrins" of LeGoff[8], the stretched porphycenes of Vogel [131a] and the vinylogous porphyrins of Franck.[130] The present studies indicate that an expanded porphyrin approach to photodynamic therapy is promising. The porphycenes,[131b, 131c] a novel class of "contracted porphyrins" also show promise as potential photosensitizers.[132]

The present invention involves a major breakthrough in the area of ligand design and synthesis. It involves the synthesis of the first rationally designed aromatic pentadentate macrocyclic ligand, the tripyrroledimethine-derived "expanded porphyrin" $1_B$.[129] This compound, to which the trivial name "texaphyrin" has been assigned, is capable of existing in both its free-base form and of supporting the formation of hydrolytically stable 1:1 complexes with a variety of metal cations, such as $Cd^{2+}$, $Hg^{2+}$, $In^{3+}$, $Y^{3+}$, $Nd^{3+}$, $Eu^{3+}$, $Sm^{3+}$, $La^{3+}$, $Lu^{3+}$, $Gd^{3+}$, and other cations of the lanthanide series that are too large to be accommodated in a stable fashion within the 20% smaller tetradentate binding core of the well-studied porphyrins. In addition, since the free-base form of $1_B$ is a monoanionic ligand, the texaphyrin complexes formed from divalent and trivalent metal cations remain positively charged at neutral pH. As a result, many of these complexes are more water soluble than the analogous porphyrin complexes.

To date, two X-ray crystal structures of two different $Cd^{2+}$ adducts have been obtained, one of the coordinatively saturated, pentagonal bipyramidal bispyridine complex;[129a] the other of a coordinatively unsaturated pentagonal pyramidal benzimidazole complex.[129b] Both confirm the planar pentadentate structure of this new ligand system and support the assignment of this prototypical "expanded porphyrin" as aromatic.

Further support for the aromatic formulation comes from the optical properties of $1_B$ and $1_C$. The lowest energy Q-type band of the structurally characterized bispyridine cadmium(II) adduct of complex $1_C$ at 767 nm ($\epsilon=51,900$) in $CHCl_3$ is 10-fold more intense and red shifted by almost 200 nm as compared to that of a typical reference cadmium(II) porphyrin. Compound $1_B$ and both its zinc(II) and cadmium (II) complexes are very effective photosensitizers for singlet oxygen, giving quantum yields for $^1O_2$ formation of between 60 and 70% when irradiated at 354 nm in air-saturated methanol.[129c] Related congeneric texaphyrin systems bearing substituents on the tripyrrole and/or phenyl portions and incorporating La(III) and/or LU(III) metal centers, have been found to produce $^1O_2$ in quantum yields exceeding 70% when irradiated under similar conditions. Thus, it is this remarkable combination of light absorbing and $^1O_2$ photo-sensitizing properties which make these systems ideal candidates for use in photodynamic therapy and blood purification protocols.

SUMMARY OF THE INVENTION

The texaphyrin derivatives described in this continuation-in-part application are extensions of the structure $29_D$ in FIG. 27 of the parent application Ser. No. 771,393. By texaphyrin, we mean a compound with the central ring system depicted in structure 1A.

The present invention involves hydroxyl derivatives of texaphyrin, a novel tripyrrole dimethine-derived "expanded porphyrin", the synthesis of such compounds and their uses. The desirable properties of hydroxylated derivatives of texaphyrin are:

1) appreciable solubility, particularly in aqueous media;
2) biolocalization in desired target tissue;
3) the ability to attach to solid matrices;
4) the ability to be attached to biomolecules;
5) efficient chelation of divalent and trivalent metal cations;
6) absorption of light in the physiologically important region of 690–880 nm;
7) high chemical stability;
8) ability to stabilize diamagnetic complexes that form long-lived triplet states in high yield and that act as efficient photosensitizers for the formation of singlet oxygen.

The reduced sp³ form of the texaphyrin molecule has the structure $1_A$ shown in FIG. 1. Upon oxidation, an aromatic structure $1_B$ is formed and upon incorporation of a metal salt, such as $CdCl_2$, the chelate $1_C$ or its analogue incorporating other di- or trivalent cations, is formed. The synthetic scheme for the basic texaphyrin molecule is described in FIG. 2. These molecules are the subject of previous patent applications Ser. Nos. 771,393 and 539,975. The derivatives disclosed in this invention have substituents on the benzene ring portion of the molecule referred to as B or the tripyrrole portion of the molecule referred to as T. The number following the B or T indicates the number of hydroxyl groups that have been incorporated into that portion of the molecule.

The present invention relates to water soluble compounds retaining lipophilicity and having the structure:

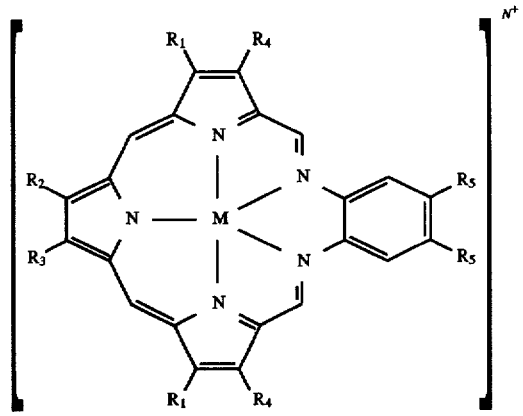

wherein M is H, a divalent or a trivalent metal cation;

wherein N is an integer between –20 and +2; and wherein the substituents $R_1$, $R_2$, $R_3$, $R_4$, and $R_5$ are independently hydrogen, [H];

hydroxyl, [OH];

alkyl groups attached via a carbon or oxygen;

hydroxyalkyl groups attached via a carbon or oxygen; these may be $C_nH_{(2n+1)}O_y$ or $OC_nH_{(2n+1)}O_y$; where at least one of the substituents $R_1$, $R_2$, $R_3$, $R_4$, and $R_5$ has at least one hydroxy substituent; where the molecular weight of any one of $R_1$, $R_2$, $R_3$, $R_4$, or $R_5$ is less than or equal to about 1000 daltons; where n is a positive integer or zero; and where y is zero or a positive integer less than or equal to (2n+1);

oxyhydroxyalkyl groups (containing independently hydroxy substituents or ether branches) attached via a carbon or oxygen; these may be $C_{(n-x)}H_{[(2n+1)-2x]}O_xO_y$ or $OC_{(n-x)}H_{[(2n+1)-2x]}O_xO_y$; where n is a positive integer or zero, x is zero or a positive integer less than or equal to n, and y is zero or a positive integer less than or equal to [(2n+1)–2x];

oxyhydroxyalkyl groups (containing independently substituents on the hydroxyls of the oxyhydroxyalkyl compounds described above or carboxyl derivatives) attached via a carbon or oxygen; these may be $C_nH_{[(2n+1)-q]}O_yR^a_q$, $OC_nH_{[(2n+1)-q]}O_yR^a_q$ or $(CH_2)_n CO_2R^a$; where n is a positive integer or zero, y is zero or a positive integer less than [(2n+1)–q], q is zero or a positive integer less than or equal to 2n+1, $R^a$ is independently H, alkyl, hydroxyalkyl, saccharide, $C_{(m-w)}H_{[(2m+1)-2w]}O_wO_z$, $O_2CC_{(m-w)}H_{[(2m+1)-2w]}O_wO_z$ or N(R)OCC$_{(m-w)}$H$_{[(2m+1)-2w]}$O$_w$O$_z$; where m is a positive integer or zero, w is zero or a positive integer less than or equal to m, z is zero or a positive integer less than or equal to [(2m+1)–2w], R is H, alkyl, hydroxyalkyl, or C$_m$H$_{[(2m+1)-r]}$O$_z$R$^b_r$; where m is a positive integer or zero, z is zero or a positive integer less than [(2m+1)–r], r is zero or a positive integer less than or equal to 2m+1, and R$^b$ is independently H, alkyl, hydroxyalkyl, or saccharide;

carboxyamidealkyl groups (containing independently hydroxyl groups, or secondary or tertiary amide linkages) attached via a carbon or oxygen; these may be (CH$_2$)$_n$CONHR$^a$, O(CH$_2$)$_n$CONHR$^a$, (CH$_2$)$_n$CON(R$^a$)$_2$ or O(CH$_2$)$_n$CON(R$^a$)$_2$; where n is a positive integer or zero, R$^a$ is independently H, alkyl, hydroxyalkyl, saccharide, C$_{(m-w)}$H$_{[(2m+1)-2w]}$O$_w$O$_z$, O$_2$CC$_{(m-w)}$H$_{[(2m+1)-2w]}$O$_w$O$_z$ or N(R)OCC$_{(m-w)}$H$_{[(2m+1)-2w]}$O$_w$O$_z$; where m is a positive integer or zero, w is zero or a positive integer less than or equal to m, z is zero or a positive integer less than or equal to [(2m+1)–2w], R is H, alkyl, hydroxyalkyl, or C$_m$H$_{[(2m+1)-r]}$O$_z$R$^b_r$; where m is a positive integer or zero, z is zero or a positive integer less than [(2m+1)–r], r is zero or a positive integer less than or equal to 2m+1, and R$^b$ is independently H, alkyl, hydroxyalkyl, or saccharide; or carboxyalkyl groups (containing independently hydroxyl groups, carboxyl substituted ethers, amide substituted ethers or tertiary amides removed from the ether) attached via a carbon or oxygen; these may be C$_n$H$_{[(2n+1)-q]}$O$_y$R$^c_q$ or OC$_n$H$_{[(2n+1)-q]}$O$_y$R$^c_q$; where n is a positive integer or zero, y is zero or a positive integer less than [(2n+1)–q], q is zero or a positive integer less than or equal to 2n+1, R$^c$ is (CH$_2$)$_n$CO$_2$R$^d$, (CH$_2$)$_n$CONHR$^d$ or (CH$_2$)$_n$CON(R$^d$)$_2$; where n is a positive integer or zero, R$^d$ is independently H, alkyl, hydroxyalkyl, saccharide, C$_{(m-w)}$H$_{[(2m+1)-2w]}$O$_w$O$_z$, O$_2$CC$_{(m-w)}$H$_{[(2m+1)-2w]}$O$_w$O$_z$ or N(R)OCC$_{(m-w)}$H$_{[(2m+1)-2w]}$O$_w$O$_z$; where m is a positive integer or zero, w is zero or a positive integer less than or equal to m, z is zero or a positive integer less than or equal to [(2m+1)–2w], R is H, alkyl, hydroxyalkyl or C$_m$H$_{[(2m+1)-r]}$O$_z$R$^b_r$; where m is a positive integer or zero, z is zero or a positive integer less than [(2m+1)–r], r is zero or a positive integer less than or equal to 2m+1, and R$^b$ is independently H, alkyl, hydroxyalkyl, or saccharide;

where at least one of R$_1$, R$_2$, R$_3$, R$_4$ and R$_5$ has at least one hydroxy substituent and the molecular weight of any of R$_1$, R$_2$, R$_3$, R$_4$ or R$_5$ is less than or equal to about 1000 daltons.

In the above-described metallic complexes M may be a divalent metal ion selected from the group consisting of Ca$^{+2}$, Mn$^{+2}$, Co$^{+2}$, Ni$^{+2}$, Zn$^{+2}$, Cd$^{+2}$, Hg$^{+2}$, Sm$^{+2}$ and UO$_2^{+2}$, (and N is 1). In certain aspects M is preferably Cd$^{+2}$ or Zn$^{+2}$ or Hg$^{+2}$. When M is a trivalent metal ion, it is preferably selected from the group consisting of Mn$^{+3}$, Co$^{+3}$, Ni$^{+3}$, Y$^{+3}$, In$^{+3}$, Pr$^{+3}$, Nd$^{+3}$, Sm$^{+3}$, Fe$^{+3}$, Ho$^{+3}$, Ce$^{+3}$, Eu$^{+3}$, Gd$^{+3}$, Tb$^{+3}$, Dy$^{+3}$, Er$^{+3}$, Tm$^{+3}$, Yb$^{+3}$, Lu$^{+3}$, La$^{+3}$ and U$^{+3}$; (and N is 2). Most preferred trivalent metal ions are In$^{+3}$, La$^{+3}$, Lu$^{+3}$, and Gd$^{+3}$.

A preferred water soluble compound retaining lipophilicity has hydroxyl groups only in the B portion of the molecule and has the structure:

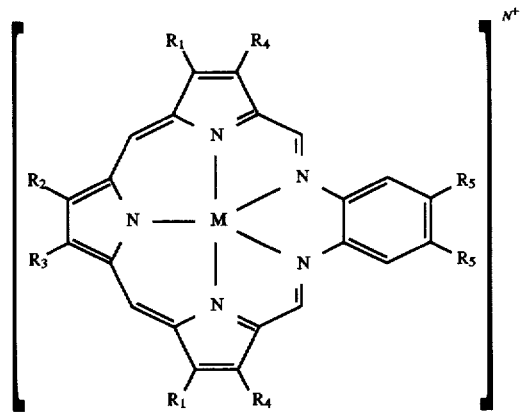

wherein M is H, a divalent or a trivalent metal cation; N is an integer between –20 and +2; R$_1$, R$_2$, R$_3$, and R$_4$ are independently C$_n$H$_{2n+1}$ where n is a positive integer; and R$_5$ is hydroxyl, hydroxyalkyl, oxyhydroxyalkyl, carboxyalkyl or carboxyamidealkyl; where R$_5$ has at least one hydroxy substituent, and the molecular weight of any one of R$_1$, R$_2$, R$_3$, R$_4$, or R$_5$ is less than or equal to about 1000 daltons.

Another preferred water soluble compound retaining lipophilicity has hydroxyl groups only in the T portion of the molecule and has the structure:

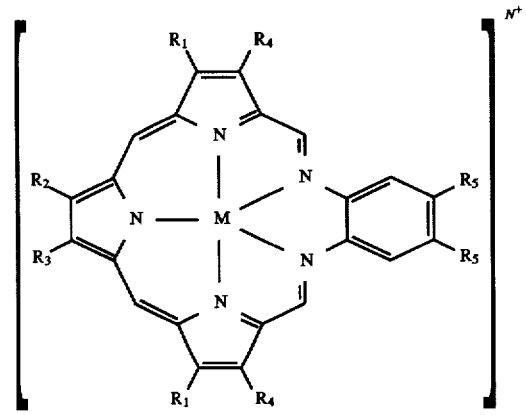

wherein M is H, a divalent or a trivalent metal cation; N is an integer between –20 and +2; R$_1$, R$_2$, R$_3$, and R$_4$ are independently hydroxyl, alkyl, hydroxyalkyl, oxyhydroxyalkyl, carboxyalkyl or carboxyamidealkyl; and R$_5$ is H or C$_n$H$_{2n+1}$; where at least one of R$_1$, R$_2$, R$_3$, and R$_4$ has at least one hydroxy substituent, the molecular weight of any one of R$_1$, R$_2$, R$_3$, R$_4$, or R$_5$ is less than or equal to about 1000 daltons, and n is a positive integer.

Another preferred water soluble compound retaining lipophilicity has hydroxyl groups in both the B and T portions of the molecule and has the structure:

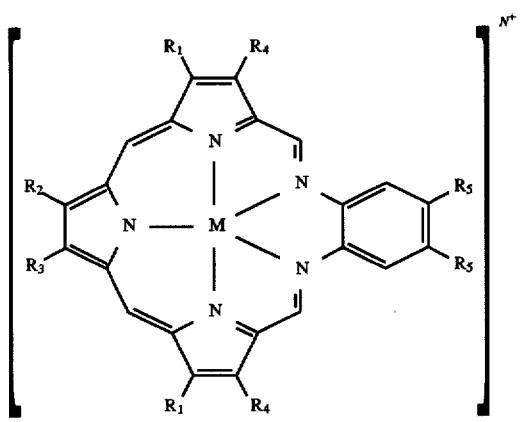

wherein M is H, a divalent or a trivalent metal cation; N is an integer between −20 and +2; $R_1$, $R_2$, $R_3$, $R_4$, and $R_5$ are independently H, OH, $C_nH_{(2n+1)}O_y$ or $OC_nH_{(2n+1)}O_y$; where at least one of $R_1$, $R_2$, $R_3$, and $R_4$ has at least one hydroxy substituent, $R_5$ has at least one hydroxy substituent, the molecular weight of any one of $R_1$, $R_2$, $R_3$, $R_4$, or $R_5$ is less than or equal to about 1000 daltons, n is a positive integer or zero, and y is zero or a positive integer less than or equal to (2n+1).

In the above described metallic complexes M may be a divalent metallic cation selected from the group consisting of $Ca^{+2}$, $Mn^{+2}$, $Co^{+2}$, $Ni^{+2}$, $Zn^{+2}$, $Cd^{+2}$, $Hg^{+2}$, $Sm^{+2}$ and $UO_2^{+2}$, and N is 1. When M is a trivalent metal cation, it is preferably selected from the group consisting of $Mn^{+3}$, $Co^{+3}$, $Ni^{+3}$, $Y^{+3}$, $In^{+3}$, $Pr^{+3}$, $Nd^{+3}$, $Sm^{+3}$, $Eu^{+3}$, $Gd^{+3}$, $Tb^{+3}$, $Dy^{+3}$, $Er^{+3}$, $Fe^{+3}$, $Ho^{+3}$, $Ce^{+3}$, $Tm^{+3}$, $Yb^{+3}$, $Lu^{+3}$, $La^{+3}$, and $U^{+3}$; and N is 2. Most preferred trivalent metal ions are $In^{+3}$, $Gd^{+3}$, $La^{+3}$, or $Lu^{+3}$ and N is +2.

A preferred water soluble compound retaining lipophilicity of this invention has been prepared as one having the structure with the trivial name B2 (See FIG. 6):

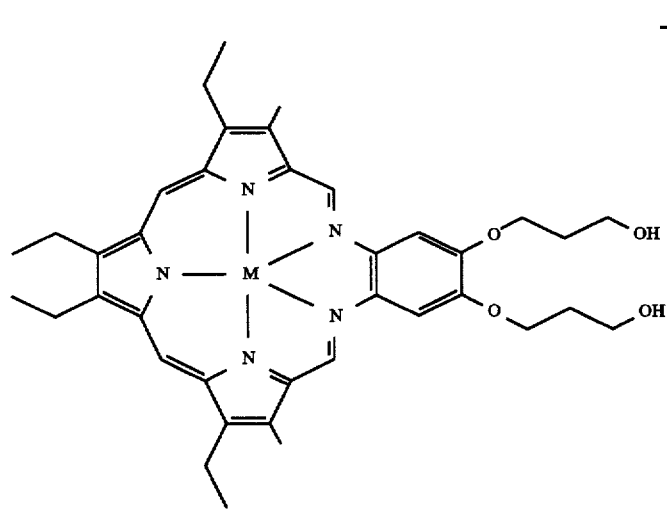

wherein M is H, a divalent or trivalent metal cation, and N is 0, 1 or 2. Particularly preferred metal cations are $Gd^{+3}$, $Lu^{+3}$, $La^{+3}$, or $In^{+3}$, and N is 2.

Another preferred water soluble compound retaining lipophilicity has the structure with the trivial name T2:

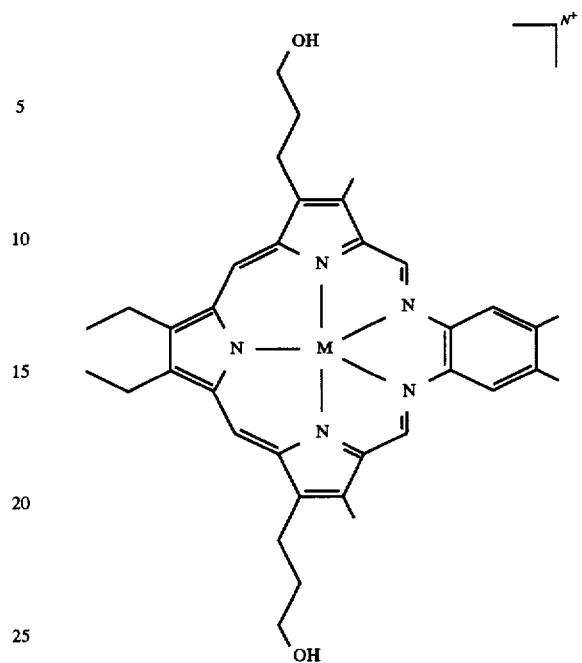

wherein M is H, a divalent or trivalent metal cation, and N is 0, 1 or 2. Particularly preferred metal cations are $Gd^{+3}$, $Lu^{+3}$, $La^{+3}$, $In^{+3}$, and N is 2.

Another preferred water soluble compound retaining lipophilicity has the structure with the trivial name B2T2 or T2B2:

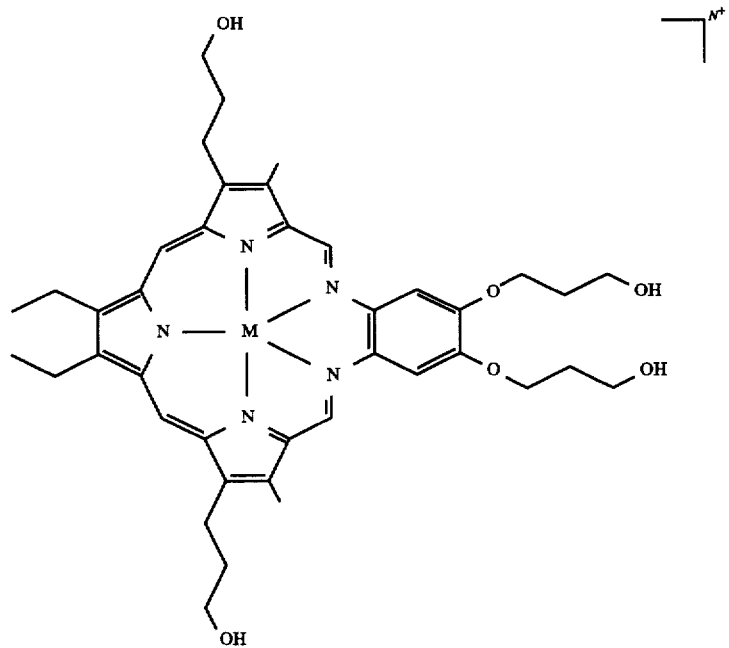

wherein M is H, a divalent or trivalent metal cation, and N is 0, 1 or 2. Particularly preferred metal cations are $Gd^{+3}$, $Lu^{+3}$, $La^{+3}$, or $In^{+3}$, and N is 2.

Another preferred water soluble compound retaining lipophilicity has the structure with the trivial name B4:

Another preferred water soluble compound retaining lipophilicity has the structure with the trivial name B4T2 or T2B4:

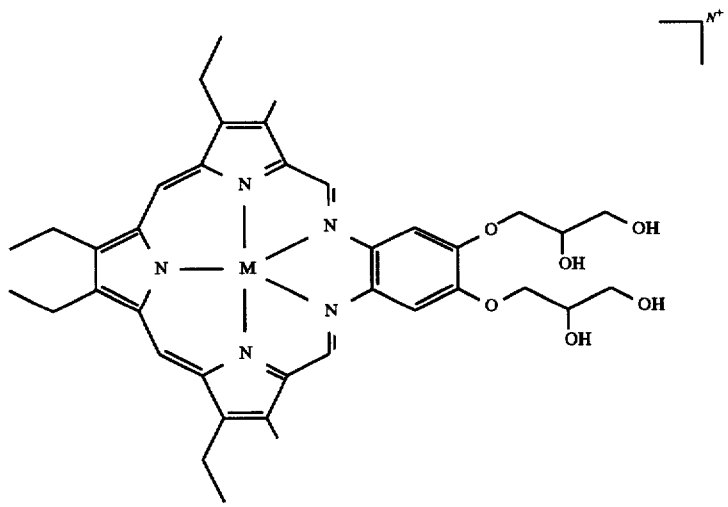

wherein M is H, a divalent or trivalent metal cation, and N is 0, 1 or 2 Particularly preferred metal cations are $Gd^{+3}$, $Lu^{+3}$, $La^{+3}$, or $In^{+3}$, and N is 2.

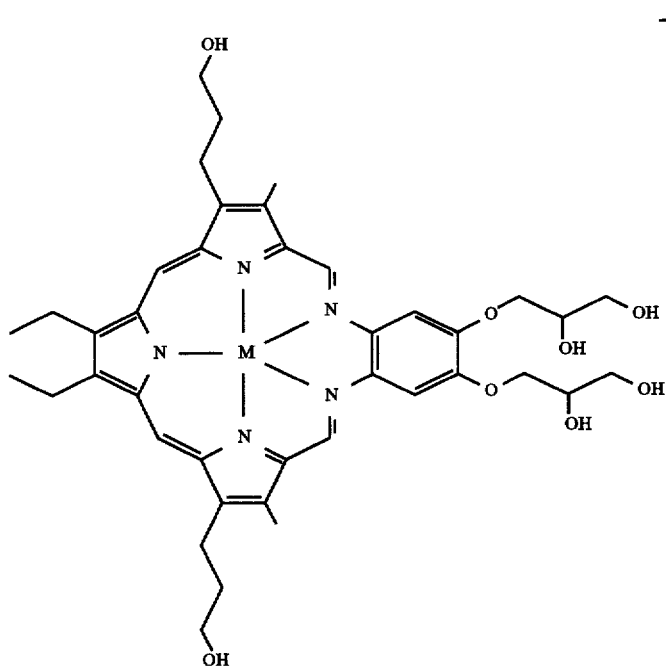

wherein M is H, a divalent or trivalent metal cation, and N is 0, 1 or 2. Particularly preferred metal cations are Gd$^{+3}$, Lu$^{+3}$, La$^{+3}$, or In$^{+3}$, and N is 2.

Another preferred water soluble compound retaining lipophilicity has the structure with the trivial name B4T3 or T3B4:

of Ca$^{+2}$, Mn$^{+2}$, Co$^{+2}$, Ni$^{+2}$, Zn$^{+2}$, Cd$^{+2}$, Hg$^{+2}$, Sm$^{+2}$ and UO$_2$$^{+2}$, and N is 1. When M is a trivalent metal cation, it is preferably selected from the group consisting of Mn$^{+3}$, Co$^{+3}$, Ni$^{+3}$, Y$^{+3}$, In$^{+3}$, Pr$^{+3}$, Nd$^{+3}$, Sm$^{+3}$, Eu$^{+3}$, Gd$^{+3}$, Tb$^{+3}$, Dy$^{+3}$, Er$^{+3}$, Fe$^{+3}$, Ho$^{+3}$, Ce$^{+3}$, Tm$^{+3}$, Yb$^{+3}$, Lu$^{+3}$, La$^{+3}$, and U$^{+3}$;

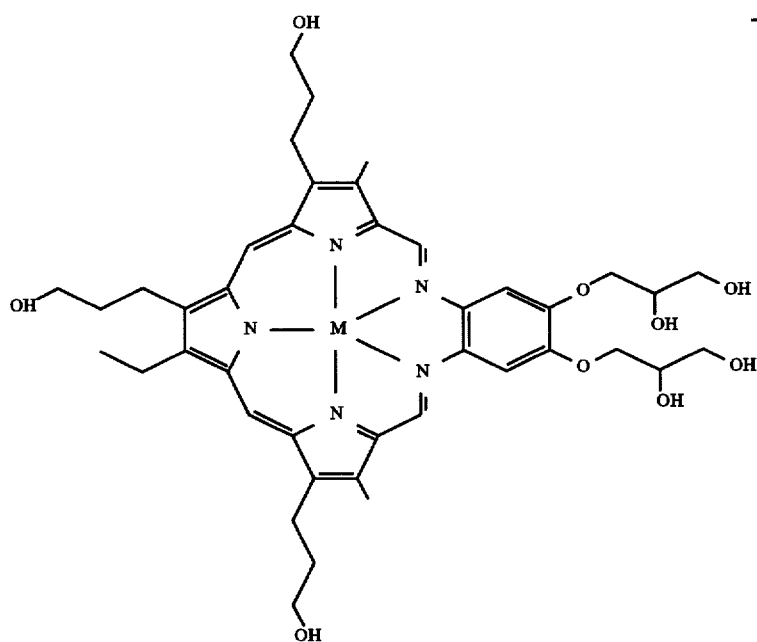

wherein M is H, a divalent or trivalent metal cation, and N is 0, 1 or 2. Particularly preferred metal cations are Gd$^{+3}$, Lu$^{+3}$, La$^{+3}$, or In$^{+3}$, and N is 2.

In the above described preferred compounds M may be a divalent metallic cation selected from the group consisting and N is 2. Most preferred trivalent metal ions are In$^{+3}$, Gd$^{+3}$, La$^{+3}$, or Lu$^{+3}$ and N is +2.

By combining various substituted intermediates, one skilled in the art can see how a large variety of hydroxy-substituted texaphyrins could be synthesized. Water soluble means soluble in aqueous fluids to about 1 mM or better. Retaining lipophilicity means having greater affinity for lipid rich tissues or materials than surrounding nonlipid rich tissues or materials and in the case of viruses in suspension means affinity for the membraneous coat of the virus. Lipid rich means having a greater amount of triglyceride, cholesterol, fatty acids or the like. Hydroxyalkyl means alkyl groups having hydroxyl groups attached. Oxyalkyl means alkyl groups attached to an oxygen. Oxyhydroxyalkyl means alkyl groups having ether or ester linkages, hydroxyl groups, substituted hydroxyl groups, carboxyl groups, substituted carboxyl groups or the like. Saccharide includes oxidized, reduced or substituted saccharide. Carboxyamidealkyl means alkyl groups with hydroxyl groups, secondary or tertiary amide linkages or the like. Carboxyalkyl means alkyl groups having hydroxyl groups, carboxyl or amide substituted ethers, ester linkages, tertiary amide linkages removed from the ether or the like.

A method for the synthesis of an aromatic pentadentate expanded porphyrin analog metal complex having at least one hydroxy substituent is an aspect of the present invention. By aromatic pentadentate expanded porphyrin analog we mean texaphyrin. This method comprises synthesizing a diformyltripyrrole having structure A; condensing said tripyrrole with an orthophenylenediamine having structure B:

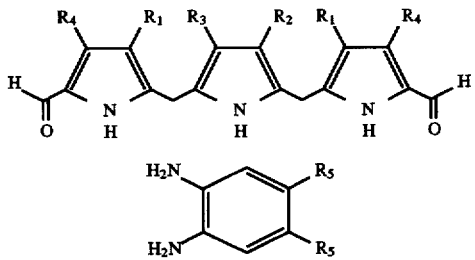

where $R_1$, $R_2$, $R_3$, $R_4$, and $R_5$ are independently H, OH, alkyl, oxyalkyl, hydroxyalkyl, carboxyalkyl, carboxyamidealkyl or oxyhydroxyalkyl and where at least one of $R_1$, $R_2$, $R_3$, $R_4$, and $R_5$ has at least one hydroxy substituent and where the molecular weight of any one of $R_1$, $R_2$, $R_3$, $R_4$, or $R_5$ is less than or equal to about 1000 daltons; and oxidizing the condensation product to form an aromatic pentadentate expanded porphyrin analog metal complex having at least one hydroxy substituent. A preferred diformyltripyrrole is 2,5-bis[(5-formyl-3-hydroxyalkyl-4-alkylpyrrol-2-yl)methyl]-3,4-dialkylpyrrole or 2,5-bis[(5-formyl-3-hydroxypropyl-4-methylpyrrol-2-yl)methyl]-3,4-diethylpyrrole, ($7_H$, FIG. 7); or 2,5-bis((3-ethyl-5-formyl-4-methylpyrrol-2-yl)methyl)-3,4-diethylpyrrole ($6_E$, FIG. 6).

A preferred "B" portion of these molecules is synthesized from phenylenediamine or 1,2-diamino-4,5-bis (oxyhydroxyalkyl)benzene or 1,2-diamino-4,5-bis((3'-hydroxypropyl)oxy)benzene, ($6_D$, FIG. 6), or 1,2-diamino-4,5-bis((2,3-dihydroxypropyl)oxy)benzene, ($8_D$, FIG. 8).

Said condensation product is mixed in an organic solvent with a trivalent metal salt, a Bronsted base and an oxidant; and stirred at ambient temperature or heated at reflux for at least 2–24 hours to form an aromatic pentadentate expanded porphyrin analog metal complex having at least one hydroxy substituent. A preferred Bronsted base is triethylamine; preferred oxidants are air, oxygen, platinum oxide, and 2,3-dichloro-5,6-dicyano-1,4-benzoquinone and preferred organic solvents are methanol and chloroform or methanol and benzene.

The metal complexes may be associated with, depending on the metal, anywhere from 0–6 apical ligands about the encapsulated metal center. The ligands are typically some combination of acetate, chloride, nitrate, hydroxide, water, or methanol and when bound, are not readily dissociable.

The present invention involves a method of deactivating retroviruses and enveloped viruses in an aqueous fluid. Aqueous fluid may be biological fluids, blood, plasma, edema tissue fluids, ex vivo fluids for injection into body cavities, cell culture media, supernatant solutions from cell cultures and the like. This method comprises adding a water soluble hydroxy-substituted aromatic pentadentate expanded porphyrin analog metal complex retaining lipophilicity to said aqueous fluid and exposing the mixture to light to effect the formation of singlet oxygen. Preferred metals are diamagnetic metals and a preferred metal complex is the Lu, La or In complex of B2T2.

A method of light-induced singlet oxygen production is an aspect of the present invention. The method comprises the use of a water soluble hydroxy-substituted aromatic pentadentate expanded porphyrin analog metal complex retaining lipophilicity and having intrinsic biolocalization selectivity as a photosensitizer. Preferred metals are diamagnetic metals and a preferred metal complex is the Lu, La or In complex of B2T2. Intrinsic biolocalization selectivity means having an inherently greater affinity for certain tissues relative to surrounding tissues.

A method of enhancement of relaxivity comprising the administration of a paramagnetic metal ion (such as gadolinium, for example) complexed with a water soluble hydroxy-substituted aromatic pentadentate expanded porphyrin analog retaining lipophilicity is an aspect of the present invention. A preferred complex is the Gd complex of B2T2.

A method of treating a host harboring atheroma or benign or malignant tumor cells is an aspect of the present invention. The method comprises the administration to a host as a first agent, a water soluble hydroxy-substituted aromatic pentadentate expanded porphyrin analog-detectable-metal complex retaining lipophilicity, said complex exhibiting selective biolocalization in such atheroma or tumor cells relative to surrounding tissue; determining localization sites in the host by reference to such detectable metal, followed by the administration to the host as a second agent a water soluble hydroxy-substituted aromatic pentadentate expanded porphyrin analog-detectable-metal complex retaining lipophilicity and having essentially identical biolocalization property and exhibiting the ability to generate singlet oxygen upon exposure to light; and photoirradiating the second agent in proximity to said atheroma or tumor cells. The first agent is further defined as being a paramagnetic metal complex, said paramagnetic metal serving as said detectable metal. In this case, the determination of localization sites occurs by magnetic resonance imaging and the second agent is a diamagnetic metal complex. The paramagnetic metal is most preferably Gd(III) and the diamagnetic metal is most preferably La(III), Lu(III) or In(III). A variation of this method uses as a first agent, a gamma emitting radioisotope as the detectable-metal complex, said gamma emitting radioisotope serving as said detectable metal; determination of localization sites occurs by gamma body scanning and is followed by photoirradiating the second agent as described above. A preferred first agent is the Gd complex of B2T2, 4,5-diethyl-10,23-dimethyl-9,24-bis(3-hydroxypropyl)-16,17-(3-hydroxypropyloxy)-13,20,25,26,27-pentaaza pentacyclo [20.2.1.1$^{3,6}$.1$^{8,11}$.0$^{14,19}$]heptacosa-1,3,5,7,9,11(27),12,14(19),15,17,20,22(25),23-tridecaene and a preferred second agent is the Lu, La or In complex of B2T2. Detectable as used herein means that the location may be found by localization means such as magnetic resonance imaging if the metal is paramagnetic or gamma ray detection if the metal is gamma emitting or using monochromatic X-ray photon sources. Selective biolocalization means having an inherently greater affinity for certain tissues relative to surrounding tissues. Essentially identical biolocalization property means the second agent is a texaphyrin derivative having about the same selective targeting characteristics in tissue as demonstrated by the first agent.

Another aspect of this invention is a method of imaging atheroma in a host comprising the administration to the host as an agent a water soluble hydroxy-substituted aromatic pentadentate expanded porphyrin analog-detectable-metal complex retaining lipophilicity, said complex exhibiting selective biolocalization in such atheroma; and imaging the atheroma in the host by reference to such detectable metal. The agent is preferably a water soluble hydroxy-substituted aromatic pentadentate expanded porphyrin analog-paramagnetic metal complex retaining lipophilicity, said paramagnetic metal serving as said detectable metal; and imaging of the atheroma occurs by magnetic resonance imaging. The paramagnetic metal is preferably Gd(III). The agent is preferably the Gd complex of B2T2, 4,5-diethyl-10,23-dimethyl-9,24-bis(3-hydroxypropyl)-16,17-(3-hydroxypropyloxy)-13,20,25,26,27-pentaaza pentacyclo [20.2.1.1$^{3,6}$.1$^{8,11}$.0$^{14,19}$]heptacosa-1,3,5,7,9,11(27),12,14(19),15,17,20,22(25),23-tridecaene.

In these methods of use, by water soluble hydroxy-substituted aromatic pentadentate expanded porphyrin analog retaining lipophilicity we mean water soluble texaphyrins retaining lipophilicity, however, one skilled in the art would recognize that water soluble hydroxy substituted sapphyrin metal complexes may be used in methods for generating singlet oxygen. Sapphyrins compounds are disclosed in patent application Ser. Nos. 454,298 and 454,301 which are incorporated by reference herein.

BRIEF DESCRIPTION OF THE DRAWINGS

FIG. 1 shows a schematic representation of the reduced ($1_A$) and oxidized ($1_B$) forms of the free-base "texaphyrin" and a representative five coordinate cadmium complex ($1_C$) derived from this "expanded porphyrin".

DESCRIPTION OF THE PREFERRED EMBODIMENT

Figure 2A:
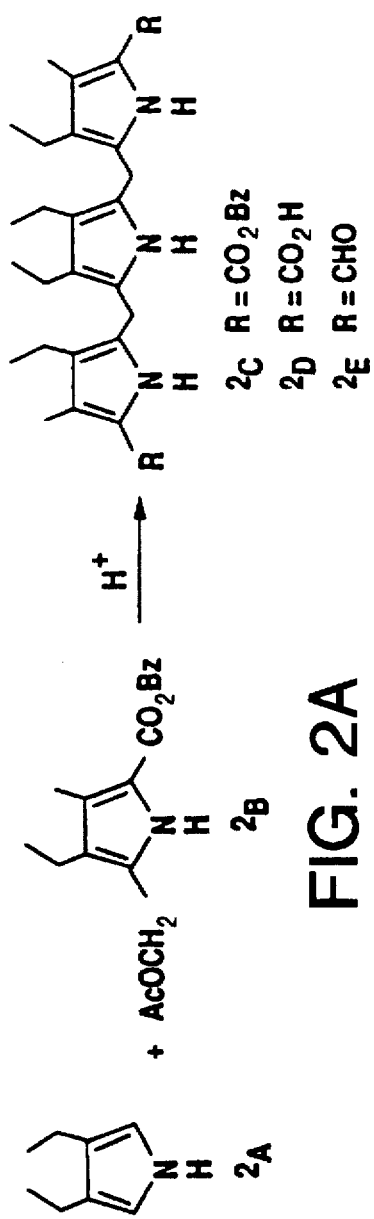
FIG. 2 schematically summarizes the synthesis of texaphyrin ($2_G$ also designated $1_B$ in FIG. 1).

The present invention involves the synthesis and utility of novel water soluble hydroxy-substituted aromatic pentadentate expanded porphyrin analog metal complexes retaining lipophilicity, in particular, hydroxy-substituted texaphyrin metal complexes. The presence in this structure of a near circular pentadentate binding core which is roughly 20% larger than that of the porphyrins, coupled with the realization that almost identical ionic radii pertain for hexacoordinate Cd$^{2+}$ (r=0.92 Å) and Gd$^{3+}$ (r=0.94 Å),[30] prompted exploration of the general lanthanide binding properties of this monoanionic porphyrin-like ligand. The synthesis and characterization of a water-stable gadolinium (III) complex derived formally from a 16,17-dimethyl substituted analogue of the original "expanded porphyrin" system is described, as well as the preparation and characterization of the corresponding europium(III) and samarium(III) complexes.

The aromatic "texaphyrin" system described herein provides an important complement to the existing rich coordination chemistry of porphyrins. For instance, by using methods similar to those described, zinc(II), manganese(II), mercury(II), Iron(III), neodymium(III), samarium(III), gadolinium(III), lutetium(III), indium(III), and lanthanum (III) complexes have been prepared and characterized.

The present invention involves hydroxy substituted derivatives of texaphyrin, and the synthesis and characterization thereof. The introduction of hydroxy substituents on the B (benzene ring) portion of the molecule is accomplished by their attachment to phenylenediamine in the 4 and 5 positions of the molecule. The introduction of hydroxy substituents on the T (tripyrrole) portion of the molecule is accomplished by appropriate functionalization of the alkyl substituents in the 3 and/or 4 positions of the pyrrole rings at a synthetic step prior to condensation with the substituted phenylenediamine. Most preferred derivatizations introduce substituents at the $R_1$ and $R_2$ sites of the diformyltripyrrole (A, pg 23) end at the $R_5$ sites of the orthophenylenediamine (B, pg 23). Standard deprotection methodology such as ester hydrolysis may be used to unmask the free hydroxyl substituents. These derivatives exhibit significant solubility in aqueous media, up to 1 mM or better, yet they retain affinity for lipid rich regions which allows them to be useful in a biological environment.

The photophysical properties of the tripyrroledimethine-derived "expanded porphyrins" are reported; these compounds show strong low energy optical absorptions in the 690–880 nm spectral range as well as a high triplet quantum yield, and act as efficient photosensitizers for the production of singlet oxygen, for example, in methanol solution.

Results indicate that these expanded porphyrin-like macrocycles are efficient photosensitizers for the destruction of free HIV-1 and for the treatment of atheroma, benign and malignant tumors in vivo and infected mononuclear cells in blood. Altering the polarity and electrical charges of side groups of these macrocycles will alter markedly the degree, rate, and site(s) of binding to free enveloped viruses such as HIV-1 and to virally-infected peripheral mononuclear cells, thus modulating photosensitizer take-up and photosensitization of leukemia or lymphoma cells contaminating bone-marrow. The use of La(III), Lu(III) or In(III) rather than Cd(II) for the production of singlet oxygen will reduce the toxicity of these compounds in any biomedical usage. A powerful technique is the use of these hydroxy-substituted texaphyrins in magnetic resonance imaging followed by photodynamic tumor therapy in the treatment of atheroma, and benign and malignant tumors.

EXAMPLE 1

Synthesis of Compounds $1_A$–$1_C$

Figure 2B:
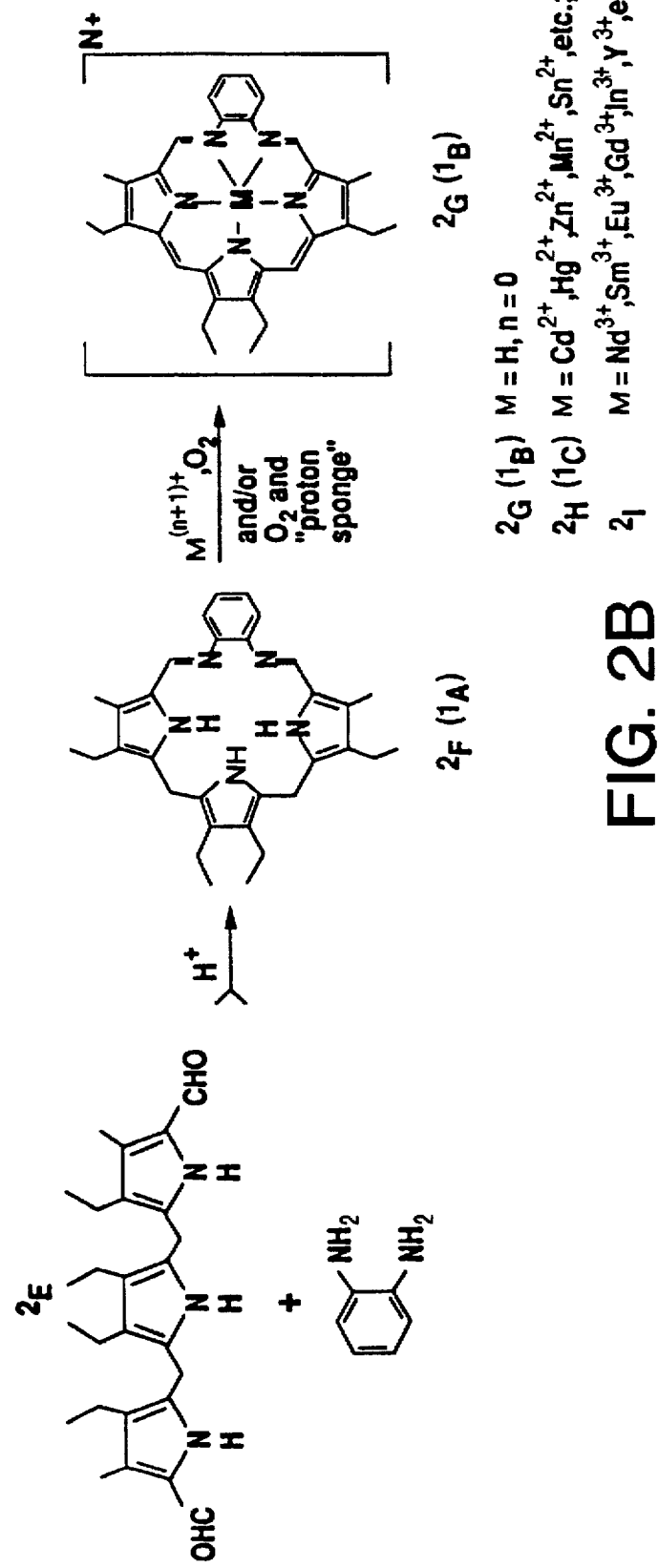

This example describes the synthesis of compounds depicted in FIGS. 1 and 2; the nonaromatic methylene-bridged macrocycle $1_A$, the expanded porphyrin named "texaphyrin" $1_B$ and the nitrate salt of the cadmium (II) complex $1_C$.

All solvents and reagents were of reagent grade quality, purchased commercially, and used without further purification. Sigma lipophilic Sephadex (LH-20-100) and Merck type 60 (230–400 mesh) silica gel were used for column chromatography. Melting points were recorded on a Mel-temp Laboratory Devices capillary apparatus and are uncorrected.

2,5-Bis[[5-(benzyloxycarbonyl)-3-ethyl-4-methylpyrrol-2-yl]methyl]-3,4-diethylpyrrole ($2_C$, FIG. 2). 3,4-Diethylpyrrole ($2_A$, FIG. 2)[28] (0.6, 4.9 mmol), benzyl 5-(acetoxymethyl)-3-methyl-4-ethyl-pyrrole-2-carboxylate ($2_B$, FIG. 2)[29] (2.5 g, 7.9 mmol), and p-toluenesulfonic acid (0.15 g) were dissolved in 60 mL of absolute ethanol and heated at 60° C. for 8 h under nitrogen. The resulting suspension was reduced in volume to 30 mL and placed in the freezer for several hours. The product was then collected by filtration, washed with a small amount of cold ethanol, and recrystallized from dichloromethane-ethanol to afford a white powder (2.07 g, 82%): mp 211° C. NMR spectra and high resolution mass spectral data were obtained as described and are reported [13a].

2,5-Bis[(3-ethyl-5-formyl-4-methylpyrrol-2-yl)methyl]-3,4-diethylpyrrole ($2_E$, FIG. 2). The above diester ($2_C$) (4.5 g, 7.1 mmol) was dissolved in 500 mL of dry THF containing 1 drop of triethylamine and hydrogenated over 5% palladium-charcoal (250 mg) at 1 atm $H_2$ pressure until the reaction was deemed complete by TLC. The catalyst was separated and the solution was taken to dryness on the rotary evaporator. Recrystallization from dichloromethane-hexane yielded $2_D$ (3.2 g, quantitative) as a white powder which quickly develops a red hue upon standing in air: mp 111°–115° C. dec. The above diacid (3 g, 6.6 mmol) was dissolved in 5 mL of freshly distilled trifluoroacetic acid and heated at reflux for 5 min under nitrogen and allowed to cool to room temperature over the course of 10 min. The above heating and cooling sequence was repeated once more and the resulting dark oil was then cooled in an ice-salt bath. Freshly distilled triethylorthoformate (5 mL) was then added dropwise with efficient stirring. After 10 min the solution was poured into 300 mL of ice water and let stand 30 min. The dark red precipitate was collected by filtration and washed well with water. Ethanol (ca. 50 mL) was then used to wash the precipitate from the filter funnel into 350 mL of 10% aqueous ammonia. The resulting yellow suspension was stirred well for an hour and then extracted with dichloromethane (5×150 mL). The dichloromethane extracts were washed with water, dried over $MgSO_4$, and evaporated to dryness on the rotary evaporator to give $2_E$ as an off-white mass. Two recrystallizations from chloroform-ethanol gave crystalline product (1.91 g, 68%) with mp 202°–203° C. NMR spectra and high resolution mass spectra data were obtained as described and are reported [13a].

4,5,9,24-Tetraethyl-10,23-dimethyl-13,20,25,26,27-pentaazapentacyclo[20.2.1.1$^{3,6}$.1$^{8,11}$.0$^{14,19}$]heptacosa-3,5,8,10,12,14(19),15,17,20,22,24-undecaene ($1_A$). A. Acid-Catalyzed Procedure. The diformyltripyrrane ($2_E$, FIG. 2) (105 mg, 0.25 mmol) and o-phenylenediamine (27 mg, 0.25 mmol) were dissolved, with heating, in a degassed mixture of 300 mL of dry benzene and 50 mL of absolute methanol. Concentrated HCl (0.05 mL) was then added and the resulting gold solution heated at reflux for 24 h under nitrogen. After cooling, solid $K_2CO_3$ (20 mg) was added and the solution filtered through $MgSO_4$. The solvent was then removed on the rotary evaporator and the resulting product dissolved in 50 mL of $CH_2Cl_2$ and refiltered (to remove unreacted $2_E$). Heptane (100 mL) was added to the filtrate and the volume reduced to 50 mL on the rotary evaporator whereupon the flask was capped and placed in the freezer overnight. The resulting white powder was then collected by filtration, washed with hexane, and dried in vacuo to yield $1_A$ (55 mg, 44%): mp 188°–190° C.

Metal Template Procedure. The diformyltripyrrane $2_E$ and o-phenylenediamine reactants were condensed together on a 0.25-mmol scale exactly as described above except that 1.0 equiv of either $Pb(SCN)_2$ (80 mg) or $UO_2Cl_2$ (85 mg) was added to the boiling solution at the outset of the reaction. Following workup as outlined above, 68 mg (69%) and 60 mg (61%) of $1_A$ were obtained respectively for the $Pb^{2+}$- and $UO_2^{2+}$-catalyzed reactions. The products produced in this manner proved identical with that prepared by procedure A. NMR spectra and high resolution mass spectra data were obtained as described and are reported [13a].

4,5,9,24-Tetraethyl-10,23-dimethyl-13,20,25,26,27-pentaazapentacyclo [20.2.1.1$^{3,6}$.1$^{8,11}$.0$^{14,19}$] heptacosa-1,3,5,7,9,11(27),12,14,16,18,20,22(25),23-tridecaene, free-base "texaphyrin" $1_B$. Macrocycle $1_A$ (50 mg, 0.1 mmol) was stirred in methanol/chloroform (150 ml, v/v/2/1) in the presence of N,N,N',N'-tetramethyl-1,8-diaminonaphthalene ("proton sponge") for one day at room temperature. The reaction mixture was then poured into ice water. The organic layer was separated and washed with aqueous ammonium chloride solution and then brine (a saturated solution of sodium chloride in water). Following concentration on a rotary evaporator, the crude material was purified by chromatography on SEPHADEX using first pure chloroform and then chloroform/methanol (v/v/10/1) as eluents. After several faster red bands were discarded, a dark green band was collected, concentrated in vacuo, and recrystallized from chloroform/n-hexane to give the sp$^2$ form of the ligand as a dark green powder in yields ranging from 3–12% with the better yields only being obtained on rare occasions. Spectral data are reported in the parent patent application Ser. No. 07/771,393.

The preparation of complex $1_C$·NO$_3$ was as follows: the reduced sp$^3$ form of the macrocyclic compound ($1_A$) (40 mg, 0.08 mmol) was stirred with cadmium nitrate tetrahydrate (31 mg, 0.1 mmol) in chloroform/methanol (150 ml, v/v/=½) for 1 day. The dark green reaction mixture was then concentrated and purified by chromatography on silica gel as described above. The resulting crude material was then recrystallized from chloroform/n-hexane to give analytically pure $1_C$·NO$_3$ in 27% yield. Under the reaction conditions both ligand oxidation and metal complexation take place spontaneously. Spectral data are reported in the parent patent application Ser. No. 07/771,393.

Figure 3B:
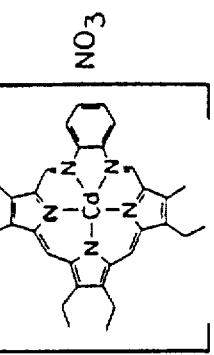
FIG. 3 shows $^1$H NMR spectrum of $1_C$·NO$_3$ in CDCl$_3$. The signals at 1.5 and 7.26 ppm represent residual water and solvent peaks respectively.
Figure 3A:
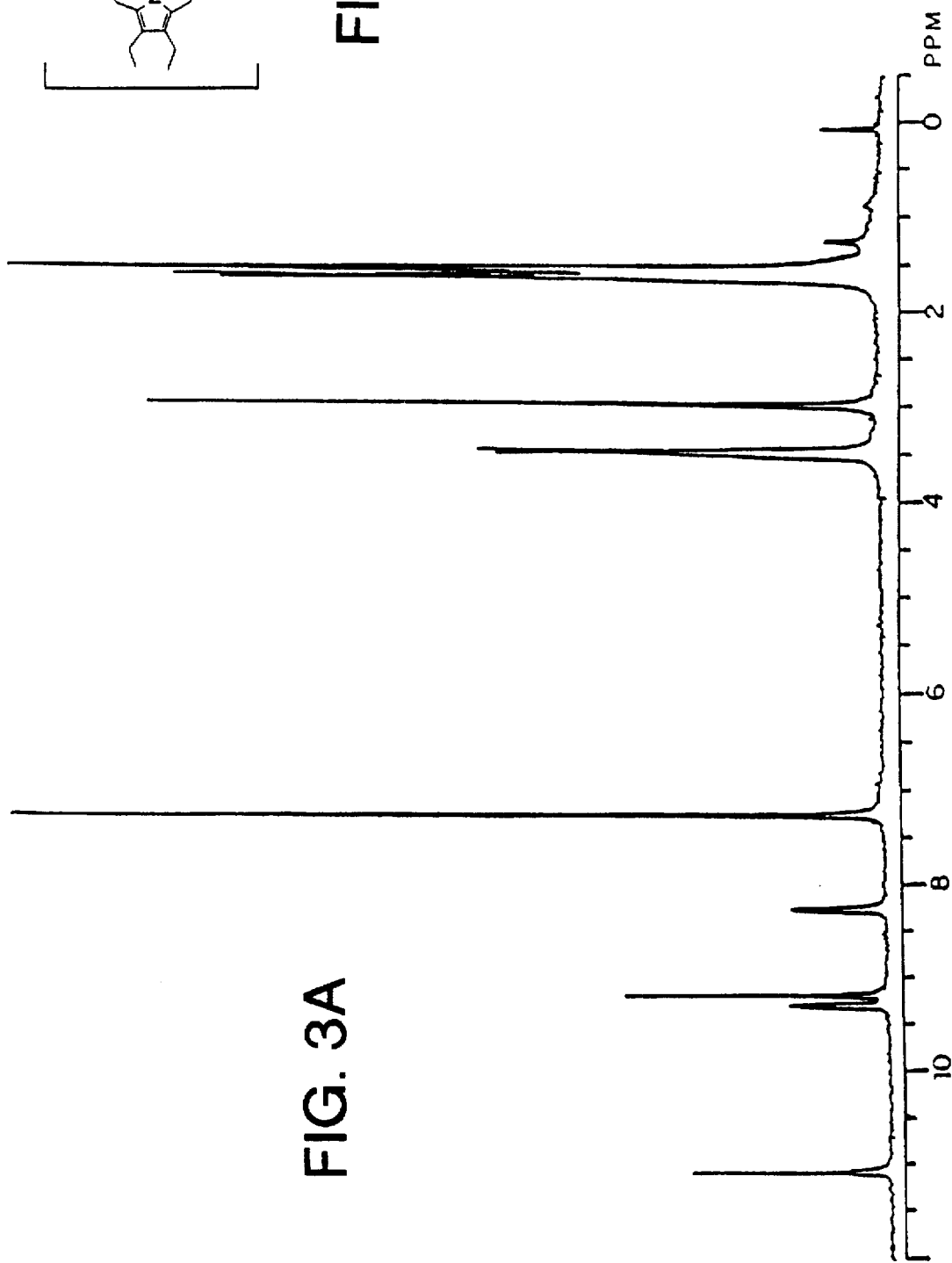

The structure of compound $1_C$ suggests that it can be formulated as either an 18π-electron benzannelated [18] annulene or as an overall 22 π-electron system; in either case an aromatic structure is defined. The proton NMR spectrum of complex $1_C$·NO$_3$·(HNO$_3$) (see FIG. 3) is consistent with the proposed aromaticity. For the most part, complex $1_C$·NO$_3$ shows ligand features which are qualitatively similar to those observed for compound $1_A$. As would be expected in the presence of a strong diamagnetic ring current, however, the alkyl, imine, and aromatic peaks are all shifted to lower field. Furthermore, the bridging methylene signals of compound $1_A$ (at δ4.0)[13] are replaced by a sharp singlet, at ca. 9.2 ppm, ascribable to the bridging methine protons. The chemical shift of this "meso" signal is similar to that observed for Cd(OEP)[16] (δ≈10.0),[17] an appropriate 18 π-electron aromatic reference system, and is also similar to that observed for the free-base form of decamethylsapphyrin (δ$^{11.5-11.7}$),[3] a 22 π-electron pyrrole-containing macrocycle.

Figure 4A:
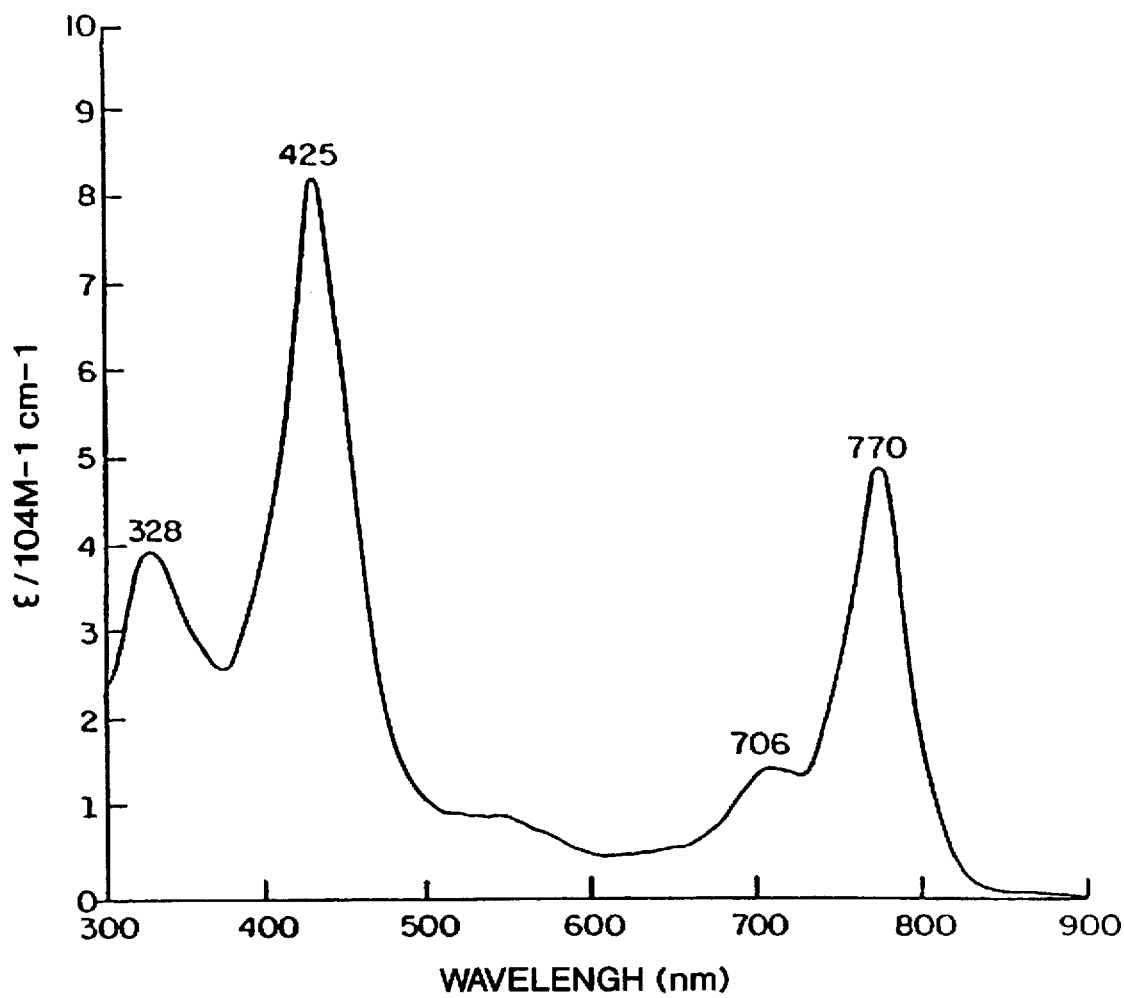
FIG. 4 shows a UV-visible spectrum of $1_C$·NO$_3$ 1.50×10$^{-5}$ M in CHCl$_3$.
Figure 4B:
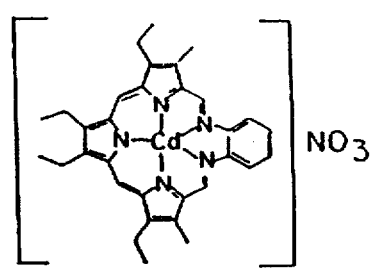

The optical spectrum of complex $1_C$·NO$_3$ (FIG. 4) bears some resemblance to those of other aromatic pyrrole-containing macrocycles[3,6,7,18] and provides further support for the proposed aromatic structure. The dominant transition is a Soret-like band at 424 nm (ε=72,700), which is considerably less intense than that seen for Cd(OEP)(pyr)[16] $\lambda_{max}$= 421 nm, ε=288,000.[18] This peak is flanked by exceptionally strong N- and Q-like bands at higher and lower energies. As would be expected for a larger π system, both the lowest energy Q-like absorption ($\lambda_{max}$=767.5 nm, ε=41,200) and emission ($\lambda_{max}$=792 nm)) bands of complex $1_C$·NO$_3$ are substantially red-shifted (by ca. 200 nm!) as compared to those of typical cadmium porphyrins.[18,19]

The molecular structure of the bis-pyridine adduct, determined by X-ray diffraction analysis confirms the aromatic nature of the ligand.[20] The central five nitrogen donor atoms of the complex are essentially coplanar and define a near circular cavity with a center-to-nitrogen radius of ca. 2.39 Å which is roughly 20% larger than that found in metalloporphyrins.[21] The Cd atom lies in the plane of the central N$_5$ binding core. The structure of the "expanded porphyrin" thus differs dramatically from that of CdTPP[16,22] or CdTPP-(dioxane)$_2$,[23] in which the cadmium atom lies out of the porphyrin N$_4$ donor plane (by 0.58 and 0.32 Å respectively). Moreover, in contrast to cadmium porphyrins, for which a five-coordinate square-pyramidal geometry is preferred and to which only a single pyridine molecule will bind,[24] in the bis-pyridine adduct, the cadmium atom is seven-coordinate, being complexed by two apical pyridine ligands. The configuration about the Cd atom is thus pentagonal bipyramidal; a rare but not unknown geometry for cadmium(II) complexes.[25]

Under neutral conditions complex $1_C$ appears to be more stable than cadmium porphyrins: Whereas treatment of CdTPP or CdTPP(pyr) with aqueous Na$_2$S leads to cation loss and precipitation of CdS, in the case of complex $1_C$ no demetallation takes place. (Exposure to aqueous acid, however, leads to hydrolysis of the macrocycle.) Indeed, it has not been possible to prepare the free-base ligand $1_B$ by demetallation. The tripyrroledimethine-derived free-base ligand $1_B$ was synthesized directly from $1_A$ by stirring in air-saturated chloroform-methanol containing N,N,N',N'-tetramethyl-1,8-diaminonaphthalene.[15] Although the yield is low (≦12%),[26] once formed, compound $1_B$ appears to be quite stable: It undergoes decomposition far more slowly than compound $1_A$.[13] Presumably, this is a reflection of the aromatic stabilization present in compound $1_B$. A further indication of the aromatic nature of the free-base "expanded porphyrin" $1_B$ is the observation of an internal pyrrole NH signal at δ=0.90, which is shifted upfield by over 10 ppm as compared to the pyrrolic protons present in the reduced macrocycle $1_A$.[13] This shift parallels that seen when the sp$^3$-linked macrocycle, octaethylporphyrinogen (δ(NH)= 6.9),[27] is oxidized to the corresponding porphyrin, H$_2$OEP (δ(NH)=−3.74).[17] This suggests that the diamagnetic ring current present in compound $1_B$ is similar in strength to that of the porphyrins.

EXAMPLE 2
Synthesis of compounds $5_A$–$5_E$

The presence in texaphyrin of a near circular pentadentate binding core which is roughly 20% larger than that of the porphyrins,[13b] coupled with the realization that almost identical ionic radii pertain for hexacoordinate Cd$^{2+}$ (r=0.92 Å) and Gd$^{3+}$ (r=0.94 Å),[30] prompted exploration of the general lanthanide binding properties of this new monoanionic porphyrin-like ligand. The synthesis and characterization of a water-stable gadolinium(III) complex ($5_C$) derived formally from a 16,17-dimethyl substituted analogue ($5_B$)[31] of the original "expanded porphyrin" system is described in this example.

All solvents and reagents were of reagent grade quality, purchased commercially, and used without further purification. Sigma lipophilic SEPHADEX (LH-20-100) and Merck type 60 (230–400 mesh) silica gel were used for column chromatography.

Compound $5_C$ is the metal adduct of ligand $5_A$ which was obtained in ca. 90% yield by condensing 1,2-diamino-4,5-dimethylbenzene with 2,5-Bis-(3-ethyl-5-formyl-4-methylpyrrol-2-ylmethyl)-3,4-diethylpyrrole under acid catalyzed conditions identical to those used to prepare $1_A$.[13a] The Sp$^3$ form of ligand $5_A$ (42 mg, 0.08 mmol) was stirred with gadolinium acetate tetrahydrate (122 mg, 0.3 mmol)

and Proton Sponge™, N,N,N',N'-tetramethyl-1,5-diaminonaphthalene (54 mg, 0.25 mmol) in chloroform/methanol (150 ml, v/v 1/2) for one day at room temperature. The dark green reaction mixture was concentrated under reduced pressure and chromatographed through silica gel (25 cm.×1.5 cm.) which was pretreated with chloroform/triethylamine (50 ml, v/v 25/1). Chloroform/triethylamine (25/1) and chloroform/methanol/triethylamine 25/2.5/1 v/v) was used as eluents. A dark red band was first collected followed by two green bands. The last green band, which showed a clear aromatic pattern by UV/VIS, was concentrated and recrystallized from chloroform/n-hexane to give 14 mg (22%) of the Gd complex $5_C$.

Treatment of compound $5_A$ with $Gd(OAc)_3$, $Eu(OAc)_3$, and $Sm(OAc)_3$ under reaction and work-up conditions similar to those used to obtain $1_C$, then gave the cationic complexes $5_C$, $5_D$, and $5_E$, as their dihydroxide adducts, in 22%, 33%, and 37% yields respectively. As judged by the IR and microanalytical data, under the reaction and work up conditions, hydroxide anions serve to displace the acetate ligands presumably present following the initial metal insertion procedure.

The new lanthanide complexes reported here are unique in several ways. For instance, as judged by fast atom bombardment mass spectrometric (FAB MS) analysis, complexes $5_C$–$5_E$ are mononuclear 1:1 species, a conclusion that is further supported, by both high resolution FAB MS accurate molecular weight determinations and combustion analysis. In other words, we have found no evidence of 1:2 metal to ligand "sandwich" systems, or higher order combinations as are often found in the case of the better studied lanthanide porphyrins.[32]

The electronic spectra represents a second remarkable feature of these new materials. The lanthanide complexes isolated to date display a dominant Soret-like transition in the 435–455 nm region which is considerably less intense than that observed in the corresponding metalloporphyrins,[33] and show a prominent low energy Q-type band in the 760–800 nm region. This latter feature is diagnostic of this class of 22 π-electron "expanded porphyrins"[13b] and is both considerably more intense and substantially red-shifted (by ca. 200 nm!) as compared to the corresponding transitions in suitable reference lanthanide porphyrins (e.g., $[Gd.TPPS]^+$, $\lambda_{max}$=575 nm[33]).

Within the context of these general observations, it is interesting to note that complexes derived from the somewhat more electron rich ligand $5_B$ all display Q-type bands that are blue shifted by ca. 5–15 nm as compared to those obtained from the original texaphyrin $1_B$.

A third notable property of complexes $5_C$–$5_E$ is their high solubility in both chloroform and methanol. The fact that these three complexes are also moderately soluble (to roughly $10^{-3}$M concentrations) in 1:1 (v.v.) methanol/water mixtures was of particular interest. For instance, a 3.5×10$^-$⁵M solution of the gadolinium complex $5_C$ in 1:1 (v.v.) methanol/water at ambient temperature shows less than 10% bleaching of the Soret and Q-type bands when monitored spectroscopically over the course of 2 weeks. This suggests that the half-life for decomplexation and/or decomposition of this complex is ≧100 days under these conditions. Under the conditions of the experiment described above, no detectable shifts in the position of the Q-type band are observed yet the Q-type transition of the free-base $5_B$ falls ca. 20 nm to the blue of that of $5_C$. Thus, shifts in this direction would be expected if simple demetalation were the dominant pathway leading to the small quantity of observed spectral bleaching.

The strong hydrolytic stability of complexes $5_C$–$5_E$ is in marked contrast to that observed for simple, water soluble gadolinium porphyrins, such as $[Gd.TPPS]^+$, which undergo water-induced demetalation in the course of several days when exposed to an aqueous environment.[33,34] It thus appears likely that gadolinium(III) complexes derived from the new texaphyrin ligand $5_B$, or its analogues, should provide the basis for developing new paramagnetic contrast reagents for use in MRI applications. In addition, the ease of preparation and stable mononuclear nature of complexes $5_C$–$5_E$ suggests that such expanded porphyrin ligands might provide the basis for extending further the relatively underdeveloped coordination chemistry of the lanthanides.

EXAMPLE 3
Synthesis of texaphyrin derivative B2

Nomenclature. The trivial abbreviations assigned to the hydroxylated derivatives of texaphyrin (TXP) in this and following examples refer to the number of hydroxyl groups attached to the benzene ring portion (B) and the tripyrrole (T) portion of the molecule.

General Information. $^1$H and $^{13}$C NMR spectra were obtained on a General Electric QE-300 (300 MHz.) spectrometer. Electronic spectra were recorded on a Beckman DU-7 spectrophotometer in $CHCl_3$. Infrared spectra were recorded, as KBr pellets, from 4000 to 600 $cm^{-1}$ on a Nicolet 510P FT-IR spectrophotometer. Chemical ionization mass spectrometric analyses (CI MS) were made using a Finnigan MAT 4023. Low resolution and high resolution fast atom bombardment mass spectrometry (FAB MS) were performed with a Finnigan-MAT TSQ-70 and VG ZAB-2E instruments, respectively. A nitrobenzyl alcohol (NBA) matrix was utilized with $CHCl_3$ as the co-solvent. Elemental analyses were performed by Atlantic Microlab, Inc. Melting points were measured on a Mel-temp apparatus and are uncorrected.

Materials. All solvents and reagents were of reagent grade quality, purchased commercially, and used as received. Merck Type 60 (230–400 mesh) silica gel was used for column chromatography. Thin-layer chromatography was performed on commercially prepared Whatman type silica gel 60A plates.

1,2-bis((2-carboxy)ethoxy)-4,5-dinitrobenzene. $6_B$, FIG. 6. To a well stirred solution of o-bis((3-hydroxypropyl)oxy)benzene[207] (5.0 g, 22 mmol) in 30 mL glacial acetic acid cooled to 15° C., 20 mL of concentrated nitric acid (70%) was added dropwise over a period of 15 minutes. The temperature was held below 40° C. by cooling and proper regulation of the rate of acid addition. After the addition, the yellow solution was stirred at room temperature for 15 minutes. Here, the solution was cooled again to 15° C. and 50 mL of fuming nitric acid (90%) was added dropwise over a period of 30 minutes. The orange solution was brought to room temperature and stirred for approximately 48 hours. After 48 hours, the reaction solution was checked by TLC, which displayed only one low $R_f$ spot, the diacid. Therefore, the orange solution was poured onto 600 mL of ice in a 1 liter beaker. The precipitated dinitro product was filtered, washed with water (1000 mL) until free from acid and dried in vacuo for 24 hours. The crude product was recrystallized from acetone/n-hexanes to yield the diacid as fluffy yellow needles (4.20 grams, 55.2%). For the diacid: $^1$H NMR ($d_6$-acetone) δ: 2.87 (t, 4H, $OCH_2CH_2CO_2H$), 4.49 (t, 4H, $OCH_2CH_2CO_2H$), 7.71 (s, 2H, Ar—H), 9–10 (br s, 2H, $CO_2H$). $^{13}$C NMR ($d_6$-acetone) δ: 33.76, 66.57, 109.85, 137.14, 152.06, 171.51. EI MS, m/z (rel. intensity: 346 (100))

1,2-bis((3-hydroxypropyl)oxy)-4,5-dinitrobenzene. $6_C$, FIG. 6. In a dry 500 mL round bottom flask, equipped with a 125 mL pressure equalized dropping funnel, 1,2-bis((2-carboxy)ethoxy)-4,5-dinitrobenzene (5.0 g, 14.5 mmol) was dissolved in 50 mL dry THF (distilled over ketyl) and stirred at 0°–10° C. under nitrogen. To the resulting clear solution, 120 mL of $BH_3 \cdot THF$ (1M) was added dropwise over a period of 30 minutes. After the borane addition, the reaction mixture was stirred an additional 5 minutes at 10° C. and then it was brought up to room temperature. The formation of the diol product was followed by TLC and the reaction was deemed complete after approximately 2 hours. The borane solution was quenched by careful addition of 65 mL of absolute methanol (Careful: frothing occurs!). After stirring the yellow solution for 30 minutes, it was concentrated to a bright yellow solid on a rotary evaporator. The crude solid was dissolved in 200 mL ethyl acetate and washed with 4M sodium acetate (2×100 mL), water (2×100 mL) and then brine (50 mL). The organic layer was dried over $MgSO_4$ and concentrated to dryness on a rotary evaporator. The crude product was recrystallized from acetone/n-hexanes to afford 4.12 grams (90%) of orange needles. For the diol: mp 129°–130° C.; $^1H$ NMR ($CDCl_3$) δ: 2.10 (p, 4H, $OCH_2CH_2CH_2OH$), 3.81 (t, 4H, $OCH_2CH_2CH_2OH$), 4.28 (t, 4H, $OCH_2CH_2CH_2OH$), 7.41 (s, 2H, Ar—H). $^{13}C$ NMR ($d_6$-acetone) δ: 32.52, 58.50, 67.81, 107.88, 137.03, 152.47. EI MS, m/z (rel. intensity): 316 (100); HRMS ($M^+$) 316.0914 (calcd. for $C_{12}H_{16}N_2O_8$: 316.0907).

Figure 6:
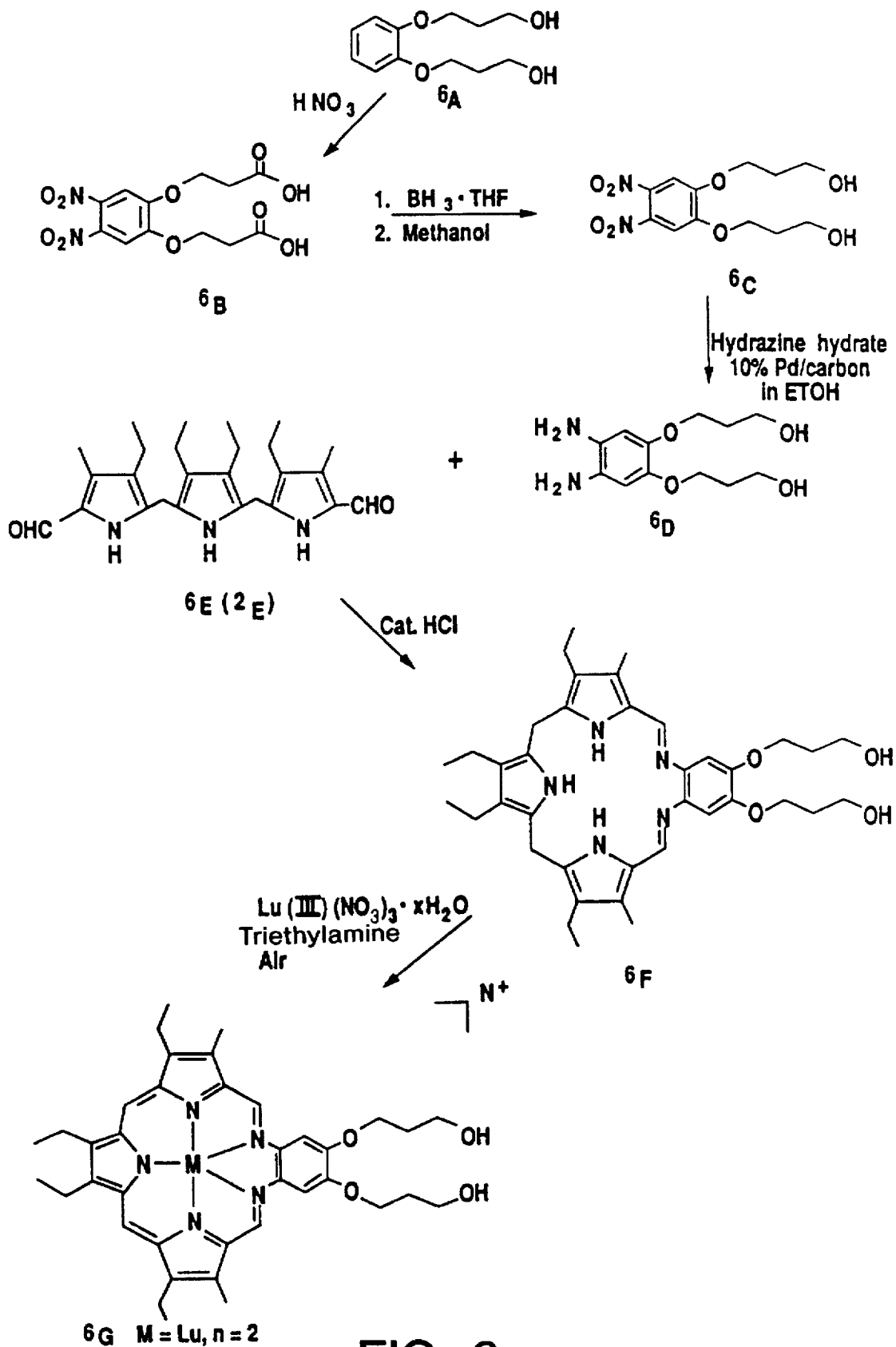
FIG. 6 schematically summarizes the synthesis of B2TXP, $6_F$ and [LuB2TXP]$^{2+}$,$6_G$, compounds of the present invention. Compounds $6_D$ and $6_E$ are claimed as intermediates in the synthesis of B2TXP in the present invention.

1,2-Diamino-4,5-bis(3'-hydroxypropyl)oxybenzene, $6_D$, FIG. 6. The diamine was obtained by reduction of the corresponding 1,2-bis((3-hydroxypropyl)oxy)-4,5-dinitrobenzene (3.0 g, 9.6 mmol) with hydrazine hydrate (4.7 mL, 96.2 mmol) and 10% palladium on carbon (200 mg) in 120 mL refluxing absolute ethanol. The resulting brown suspension bubbled for approximately 15–20 minutes and then turned colorless after 1 hour. At this point, the reduction was deemed complete as judged by TLC (a low $R_f$ spot). The reaction solution was hot filtered through celite into a dry flask, covered with aluminum foil, and then concentrated to a gray solid. The diamine was recrystallized from hot acetone/n-hexanes to yield 2.20 grams (91%) of an off-white fine powder. For the diamine: mp 115°–117° C.; $^1H$ NMR ($d_6$-DMSO) δ: 1.76 (p, 4H, $OCH_2CH_2CH_2OH$), 3.53 (q, 4H, $OCH_2CH_2CH_2OH$), 3.82 (t, 4H, $OCH_2CH_2CH_2OH$), 4.06 (s, 4H, NH), 4.44 (t, 2H, OH), 6.25 (s, 2H, ArH). $^{13}C$ NMR ($d_6$-DMSO) δ: 42.68, 67.84, 77.08, 114.95, 139.01, 150.63. EI MS, m/z (rel. intensity): 256 (100); HRMS ($M^+$) 256.1420 (calcd for $C_{12}H_{20}N_2O_4$: 256.1423).

4,5,9,24-Tetraethyl-16,17-bis((3-hydroxypropyl)oxy)-10,23-dimethyl-13,20,25,26,27-pentaazapentaoyclo [20.2.1.1$^{3,6}$.1$^{8,11}$.0$^{14,19}$]-heptacosa-3,5,8,10,12,14(19),15,17,20,22,24-undecaene. sp$^3$ B2 TXP, $6_F$, FIG. 6. This macrocycle was prepared in >90% yield from 1,2-diamino-4,5-bis ((3-hydroxypropyl)oxy)benzene and 2,5-bis((3-ethyl-5-formyl-4-methylpyrrol-2-yl)methyl)-3,4-diethyl pyrrole by using the acid-catalyzed procedure reported earlier for the preparation of the reduced sp$^3$ texaphyrin, see Example 1. For B2 sp$^3$ texaphyrin: mp 190° C. dec; $^1H$ NMR ($CDCl_3$) δ: 1.05 (t, 6H, $CH_2CH_3$), 1.12 (t, 6H, $CH_2CH_3$), 2.00 (t, 4H, $OCH_2CH_2CH_2OH$), 2.28 (s, 6H, pyrr-$CH_3$), 2.35 (q, 4H, $CH_2CH_3$), 2.48 (q, 4H $CH_2CH_3$), 3.00–3.50 (bs, 2H, OH), 3.78 (t, 4H, $OCH_2CH_2CH_2OH$), 3.93 (s, 4H, (pyrr)$_2$—$CH_2$), 4.19 (s, 4H, $OCH_2CH_2CH_2OH$), 7.16 (s, 2H, ArH), 8.34 (s, 2H, CHN), 11.16 (s, 1H, NH), 12.04 (s, 2H, NH); $^{13}C$ NMR ($CDCl_3$) δ: 9.65, 15.45, 16.61, 17.23, 17.60, 22.18, 31.71, 60.75, 68.58, 100.86, 120.23, 120.37, 124.97, 125.05, 130.05, 133.86, 140.16, 140.86, 147.62; UV/vis $\lambda_{max}$ 369 nm; CI MS ($M^+$) 642; CI HRMS ($M^+$) 642.4039 (calcd for $C_{34}H_{43}N_5O_2$: 642.4019).

Lutetium (III) complex of 4,5,9,24-tetraethyl-16,17-bis ((3-hydroxypropyl)oxy)-10,23-dimethyl-13,20,25,26,27-pentaazapentacyclo [20.2.1.1$^{3,6}$.1$^{8,11}$.0$^{14,19}$]heptacosa-1,3,5,7,9,11(27),12,14(19), 15,17,20,22(25),23-tridecaene [LuB2Txp]$^{2+}$ $6_G$, FIG. 6. A mixture of the reduced texaphyrin ligand, 4,5,9,24-tetraethyl-16,17-bis((3-hydroxypropyl)oxy)-10,23-dimethyl-13,20,25,26,27-pentaazapentacyclo [20.2.1.1$^{3,6}$.1$^{8,11}$.0$^{14,9}$]heptacosa 3,5,8,10,12,14(19),15,17,20,22,24-undecaene (100 mg., 0.16 mmol), lutetium (III) nitrate hydrate (177 mg, 0.47 mmol) and triethylamine (10 drops) were combined in 150 mL of refluxing methanol for 12–24 hours. The dark green reaction mixture was concentrated on a rotary evaporator to dryness and dried in vacuo for 24 hours. The crude complex was dissolved in a 100 mL 1:1 (v/v) mixture of chloroform and methanol, filtered through celite and concentrated to 20 mL. A small amount of silica gel (approx. 3 grams) was added to the flask and then the dark green solution was carefully concentrated to dryness on a rotary evaporator. The silica was dried for 2 hours in vacuo, then it was loaded on a chloroform packed silica column and the complex was purified by first using neat chloroform and then increasing concentrations of methanol in chloroform (0%–20%) as eluents. The dark green band collected from the column was concentrated to dryness on a rotary evaporator and recrystallized from chloroform/methanol/diethyl ether to yield 50 mg (ca. 35%) of the lutetium (III) B2 texaphyrin. For the Lu (III) complex: $^1H$ NMR ($CDCl_3/CD_3OH$) δ: 1.82–1.91 (m, 12H, $CH_2CH_3$), 2.39 (m, 4H, $OCH_2CH_2CH_2OH$), 3.32 (m, 4H, $OCH_2CH_2CH_2OH$), 3.39 (s, 6H, pyrr-$CH_3$), 3.92–4.04 (m, 12H, $OCH_2CH_2CH_2OH$ and $CH_2CH_3$), 9.52 (s, 2H, CH=C), 10.24 (s, 2H, ArH), 12.23 (s, 2H, CH=N); UV/vis: $\lambda_{max}$ 420.0, 477.5, 730.0; FAB MS $M^+$ 811.

Other lanthanide and rare earth-like metal complexes may be synthesized including the $Gd^{+3}$, $Lu^{+3}$, $La^{+3}$, $In^{+3}$ and $Dy^{+3}$ complexes.

EXAMPLE 4

Figure 7A:
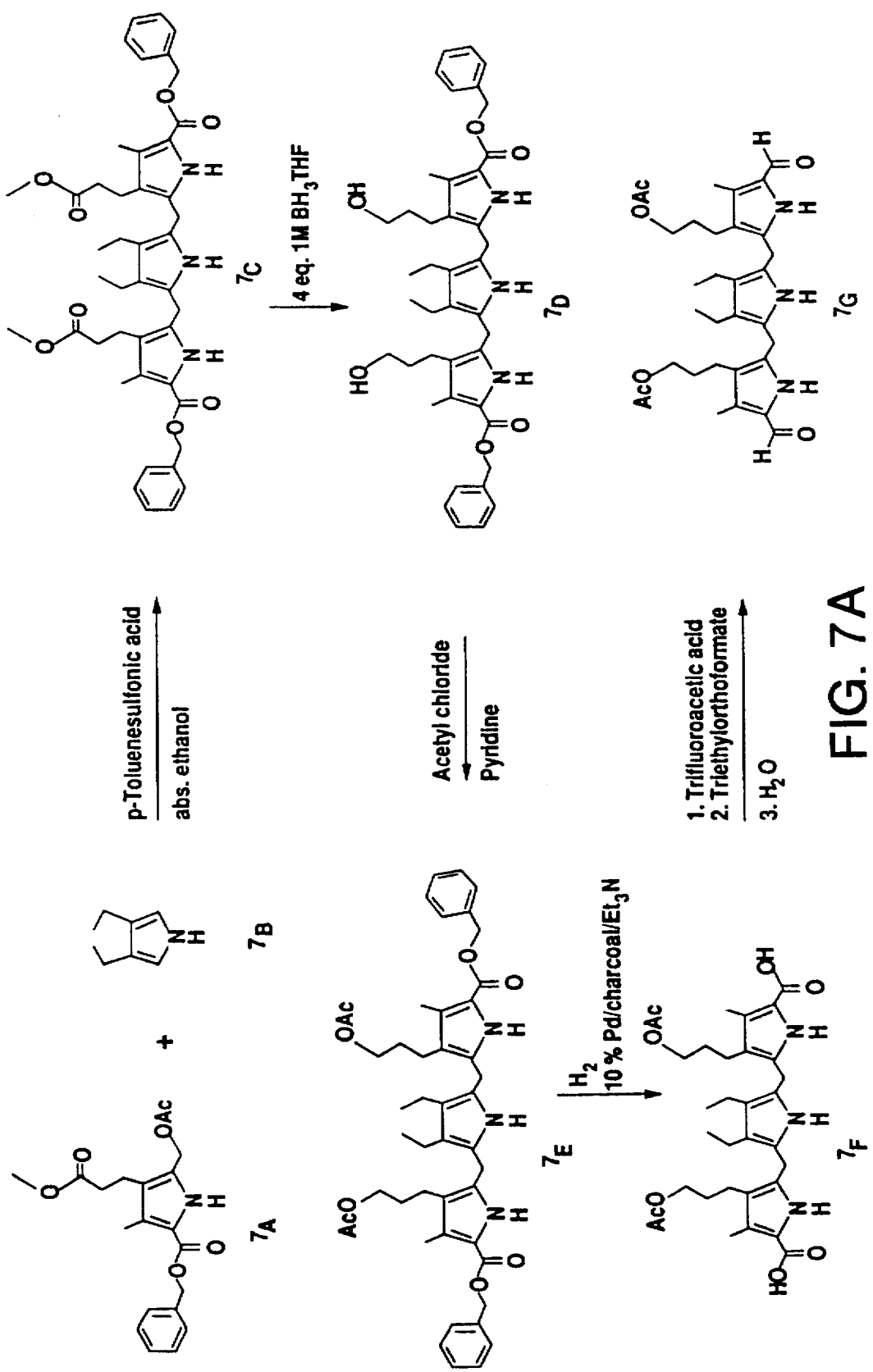
FIG. 7 schematically summarizes the synthesis of B2T2TXP($7_J$), [Gd B2T2 TXP]$^{2+}$ ($7_K$), [Lu B2T2 TXP]$^{2+}$ ($7_L$), and [La B2T2 TXP]$^{2+}$ ($7_M$), compounds of the present invention. Other trivalent metal complexes analogous to those shown can be prepared including that of In(III). Compound $7_H$ is claimed as an intermediate in the synthesis of B$_2$T2TXP in the present invention.
Figure 7B:
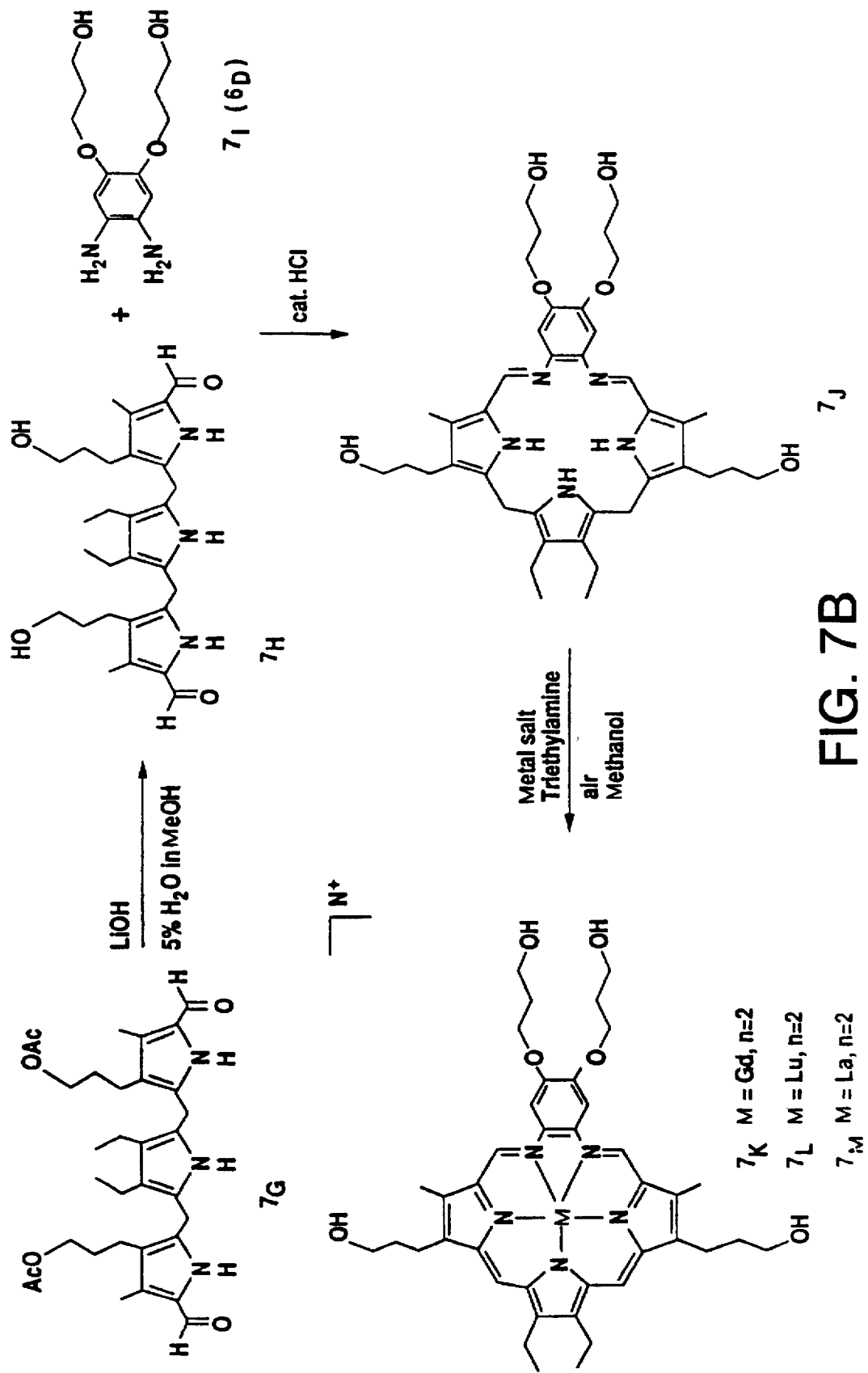

Synthesis of B2T2 TXP, see FIG. 7

2,5-Bis[(5-benzyloxycarbonyl-4-methyl-3-methoxycarbonylethylpyrrol-2-yl)methyl]-3,4-diethylpyrrole. $7_C$, FIG. 7. In a 500 mL round bottom flask was placed 250 mL of ethanol from an unopened bottle and this was then purged with dry nitrogen for ten minutes. 3,4-Diethylpyrrole $7_B$ (1.29 g, 0.01 mol) and 2-acetoxymethyl-5-benzyloxycarbonyl-4-methyl-3-methoxycarbonylethylpyrrole $7_A$ (7.83 g, 0.02 mol) were added and the mixture heated until all of the pyrroles dissolved. p-Toluenesulfonic acid (65 mg) was added and the reaction temperature maintained at 60° C. The reaction slowly changed color from a clear yellow to a dark red with the product precipitating out of the solution as the reaction progressed. After ten hours the reaction was cooled to room temperature, the volume reduced to one half on a rotary evaporator, and then placed in the freezer for several hours. The product was collected by filtration, washed with a small amount of cold ethanol to afford 4.61 g of an off white fine powder (61%): $^1H$ NMR ($CDCl_3$, 250 MHz): δ1.14 (6H, t, $CH_2CH_3$), 2.23 (6H, s, pyrrole-$CH_3$), 2.31 (4H, t, $CH_2CH_2CO_2CH_3$), 2.50 (4H, q, $CH_2CH_3$), 2.64 (4H, t, $CH_2CH_2CO_2CH_3$), 3.60 (10H, br s, $CH_3CO_2$— and (pyrrole)$_2$—$CH_2$), 4.44 (4H, br s, $C_6H_5CH_2$), 6.99–7.02 (4H, m, aromatic), 7.22–7.26 (6H, m, aromatic), 8.72 (1H, s, NH), 10.88 (2H, br s, NH); $^{13}C$ NMR ($CDCl_3$, 250 MHz): δ10.97, 16.78, 17.71, 19.40, 22.07, 35.09, 51.46, 65.32, 117.37, 119.34, 122.14, 126.58, 126.79, 127.36, 128.19, 133.55, 136.62, 162.35, 173.49; CI MS $(M+H)^+$ 750; HRMS 749.3676 (calc. for $C_{44}H_{51}N_3O_8$: 749.3676).

2,5-Bis[(5-benzyloxycarbonyl-3-hydroxypropyl-4-methylpyrrol-2-yl)methyl]-3,4-diethylpyrrole. $7_D$. FIG. 7. 2,5-Bis[(5-benzyloxycarbonyl-4-methyl-3-methoxycarbonylethylpyrrol-2-yl)methyl]-3,4-diethylpyrrole $7_C$ (5.00 g, 0.007 mol) was placed in a three necked 100 mL round bottom flask and vacuum dried for at least 30 minutes. The flask was equipped with a thermometer, an addition funnel, a nitrogen inlet tube, and a magnetic stir bar. After the tripyrrane was partially dissolved into 10 mL of dry THF, 29 mL of borane (1M $BH_3$ in THF) was added dropwise with stirring. The reaction became mildly exothermic and was cooled with a cool water bath. The tripyrrane slowly dissolved to form a homogeneous orange solution which turned to a bright fluorescent orange color as the reaction went to completion. After stirring the reaction for one hour at room temperature, the reaction was quenched by adding methanol dropwise until the vigorous effervescence ceased. The solvents were removed under reduced pressure and the resulting white solid redissolved into $CH_2Cl_2$. The tripyrrane was washed three times with 0.5M HCl (200 mL total), dried over anhydrous $K_2CO_3$, filtered, and the $CH_2Cl_2$ removed under reduced pressure until crystals of the tripyrrane just started to form. Hexanes (50 mL) was added and the tripyrrane allowed to crystallize in the freezer for several hours. The product was filtered and again recrystallized from $CH_2Cl_2$/ethanol. The product was collected by filtration and vacuum dried to yield 3.69 g of an orangish white solid (76%): mp 172°–173° C.; $^1$H NMR ($CDCl_3$, 300 MHz): δ1.11 (6H, t, $CH_2CH_3$), 1.57 (4H, p, $CH_2CH_2CH_2OH$), 2.23 (6H, s, pyrrole-$CH_3$), 2.39–2.49 (8H, m, $CH_2CH_3$ and $CH_2CH_2CH_2OH$), 3.50 (4H, t, $CH_2CH_2CH_2OH$), 3.66 (4H, s, (pyrrole)$_2$—$CH_2$), 4.83 (4H, s, $C_6H_5$—$CH_2$), 7.17–7.20 (4H, m, aromatic), 7.25–7.30 (6H, m, aromatic), 8.64 (1H, s, NH), 9.92 (2H, s, NH); $^{13}$C NMR ($CDCl_3$, 300 MHz): δ10.97, 16.72, 17.68, 20.00, 22.38, 33.22, 62.01, 65.43, 117.20, 119.75, 120.72, 122.24, 127.23, 127.62, 128.30, 132.95, 136.60, 162.13; FAB MS ($M^+$) 693.

2,5-Bis[(3-acetoxypropyl-5-benzyloxycarbonyl-4-methylpyrrol-2-ylmethyl]-3,4-diethylpyrrole. $7_E$. FIG. 7. 2,5-Bis[(5-benzyloxycarbonyl-3-hydroxypropyl-4-methylpyrrol-2-yl)methyl]-3,4-diethylpyrrole $7_D$ (36.4 g, 0.05 mol) was placed in a 1 L three necked round bottom flask and dried under vacuum for at least 30 minutes. The flask was equipped with a dropping funnel, a thermometer, a nitrogen inlet tube, and a magnetic stir bar. $CH_2Cl_2$ (600 mL dried over $CaH_2$) was added to the tripyrrane and stirred under nitrogen to form an orange suspension. Pyridine (10.5 mL) was added directly to the flask followed by acetyl chloride (9.5 mL) in 50 mL of dry $CH_2Cl_2$ which was added dropwise from the addition funnel at such a rate that the temperature of the reaction didn't exceed 25° C. An ice/water bath was used to cool the reaction. The tripyrrane slowly dissolved as the acetyl chloride was added to form a dark red homogeneous solution. The reaction was stirred at room temperature for approx. 3 hours then quenched with sat. aq. $NaHCO_3$. The organic layer was separated, washed three times with 0.5M HCl, then once with sat. $NaHCO_3$. The organic layer was separated, dried over $MgSO_4$, filtered, then reduced to dryness on the rotary evaporator. The orange solid was dried in vacuo for several hours then redissolved into $CH_2Cl_2$ and crystallized using hexanes. 36.8 g of an orange colored product was obtained (89%). A purer product can be obtained by recrystallization from $CH_2Cl_2$/ethanol. For tripyrrane $7_E$: mp 127°–129° C.; $^1$H NMR ($CDCl_3$, 300 MHz): δ1.14 (6H, t, $CH_2CH_3$), 1.67 (4H, p, $CH_2CH_2CH_2OAc$), 2.04 (6H, s, $CH_3CO_2CH_2$), 2.22 (6H, s, pyrrole-$CH_3$), 2.37 (4H, t, $CH_2CH_2CH_2OAc$), 2.48 (4H, q, $CH_2CH_3$), 3.57 (4H, s, (pyrrole)$_2$—$CH_2$), 3.98 (4H, t, $CH_2CH_2CH_2OAc$), 4.45 (4H, s, $C_6H_5$—$CH_2$), 7.01–7.03 (4H, m, aromatic), 7.23–7.29 (6H, m, aromatic), 8.69 (2H, s, NH), 10.95 (1H, s, NH); $^{13}$C NMR ($CDCl_3$, 300 MHz): δ11.06, 16.89, 17.74, 20.19, 20.93, 21.98, 29.70, 63.83, 65.31, 117.38, 118.81, 119.89, 122.24, 126.42, 126.68, 127.24, 128.11, 133.53, 136.73, 162.62, 171.12; CI MS ($M^+$) 777; HRMS (M+H)$^+$, 778.4060 (calc. for $C_{46}H_{56}N_3O_8$, 778.4067).

2,5-Bis[(3-acetoxypropyl-5-carboxyl-4-methylpyrrol-2-yl) methyl]-3,4-diethylpyrrole. $7_F$. FIG. 7 2,5-Bis[(3-acetoxypropyl-5-benzyloxycarbonyl-4-methylpyrrol-2-yl) methyl]-3,4-diethylpyrrole $7_E$ (15.0 g, 0.02 mol) was placed in a 500 mL side arm round bottom flask and dried under vacuum for at least 30 minutes. After dissolving the tripyrrane into 400 mL of dry THF, 10% Pd on carbon (0.75 g) and two drops of triethylamine were added and the mixture stirred at room temperature under one atm. of $H_2$. After 15 hrs. celite was added to the mixture and the catalyst was filtered off. The light orange solution was reduced to one half volume under reduce pressure, then 100 mL of heptane was added and the solution further reduced in volume until crystals of the tripyrrane diacid just started to appear. The tripyrrane was allowed to crystallize in the freezer for several hours and then filtered to yield a white color solid which developed a reddish hue on standing in air. 10.94 grams of product was obtained (96%): mp 146–148 dec; $^1$H NMR ($CDCl_3$, 300 MHz): δ1.09 (6H, t, $CH_2CH_3$), 1.76 (4H, p, $CH_2CH_2CH_2OAc$), 2.03 (6H, s, $CH_3CO_2$), 2.23 (6H, s, pyrrole-$CH_3$), 2.42 (4H, q, $CH_2CH_3$), 2.49 (4H, t, $CH_2CH_2CH_2OAc$), 3.77 (4H, s, (pyrrole)$_2$—$CH_2$), 4.01 (4H, t, $CH_2CH_2CH_2OAc$), 8.23 (1H, s, NH), 9.29 (2H, s, NH); FAB MS ($M^+$) 597.

2,5-Bis[(3-acetoxypropyl-5-formyl-4-methylpyrrol-2-yl) methyl]-3,4-diethylpyrrole. $7_G$. FIG. 7. 2,5-Bis[(3-acetoxypropyl-5-carboxyl-4-methylpyrrol-2-yl)methyl]-3,4-diethylpyrrole $7_F$ (5.80 g, 0.0097 mol) was placed in a 250 mL round bottomed flask equipped with a nitrogen inlet and a magnetic stir bar. At room temperature under nitrogen trifluoroacetic acid (16 mL) was added to the tripyrrane dropwise via syringe. The tripyrrane dissolved with visible evolution of $CO_2$ to form a dark orange solution. The reaction was stirred at room temperature for 10–15 minutes, then cooled to –20° C. using a dry ice/$CCl_4$ bath. Freshly distilled triethylorthoformate (16 mL, dried over $CaH_2$) was added dropwise via syringe to produce a deep red solution which was stirred an additional ten minutes at –20° C. The cold bath was removed and 100 mL of water was added slowly to the solution. A precipitate formed during addition of the water and the resulting orange suspension was stirred at room temperature for 20–30 minutes. The product was collected by filtration, washed several times with water, and resuspended in 1:1 50% aqueous $NH_4OH$/Ethanol (240 mL). The yellow/brown suspension was stirred for one hour at room temperature, filtered, washed several times with water and then washed with a small amount of cold ethanol. The tripyrrane was recrystallized from $CH_2Cl_2$/ethanol to yield 4.50 g of a reddish color solid (82%): mp 179°–181° C.; $^1$H NMR ($CDCl_3$, 300 MHz): δ1.11 (6H, t, $CH_2CH_3$), 1.67 (4H, p, $CH_2CH_2CH_2OAc$), 2.05 (6H, s, $CH_3CO_2$—), 2.19 (6H, s, pyrrole-$CH_3$), 2.42–2.49 (8H, m, $CH_2CH_3$ and $CH_2CH_2CH_2OAc$), 3.83 (4H, s, (pyrrole)$_2$—$CH_2$), 3.99 (4H, t, $CH_2CH_2CH_2OAc$), 9.07 (2H, s, CHO), 9.42 (1H, s, NH), 10.70 (2H, s, NH); $^{13}$C NMR ($CDCl_3$, 300 MHz): δ8.75, 16.55, 17.62, 19.98, 20.85, 22.56, 29.04, 63.71, 120.26, 121.41, 121.65, 128.02, 132.81, 138.52, 171.08, 175.38; CI MS (M+1)⁺ 567; HRMS (M+H)⁺, 566.3208 (calc for $C_{38}H_{44}N_3O_6$, 566.3230)

2,5-Bis[(5-formyl-3-hydroxypropyl-4-methylpyrrol-2-yl) methyl]-3,4-diethylpyrrole. $7_H$. FIG. 7. 2,5-Bis[(3-acetoxypropyl-5-formyl-4-methylpyrrol-2-yl)methyl]-3,4-diethylpyrrole $7_G$ (5.98 g, 0.011 mol) and LiOH (1.76 g, 0.042 mol) were added to 400 mL of 95% methanol, which had been degassed with nitrogen prior to use, add the mixture heated to reflux under a nitrogen atmosphere. The reaction became homogeneous when heated. After heating for 1.25 hours, the reaction was allowed to cool to room temperature. The product precipitated as a tan color solid as the reaction cooled. The volume of the reaction mixture was reduced to 75 mL on a rotary evaporator and the resulting slurry placed in the freezer for several hours. The product was filtered, and then purified by forming a slurry with 400 mL of methanol and 50 mL of water and heating close to boiling. The slurry was first cooled to room temperature, reduced to ½ volume under reduced pressure, and placed in the freezer for several hours. The product was collected by filtration and vacuum dried to yield 4.96 g of a tan powder (94%): ¹H NMR (CD₃OD, 300 MHz): δ0.96 (6H, t, $CH_2CH_3$), 1.49 (4H, p, $CH_2CH_2CH_2OH$), 2.25 (6H, s, pyrrole-$CH_3$), 2.32–2.43 (8H, m, $CH_2CH_3$ and $CH_2CH_2CH_2OH$), 3.46 (4H, t, $CH_2CH_2CH_2OH$), 3.85 (4H, s, (pyrrole)₂—$CH_2$),9.34 (2H, s, CHO); CI MS (M⁺) 480; HRMS (M)⁺, 481.2942 (calc for $C_{28}H_{39}N_3O_4$, 481.2941).

4,5-Diethyl-10,23-dimethyl-9,24-bis(3-hydroxypropyl)-16,17-bis(3-hydroxypropyloxy)-13,20,25,26,27-pentaazapentacyclo[20.2.1.1³,⁶.1⁸,¹¹.0¹⁴,¹⁹]heptacosa-3,5,8,10,12,14(19), 15,17,20,22,24-undecaene. $7_J$. FIG. 7. 2,5-Bis [(5-formyl-3-hydroxypropyl- 4-methylpyrrol-2-yl)methyl]-3,4-diethylpyrrole $7_H$ (1.00 g, 0.002 mol) and 1,2-diamino-4,5-bis(3-hydroxypropyloxy)benzene $7_I$ (0.52 g, 0.002 mol) were placed in a 2 L round bottom flask with 1000 mL of toluene and 200 mL of methanol. The solvents were purged with nitrogen prior to use. Concentrated HCl (0.5 mL) was added and the reaction heated to reflux under nitrogen. The reaction went from a clear suspension of starting materials to a dark red homogeneous solution as the reaction proceeded. After 10 hours the reaction was cooled to room temperature and the solvents removed under reduced pressure until the product precipitated out of solution. The remainder of the solvent was decanted off and the macrocycle dried under vacuum. The dark red product was used without further purification (90–100%): mp 181° C.-dec; ¹H NMR (CD₃OD, 300 MHz): δ1.11 (6H, t, $CH_2CH_3$), 1.76 (4H, p, pyrrole-$CH_2CH_2CH_2OH$), 2.03 (4H, p, $OCH_2CH_2CH_2OH$), 2.36 (6H, s, pyrrole-$CH_3$), 2.46 (4H, q, $CH_2CH_3$), 2.64 (4H, t, pyrrole-$CH_2CH_2CH_2OH$), 3.61 (4H, t, pyrrole-$CH_2CH_2CH_2OH$), 3.77 (4H, t, $OCH_2CH_2CH_2OH$), 4.10 (4H, s, (pyrrole)₂—$CH_2$), 4.22 (4H, t, $OCH_2CH_2CH_2OH$), 7.41 (2H, s, aromatic), 8.30 (2H, s, CHN); ¹³C NMR (CD₃OD, 300 MHz): δ9.96, 17.17, 18.65, 20.89, 24.52, 33.15, 33.45, 59.58, 61.93, 67.82, 107.11, 120.66, 123.76, 124.98, 125.80, 128.68, 144.80, 144.96, 150.72, 154.60; FAB MS (M+H)⁺ 703; HRMS M⁺ 701.4120 (calc for $C_{40}H_{55}N_5O_6$, 701.4152).

Gadolinium (III) complex of 4,5-diethyl-10,23-dimethyl-9,24-bis(3-hydroxypropyl)-16,17-(3-hydroxypropyloxy)-13,20,25,26,27-pentaazapentacyclo[20.2.1.1³,⁶.1⁸,¹¹.0¹⁴,¹⁹] heptacosa-1,3,7,9,11(27),12,14(19),15,17,20,22(25),23-tridecaene. $7_K$. FIG. 7. [GdB2T2Txp]. A-mixture of 4,5-diethyl-10,23-dimethyl-9,24-bis(3-hydroxypropyl)-16,17-bis(3-hydroxypropyloxy)-13,20,25,26,27-pentaazapentacyclo [20.2.1.1³,⁶.1⁸,¹¹.0¹⁴,¹⁹]heptacosa-3,5,8,10,12,14(19),15,17,20, 22,24-undecaene $7_J$ (1.52 g, 0.002 mol), gadolinium (III) acetate tetrahydrate (2.64 g, 0.007 mol), and triethylamine (ca. 1 mL) in 2 L of methanol was heated to reflux under air for 3.5–4 hours. The dark green reaction was cooled to room temperature and the solvent removed under reduced pressure. Dichloromethane, containing 2% methanol, was added to the resulting green solid to form a slurry and was filtered to wash away some red colored impurities (incomplete oxidation products). The complex was then washed through the filter with methanol to leave behind some excess gadolinium salts on the filter. The methanol was reduced to a small volume on a rotary evaporator and then a small amount of silica gel was added. The rest of the methanol was removed carefully under reduced pressure and the complex/silica gel mixture dried under vacuum for several hours. The silica mixture was placed on top of a silica gel column and eluted with CHCl₃ containing increasing concentrations of methanol (5–100%). Fractions containing the complex were collected and the solvent removed under reduced pressure. The complex was further purified by passing it through a plug of neutral alumina using 1:1 CHCl₃/methanol as the eluent. The final column was used to remove any remaining free gadolinium salts. The complex was recrystallized from methanol/diethyl ether to yield 0.92 g of dark green powder (44%): UV/vis $\lambda_{max}$ nm (CH₃OH) 414, 474, 738, (H₂O) 417, 469, 740; FAB MS (M+H)⁺,855; HRMS, (M)⁺ 854.2995 (calc for $C_{40}H_{50}N_5O_6{}^{158}Gd$, 854.3002).

Lanthanum (III) complex of 4,5-diethyl-10,23-dimethyl-9,24-bis(3-hydroxypropyl)-16,17-(3-hydroxypropyloxy)-13,20,25,26,27-pentaazapentacyclo[20.2.1.1³,⁶.1⁸,¹¹.0¹⁴,¹⁹] heptacosa-1,3,5,7,9,11(27),12,14(19),15,17,20,22(25),23-tridecaene. $7_M$. FIG. 7. [LaB2T₂Txp]. A mixture of 4,5-diethyl-10,23-dimethyl-9,24-bis(3-hydroxypropyl)-16,17-bis(3-hydroxypropyloxy)-13,20,25,26,27-pentaazapentacyclo [20.2.1.1³,⁶.1⁸,¹¹.0¹⁴,¹⁹]heptacosa-3,5,8,10,12,14(19),15,17,20, 22,24-undecaene $7_J$ (100 mg, 0.14 mmol), lanthanum (III) nitrate hexahydrate (185 mg, 0.42 mmol), and triethylamine (5 drops) in methanol (150 mL) were heated to reflux under air for 16 hours. The dark green reaction was cooled to room temperature and the solvents removed on a rotary evaporator. The complex was dissolved into methanol and filtered through a fine glass frit. A small amount of neutral alumina was added and the methanol removed under reduced pressure. The alumina/complex mixture was dried under vacuum for several hours then placed on top of a neutral alumina column. The column was eluted using neat CHCl₃ and CHCl₃ containing increasing concentrations of methanol (5–20%). Fractions containing the complex were reduced to dryness on a rotary evaporator and the resulting green solid recrystallized several times from methanol/diethyl ether. A dark green product (66 mg) was obtained (50%): UV/vis $\lambda_{max}$ nm (CH₃OH) 417, 476, 746; FAB MS (M+H)⁺, 836; HRMS (M+H)⁺, 836.2886 (calc for $C_{40}H_{51}N_5O_6{}^{139}La$, 836.2903).

EXAMPLE 5

Figure 8:
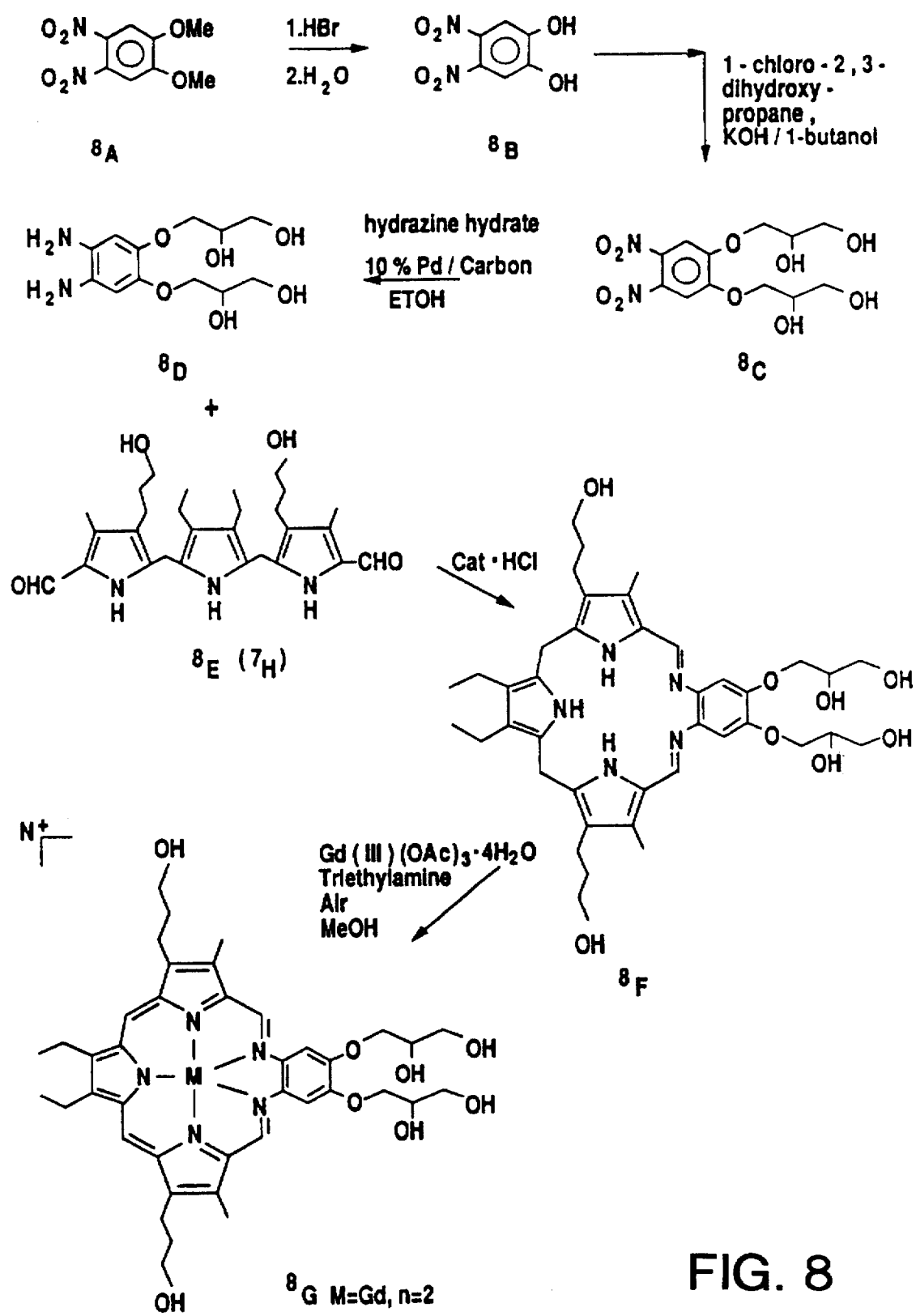
FIG. 8 schematically summarizes the synthesis of B4T$_2$TXP($8_F$) and [Gd B4T2 TXP]$^{2+}$ ($8_G$), compounds of the present invention. Compound $8_D$ is claimed as an intermediate in the synthesis of B4T2TXP in the present invention.

Synthesis of B4T2 TXP 1,2-Dihydroxy-4,5-dinitrobenzene. $8_B$. FIG. 8. In a dry 500 mL round bottom flask, 1,2-dimethoxy-4,5-dinitrobenzene (3.2 g, 0.12 mmol) $8_A$ was stirred vigorously in 40 mL of glacial acetic acid at 30° C. Once a homogeneous solution 200 mL of 48% HBr was added to the flask and the reaction was slowly heated to reflux. The reaction was complete as indicated by TLC after 4 hours. The work up involved pouring the cooled solution into 800 mL of ice water and then extracting the aqueous phase with CHCl₃ (3×150 mL) in order to remove any organic impurities. The dinitro catechol was extracted out of the aqueous layer with ethyl acetate (3×150 mL). The combined ethyl acetate extracts were washed with water and brine (3×100 mL), then dried over $MgSO_4$ and concentrated to an orange residue. Approximately 100 mL of dichloromethane was added to the residue and then placed in the freezer for several hours. The light yellow needles that formed were filtered and washed with dichloromethane to yield 2.37 g of product (84%). $^1$H NMR ($d_6$-acetone): δ3.45 (OH), 7.42 (Ar—H); $^{13}$C NMR ($d_6$-acetone): δ112.44, 137.00, 149.97, EI MS M$^+$, 200.

1,2-Bis(2,3-dihydroxypropyloxy)-4,5-dinitrobenzene. $8_C$, FIG. 8. 1,2-Dihydroxy-4,5-dinitrobenzene $8_B$ (5.0 g, 22 mmol) and 1-chloro-2,3-dihydroxypropane (12.1 g, 110 mmol) were refluxed for 48 hours in a solution of potassium hydroxide (4.4 g) in 1-butanol (100 mL) under a nitrogen atmosphere. The resulting mixture was concentrated under reduced pressure, and the dark residue was partitioned between 100 mL of THF and 100 mL of brine/50 mL water solution in a 500 mL separatory funnel. The mixture was allowed to separate and the aqueous phase was extracted with THF (2×100 mL). The combined THF extracts were washed with brine (2×50 mL), dried over $MgSO_4$ and concentrated to an oily residue. Here, $CH_2Cl_2$ was added very carefully to insure precipitation of the crude product. After stirring for 15 minutes, the suspension was filtered with a medium glass fritted funnel and air dried for several minutes. The orange solid was taken up in 120 mL of $CHCl_3$ and 80 mL of diethyl ether at reflux and hot filtered to remove some impurities. The crude product was dissolved in a mixture of acetone and methanol (sonication may be required), then 6 grams of deactivated silica gel was added to the orange solution. The slurry was concentrated to dryness and the orange solid was dried in vacuo for one hour. The orange solid was loaded on a packed deactivated silica gel column. The column was eluted starting with neat $CHCl_3$ followed by $CHCl_3$ with increasing concentration of methanol (0–10%). After a bright yellow impurity (monoalkylated product) was removed a colorless product began to elute (using 8–10% methanol in $CHCl_3$ eluents). Conversely, on TLC the product will elute faster than the bright yellow monoalkylated product. The purified dialkylated tetrahydroxy product can be recrystallized from acetone/diethyl ether to yield 2.60 grams (30%) of a light yellow fluffy solid. $^1$H NMR ($d_6$-acetone): δ2.95 (bs, 4H, OH), 3.69 (d, 4H, OC$H_2$CH(OH)CH$_2$OH), 4.06 (p, 2H, OCH$_2$C$\underline{H}$(OH)CH$_2$OH), 4.24–4.35 (m, 4H, OCH$_2$CH(OH)C$\underline{H}_2$OH), 7.72 (s, 2H, Ar—H); $^{13}$C NMR ($d_6$-acetone): δ63.55, 70.89, 72.53, 109.99, 137.22, 152.77. CI MS 349.

1,2-Diamino-4,5-bis((2,3-dihydroxypropyl)oxy)benzene. $8_D$, FIG. 8. The diamine was obtained by reduction of the corresponding 1,2-bis((2,3-dihydroxypropyl)oxy)-4,5-dinitrobenzene (0.30 g, 0.86 mmol) with hydrazine hydrate (1 mL) and 10% palladium on carbon (50 mg) in 40 mL refluxing absolute ethanol. The resulting brown suspension bubbled for approximately 15–20 minutes and then turned colorless after 1 hour. At this point the reduction was deemed complete as judged by TLC (Rf=0.63, 100% methanol). The reaction solution was hot filtered through celite into a dry flask, covered with aluminum foil, and then concentrated to a light yellowish oil. The diamine was taken to the next step without further purification. For B4 diamine: $^1$H NMR (CD$_3$OD): δ3.54–3.58 (m, 4H, OC$\underline{H}_2$CH(OH)CH$_2$OH), 3.80–3.85 (m, 6H, OCH$_2$C$\underline{H}$(OH)C$\underline{H}_2$OH), 6.39 (s, 2H, Ar—H); $^{13}$C NMR (CD$_3$OD): δ64.27, 71.88, 73.22, 107.61, 130.31, 143.74.

4,5-Diethyl-9,24-bis(3-hydroxypropyl)-16,17-bis((2,3-dihydroxypropyl)oxy)-10,23-dimethyl-13,20,25,26,27-pentaazapentacyclo[20.2.1.1$^{3,6}$.1$^{8,11}$.0$^{14,19}$]heptacosa-3,5,8, 10,12,14(19),15,17,20,22,24-undecaene. [sp$^3$ B4T2 TXP] $8_F$, FIG. 8. 2,5-Bis[(5-formyl-3-hydroxypropyl-4-methylpyrrol-2-yl)methyl]-3,4-diethylpyrrole (336 mg, 0.70 mmol) and 1,2-diamino-4,5-bis((2,3-dihydroxypropyl)oxy) benzene (ca 223 mg, 0.77 mmol) were placed in a 1 L round bottom flask with 600 mL of toluene and 175 mL of methanol. The solvents were purged with nitrogen prior to use. Concentrated HCl (ca 3 drops) was added and the reaction heated to reflux under nitrogen. After one hour the reaction was cooled to room temperature and the solvent removed under reduced pressure until the dark brown product precipitated. The remainder of the solvent was decanted off and the product dried in vacuo. The product was used in the next step without further purification.

Gadolinium (III) complex of 4,5-Diethyl-9,24-bis(3-hydroxypropyl)-16,17-bis((2,3-dihydroxypropyl)oxy)-10,23-dimethyl-13,20,25,26,27-pentaazapentacyclo[20.2.1.1$^{3,6}$.1$^{8,11}$.0$^{14,19}$]heptacosa-1,3,5,7,9,11(27),12,14(19),15,17,20,22(25),23-tridecaene [GdB4T2Txp]. $8_G$, FIG. 8. Two identical reactions containing a mixture of reduced B4T2 texaphyrin ligand, 4,5-Diethyl-9,24-bis(3-hydroxypropyl)-16,17-bis((2,3-dihydroxypropyl)oxy)-10,23-dimethyl-13, 20,25,26,27-pentaazapentacyclo[20.2.1.1$^{3,6}$.1$^{8,11}$.0$^{14,19}$] heptacosa-3,5,8,10,12,14(19),15,17,20,22,24-undecaene, (0.75 g, 0.001 mol), gadolinium (III) acetate tetrahydrate (1.19 g, 0.003 mol), and triethylamine (ca 1 mL) were heated at reflux under air in 750 mL of absolute methanol. After heating for 17 hours the reactions were cooled slightly and air bubbled through the reaction mixture for several minutes. The reactions were then heated to reflux again. After heating for a total of 21 hours the reactions were cooled to room temperature, the solvent removed on a rotary evaporator, and the dark green products combined and dried in vacuo for several hours. The metal complex was dissolved into 100 mL of methanol and 6–8 grams of deactivated silica gel was added. (The silica gel was deactivated by adding a mixture of 6 mL water in 20 mL of methanol to 100 g of silica gel. After thorough mixing, the silica gel was allowed to air dry for 12 hours before bottling). The solvent was carefully removed on a rotary evaporator and the silica/complex mixture dried in vacuo for one hour. The complex was loaded onto a prepacked column of deactivated silica gel (5 cm length×3.5 cm diameter) and eluted with chloroform containing increasing amounts of methanol (0–80%). Fractions containing the complex were collected and concentrated to dryness. The green complex was further purified by recrystallization from methanol/anhydrous ethyl ether. 480 mg of product was obtained from the two combined reactions (25%). For the complex: UV/vis. $\lambda_{max}$. nm (CH$_3$OH) 415, 474, 740; FAB MS (M+H)$^+$, 887; HRMS (M+H)$^+$, 887.2977 (calc for C$_{40}$H$_{51}$N$_5$O$_8^{158}$Gd, 887.2981).

EXAMPLE 6
Further derivatives of Texaphyrin

Intermediates hydroxylated in various positions can be combined to effect the synthesis of a number of compounds. For example, the B4 TXP derivative is synthesized by reacting the intermediate compound $6_E$ from FIG. 6 with compound $8_D$ of FIG. 8. This constructs a molecule without hydroxyl groups on the tripyrrole moiety but with 4 hydroxyl groups on the benzene ring moiety.

The molecule T2 TXP is synthesized by reacting intermediate $7_H$ in FIG. 7 with 4,5-dimethyl-1,2-phenylenediamine to yield a texaphyrin derivative with two hydroxyls on the tripyrrole portion of the molecule and no hydroxyl substituents on the benzene ring.

A heptahydroxylated target B4T3 TXP is obtained by using the appropriate derivative 3-hydroxypropyl-4- methylpyrrole of the pyrrole (structure $7_B$ of FIG. 7) to make the trihydroxylated tripyrrole precursor which is then reacted with compound $8_D$ of FIG. 8.

Figure 11A:
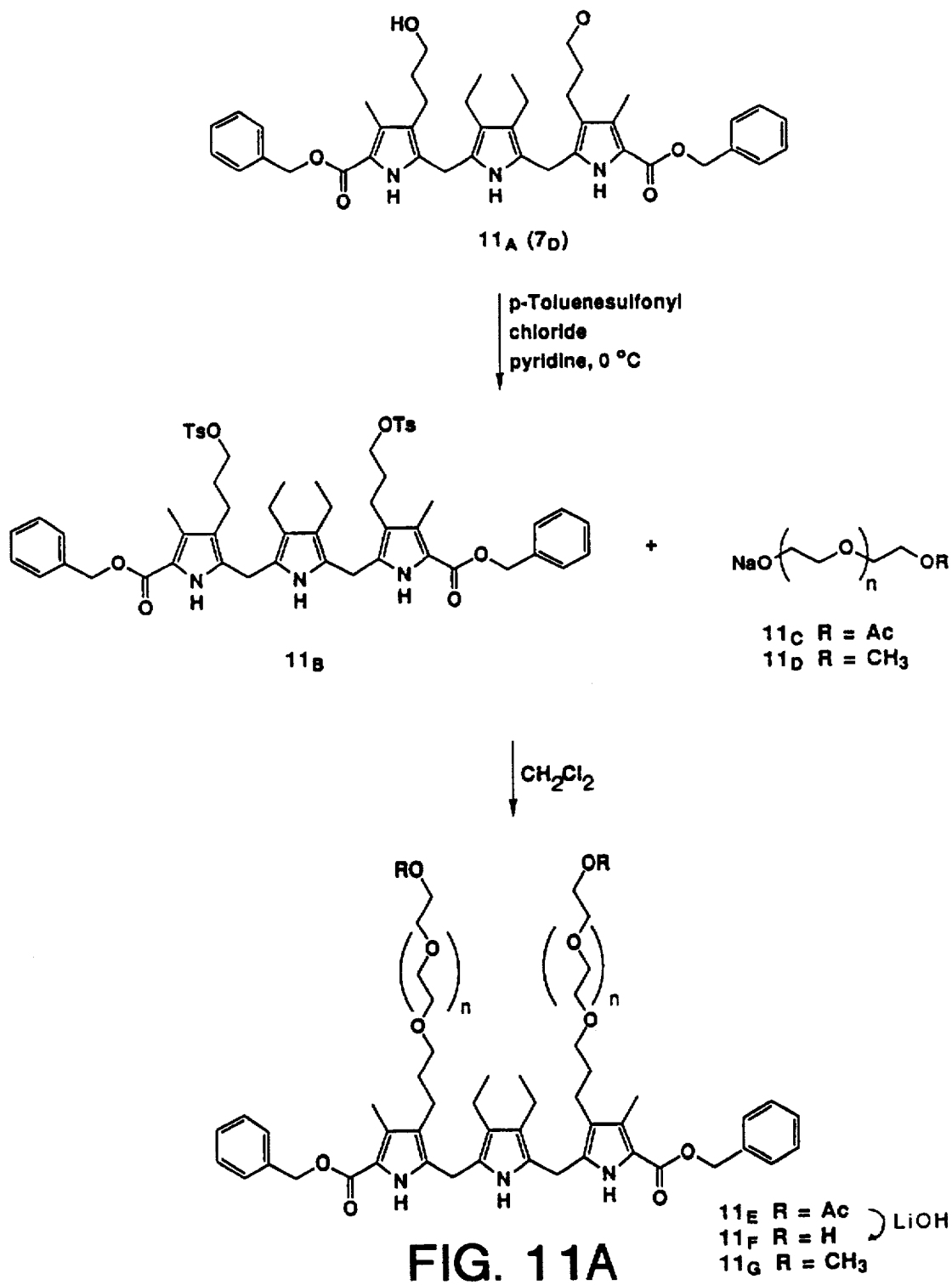
FIG. 11 summarizes the synthesis of polyether-linked polyhydroxylated texaphyrins. Ts is a tosyl group.
Figure 11B:
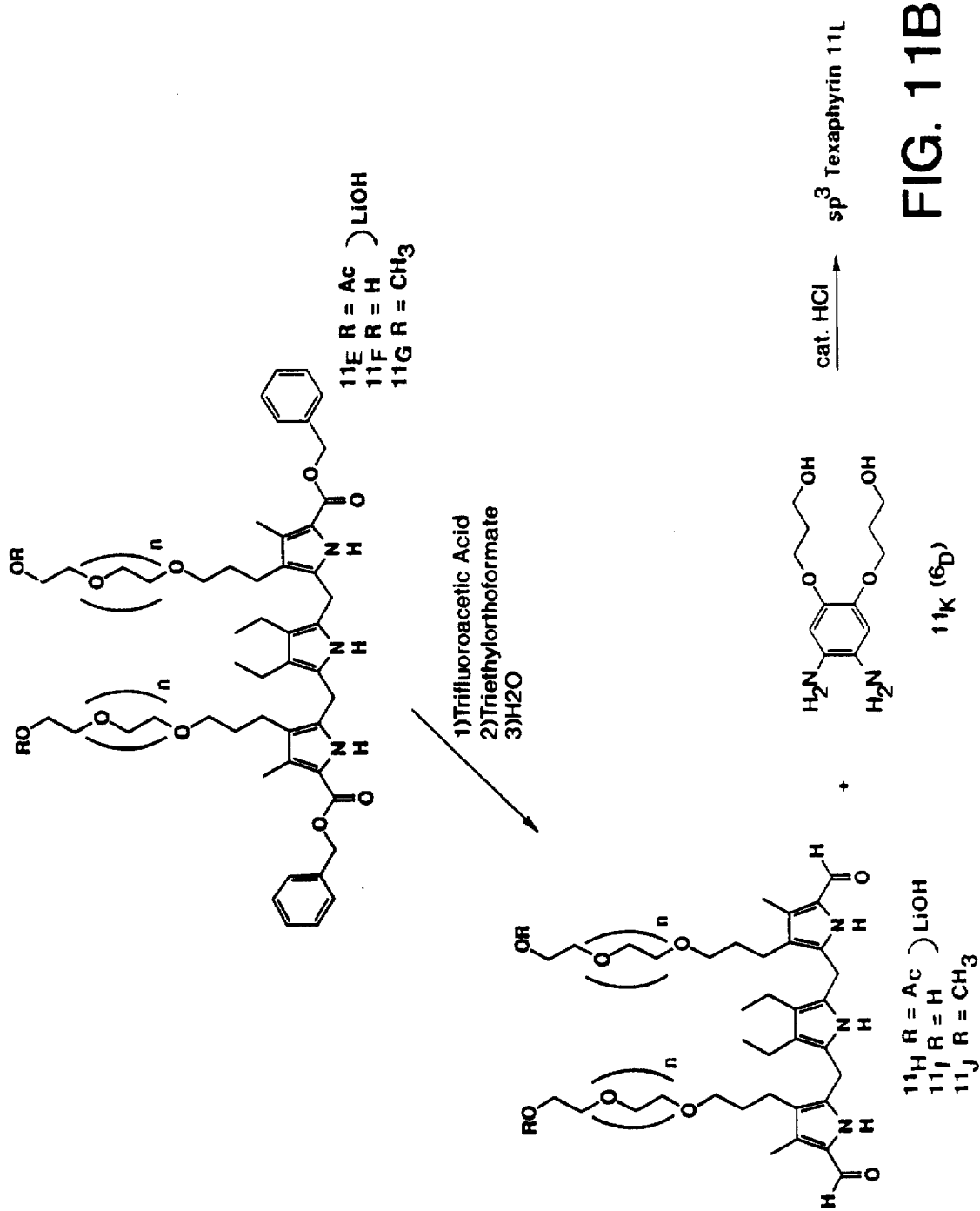
Figure 11C:
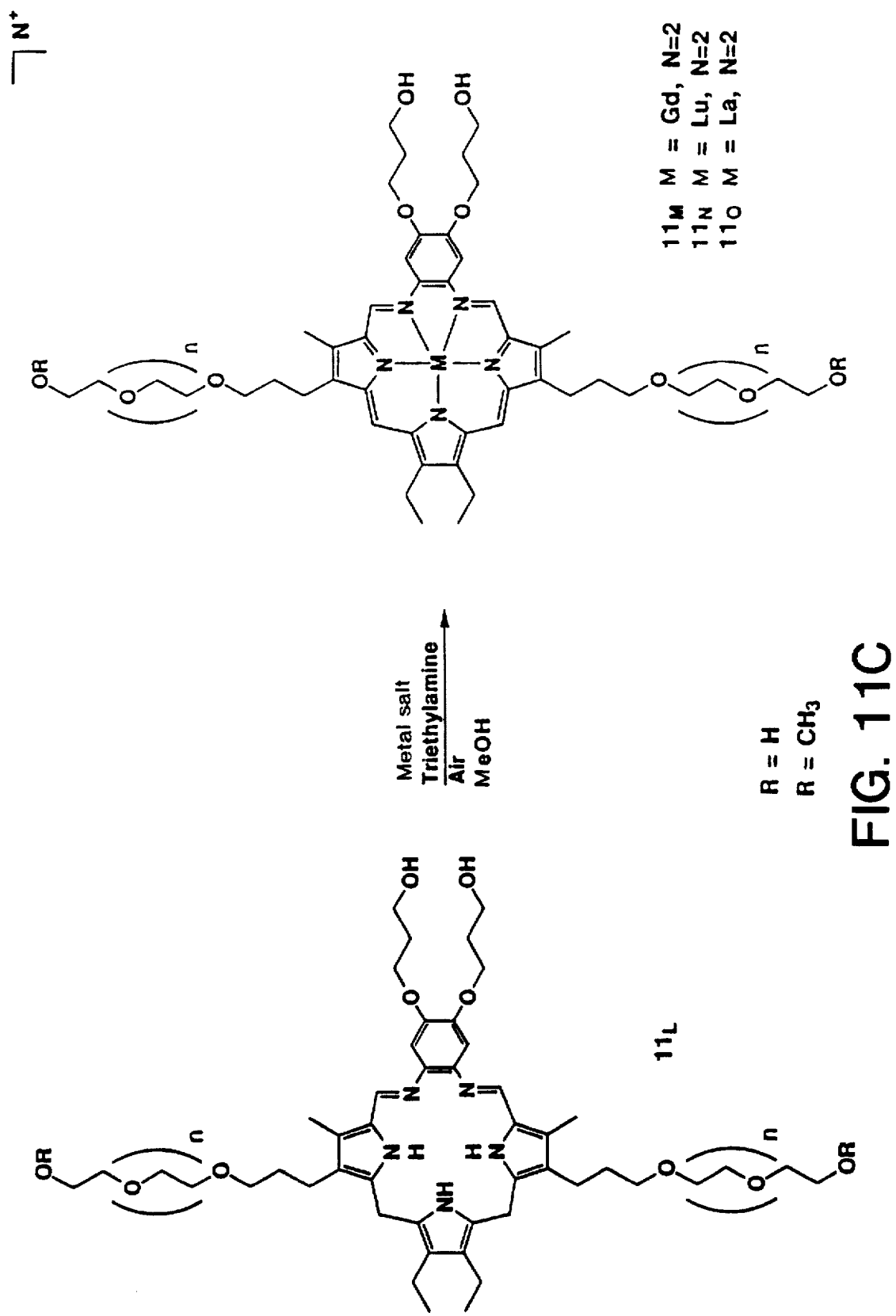
Figure 12:
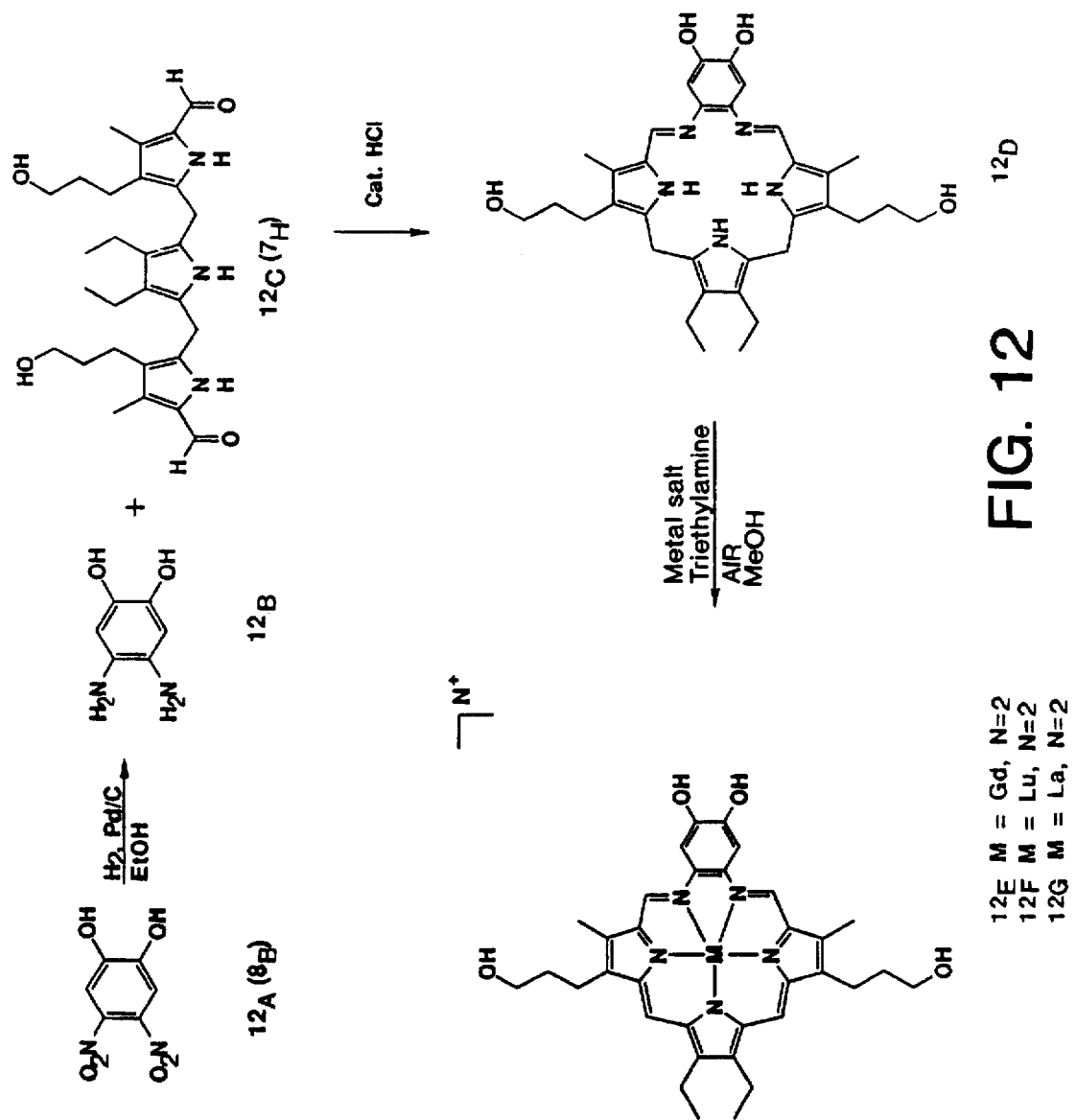
FIG. 12 summarizes the synthesis of catechol (i.e. benzene diol) texaphyrin derivatives bearing further hydroxyalkyl substituents off the tripyrrane-derived portion of the macrocycle.
Figure 13:
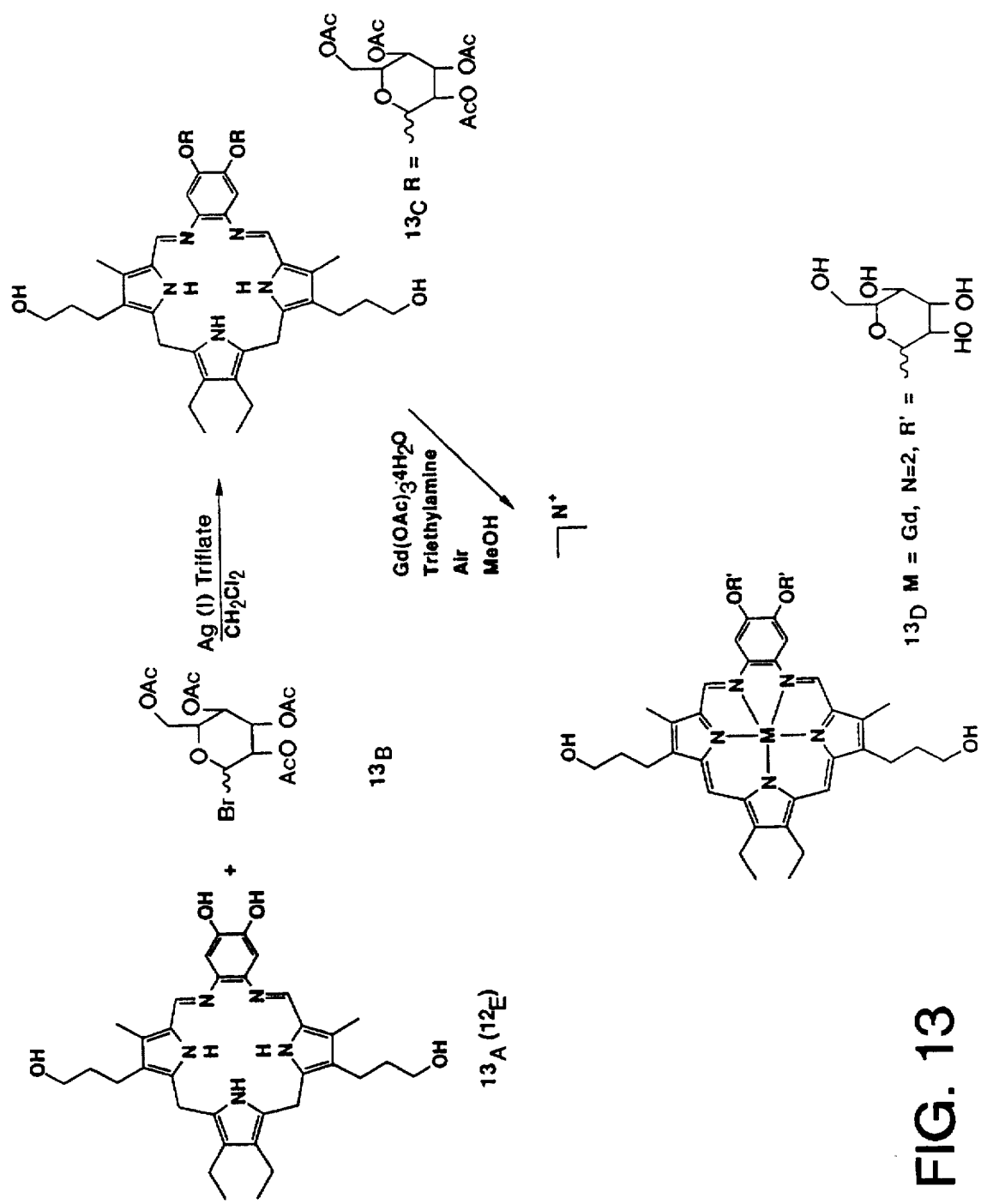
FIG. 13 provides an example of a saccharide substituted texaphyrin in which the saccharide is appended via an acetal-like glycosidic linkage. Triflate is trifluoromethanesulfonate.
Figure 14:
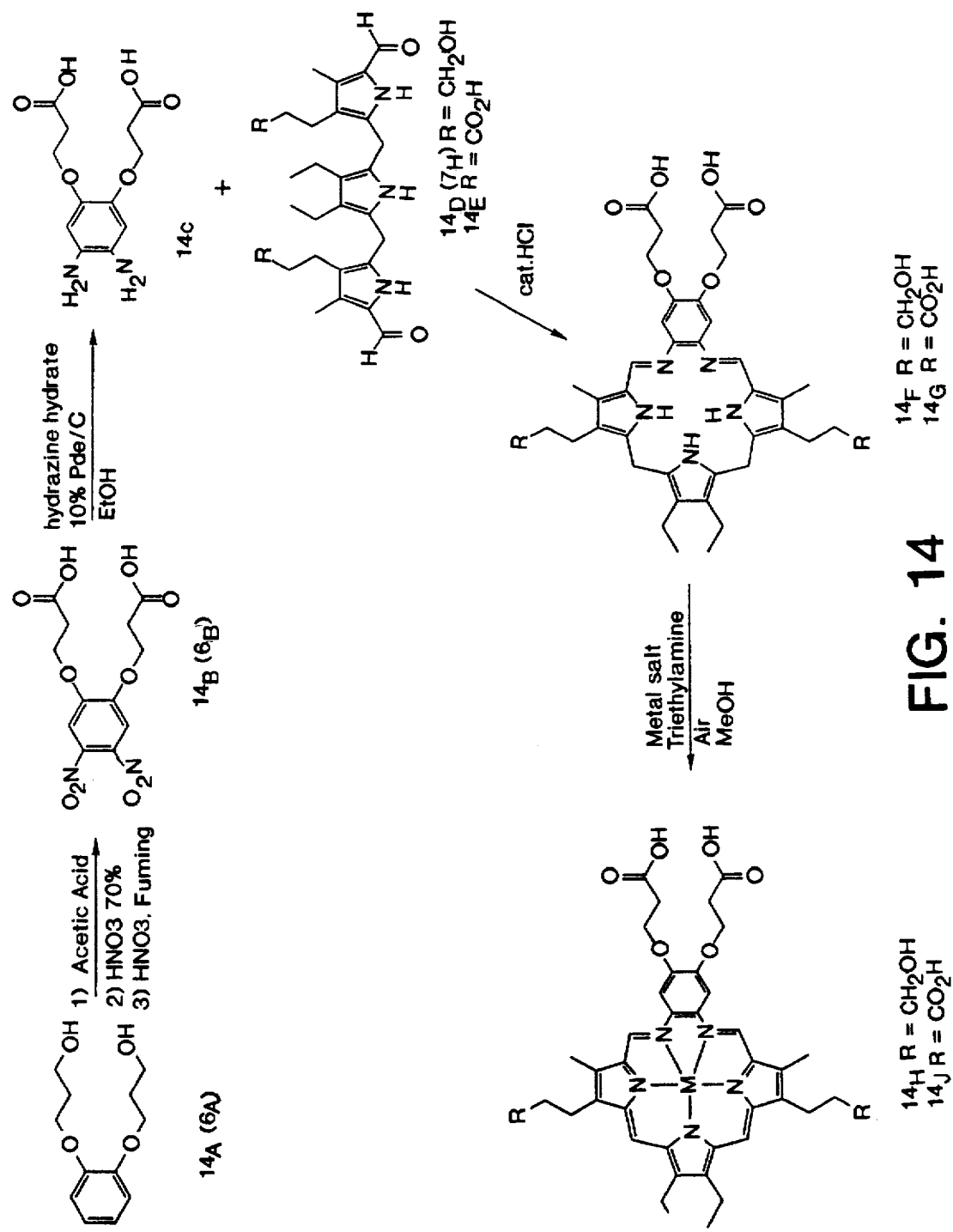
FIG. 14 summarizes the synthesis of a doubly carboxylated texaphyrin system in which the carboxyl groups are linked to the texaphyrin core via aryl ethers or functionalized alkyl substituents. The products of this scheme, compounds $14_H$ and $14_J$, could be converted on to various esterified products wherein the ester linkages serve to append further hydroxyl-containing substituents.
Figure 15A:
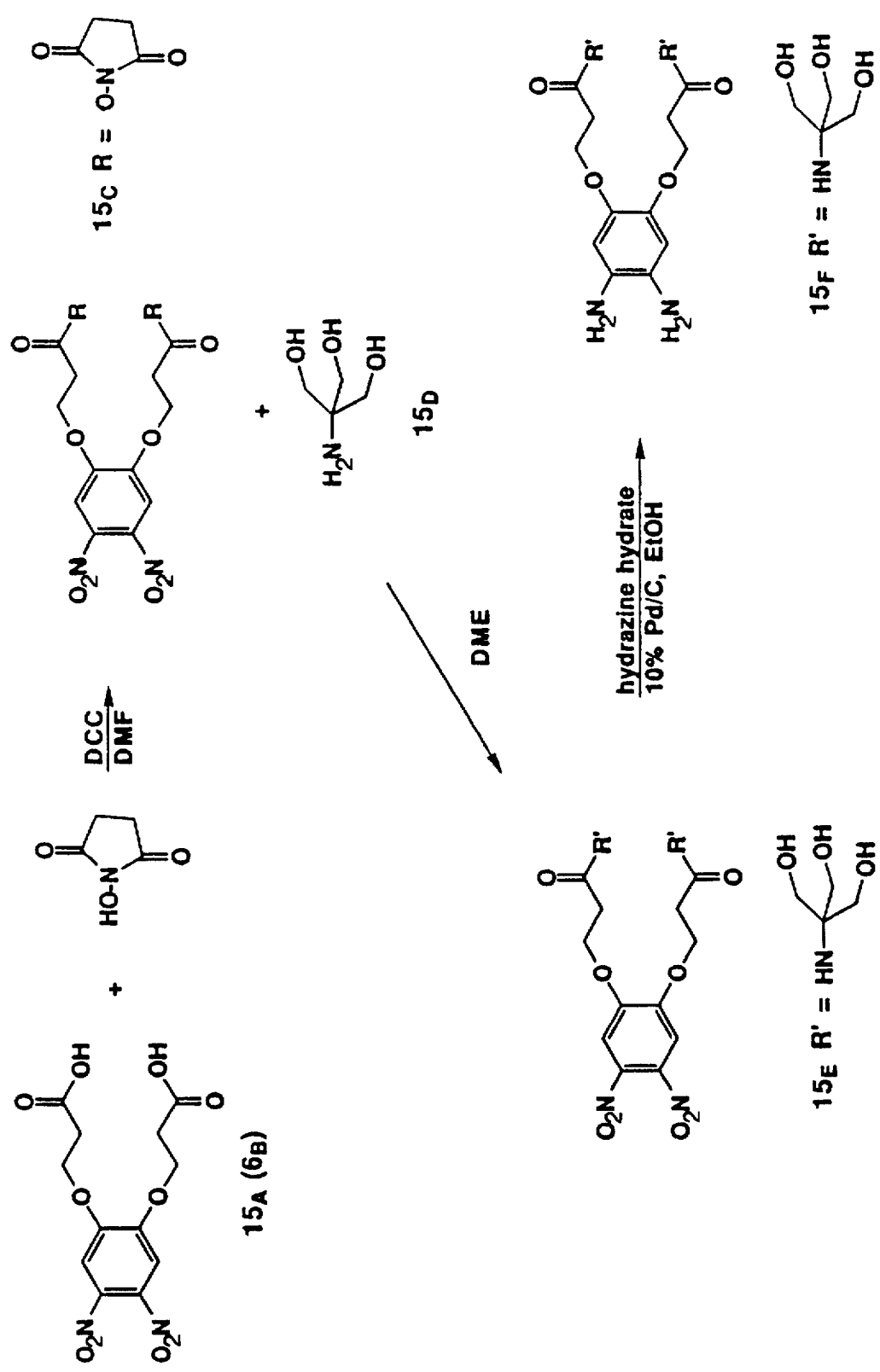
FIG. 15 summarizes the synthesis of polyhydroxylated texaphyrin derivatives via the use of secondary amide linkages. DCC is dicyclohexylcarbodiimide. DMF is dimethylformamide, and DME is dimethoxyethane.
Figure 15B:
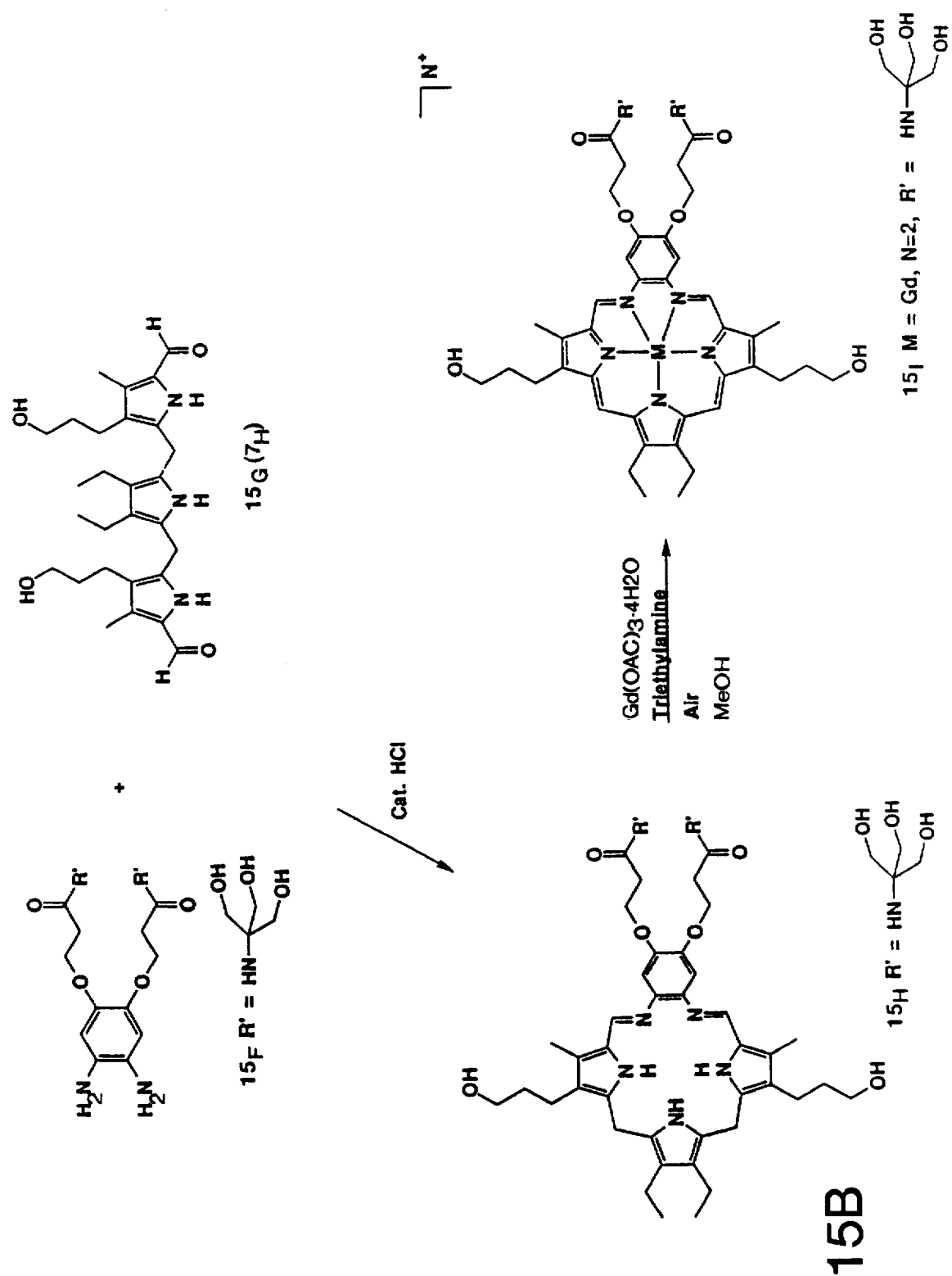
Figure 16A:
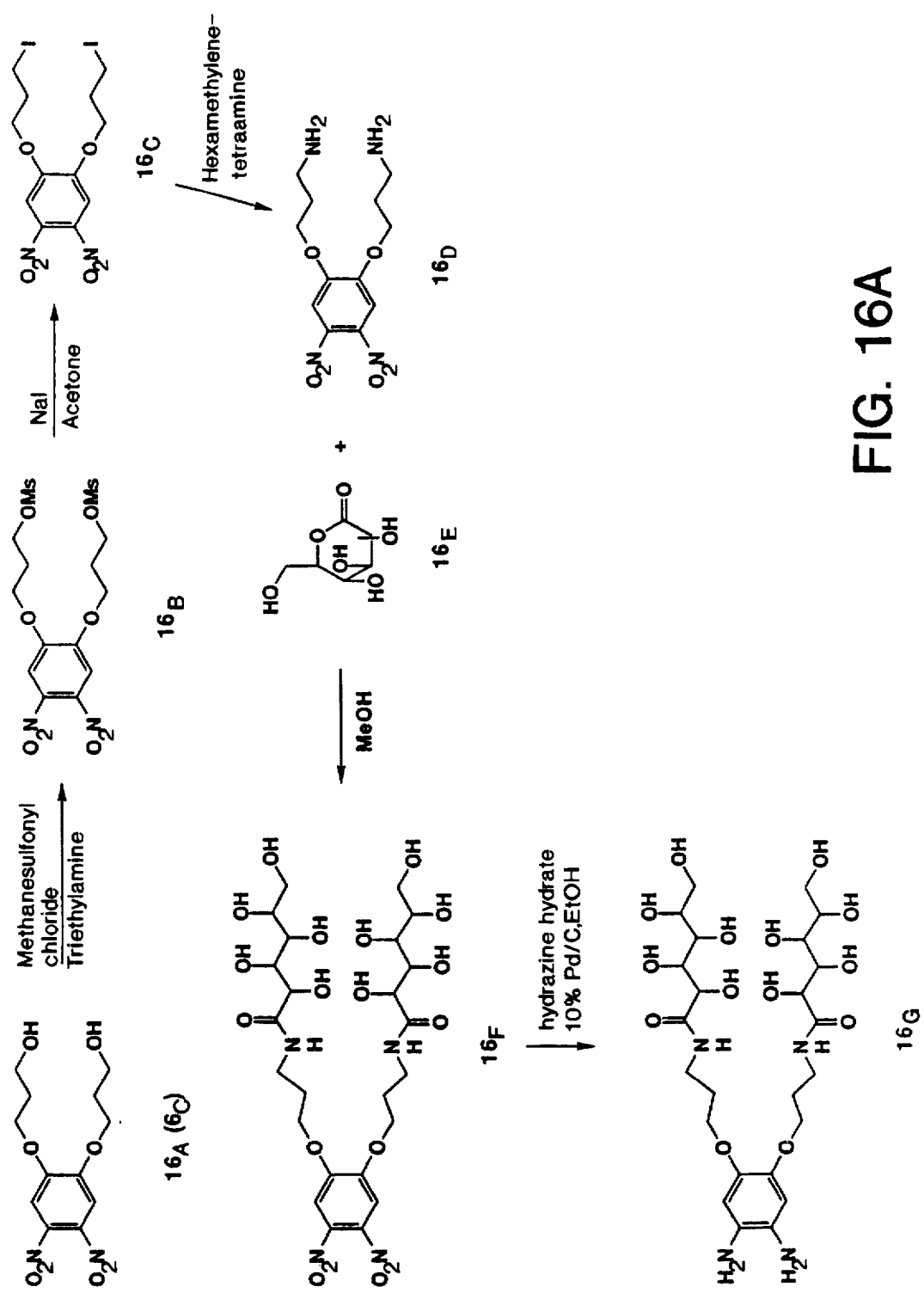
FIG. 16 summarizes the synthesis of another set of polyhydroxyl substituted texaphyrin derivatives using similar amide bonds as in FIG. 15.
Figure 16B:
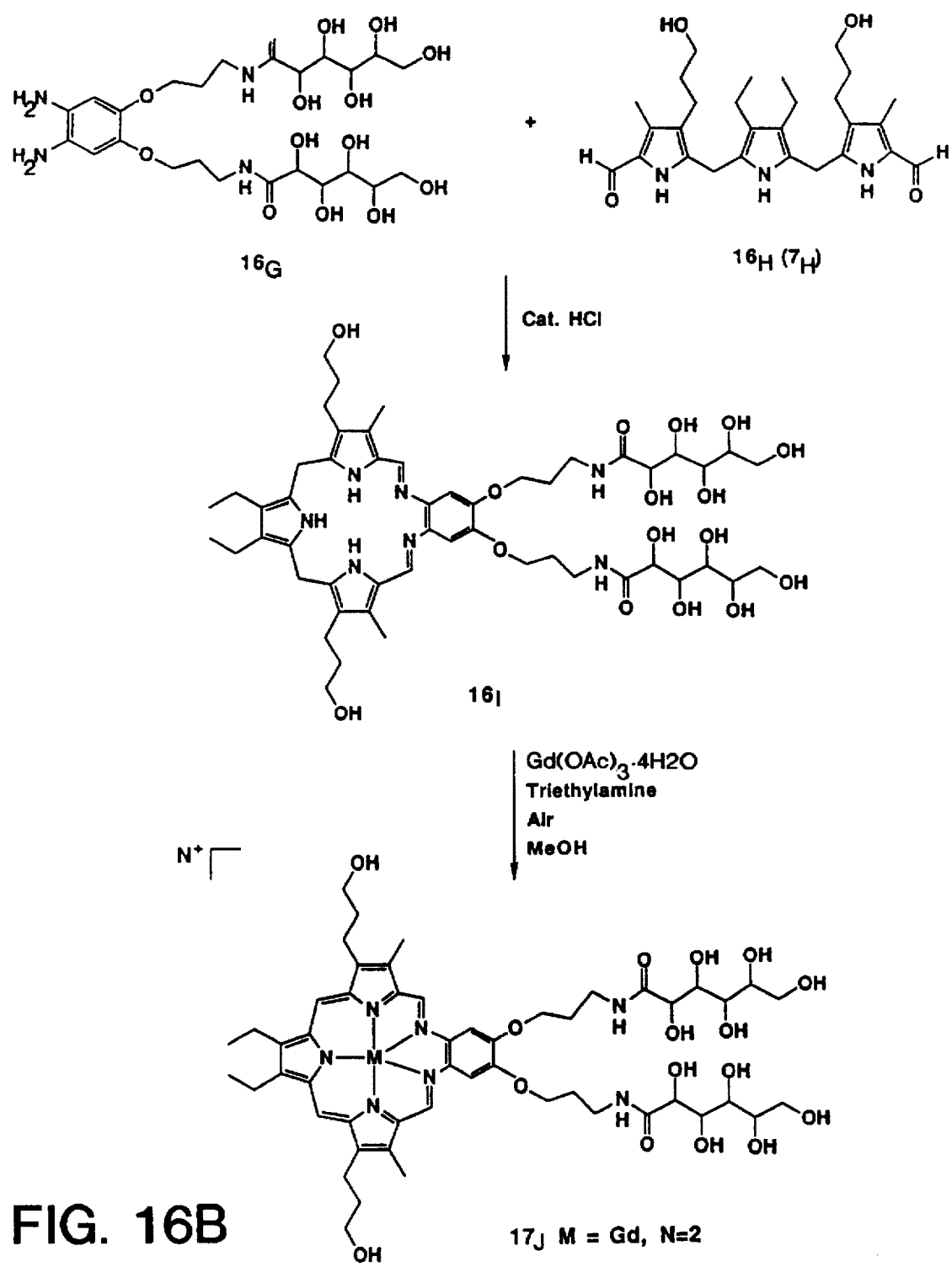
Figure 17A:
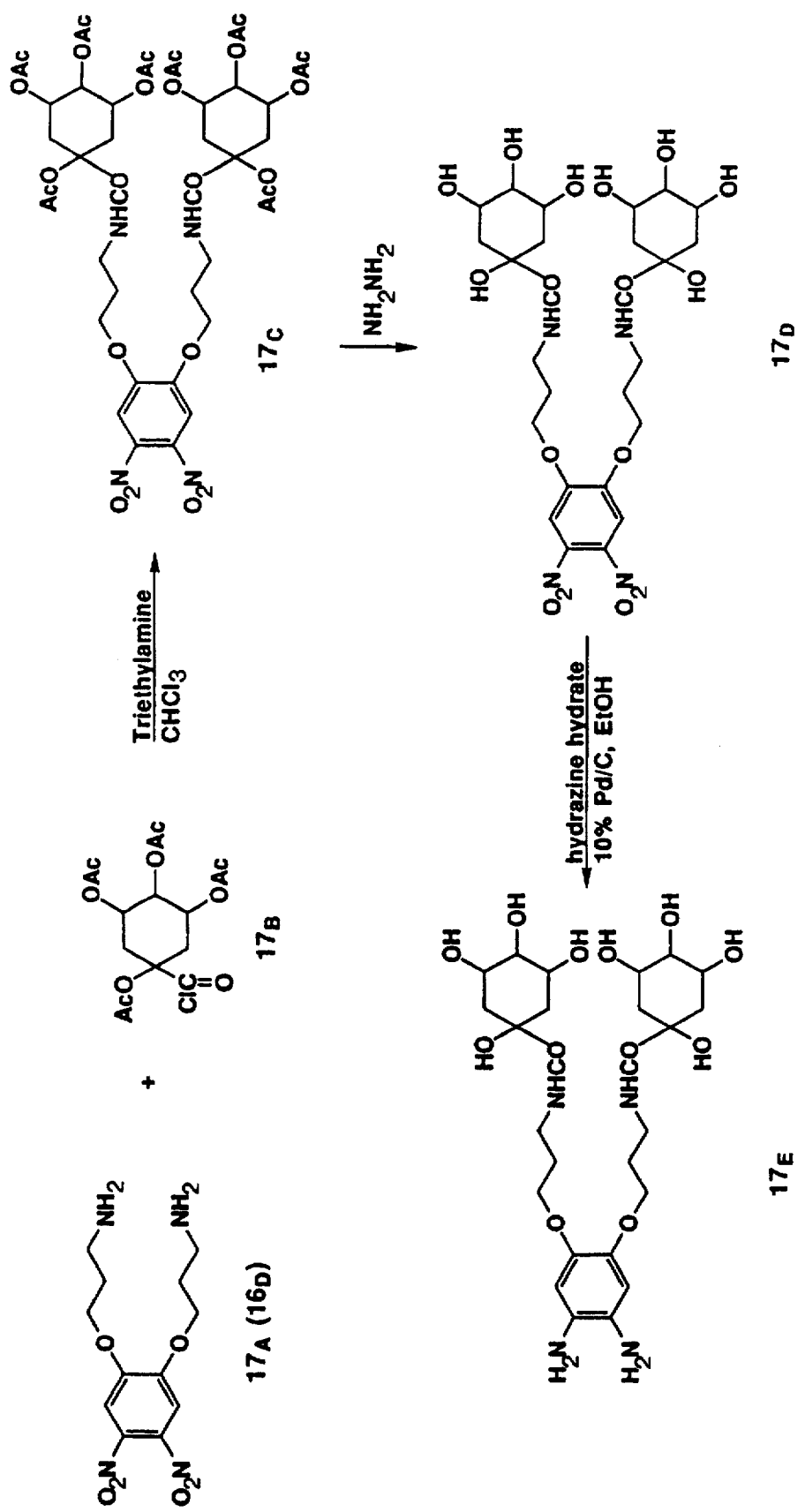
FIG. 17 summarizes the synthesis of saccharide substituted texaphyrins, wherein the saccharide moieties are appended via amide bonds.
Figure 17B:
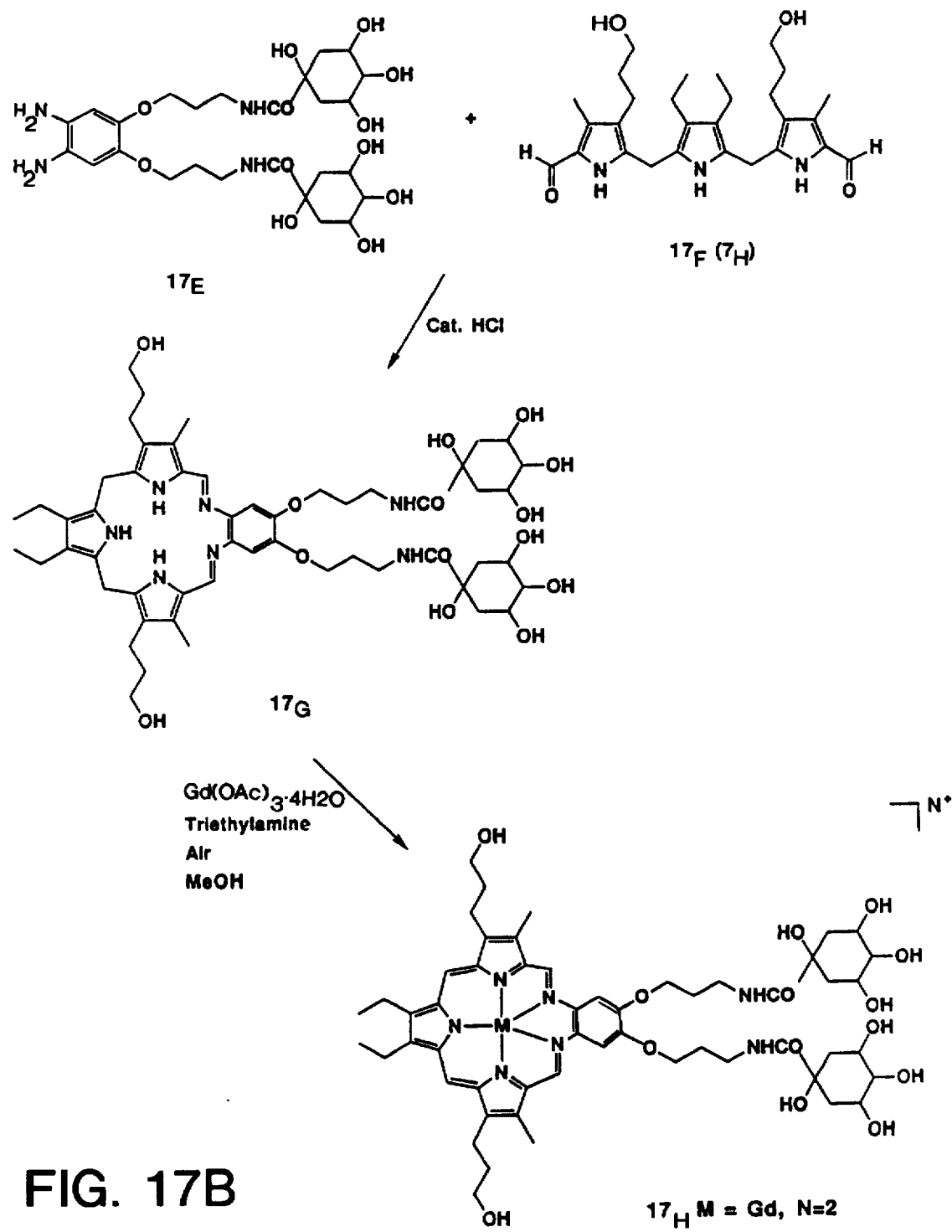
Figure 18:
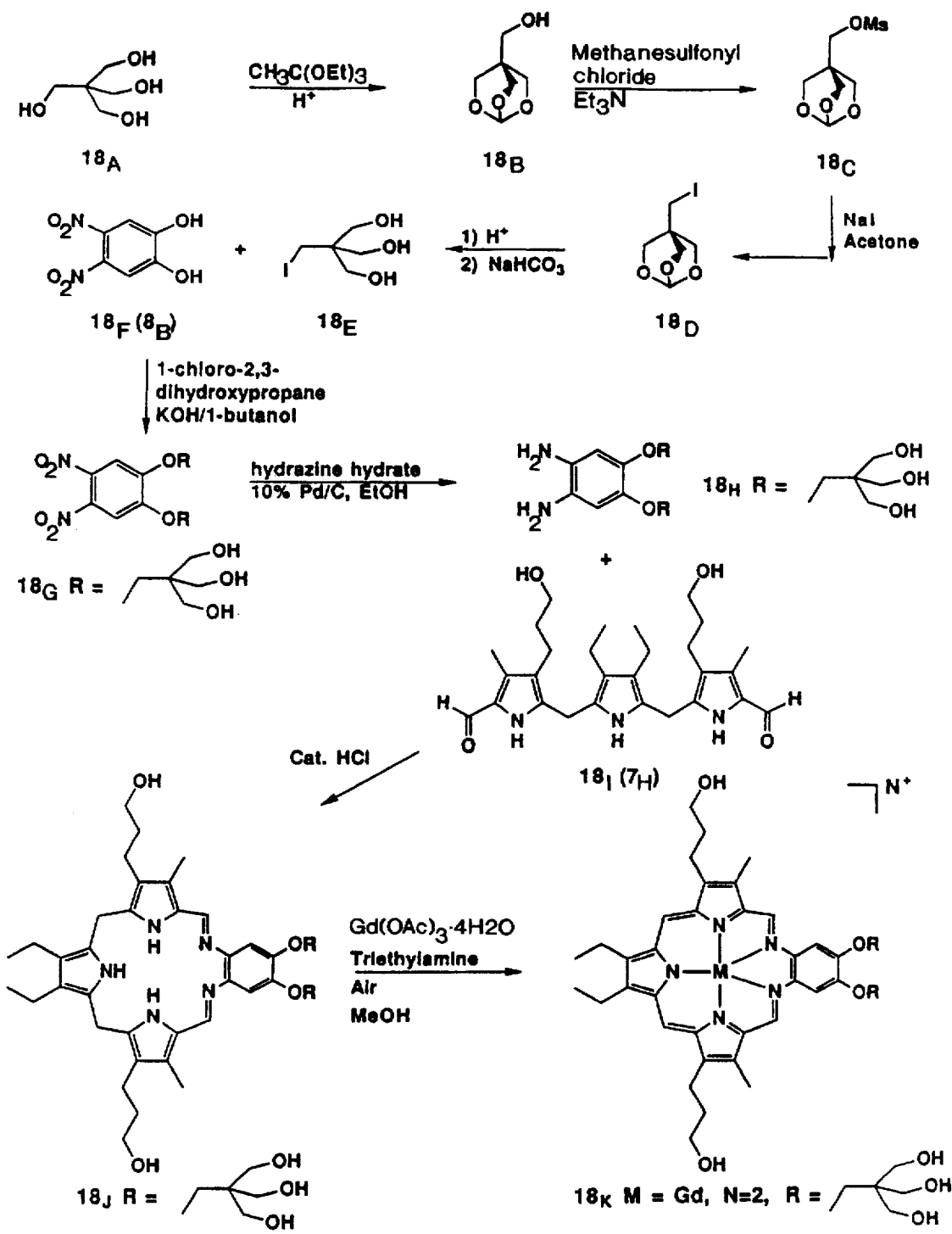
FIG. 18 summarizes the synthesis of polyhydroxylated texaphyrin derivatives containing branched polyhydroxyl (polyol) subunits appended to the texaphyrin core via aryl ethers.
Figure 19A:
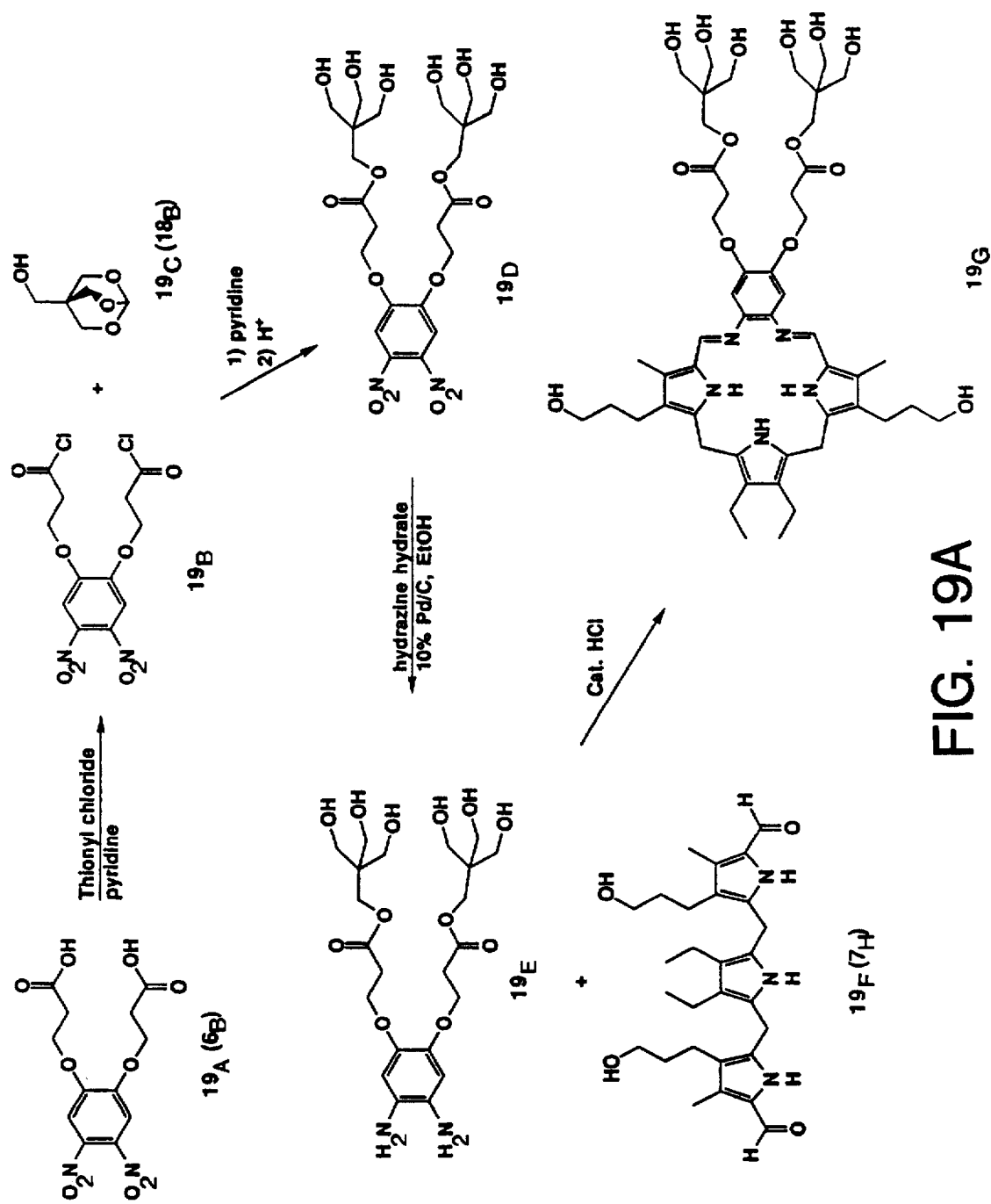
FIG. 19 summarizes how similar polyol subunits may be appended via ester linkages.
Figure 19B:
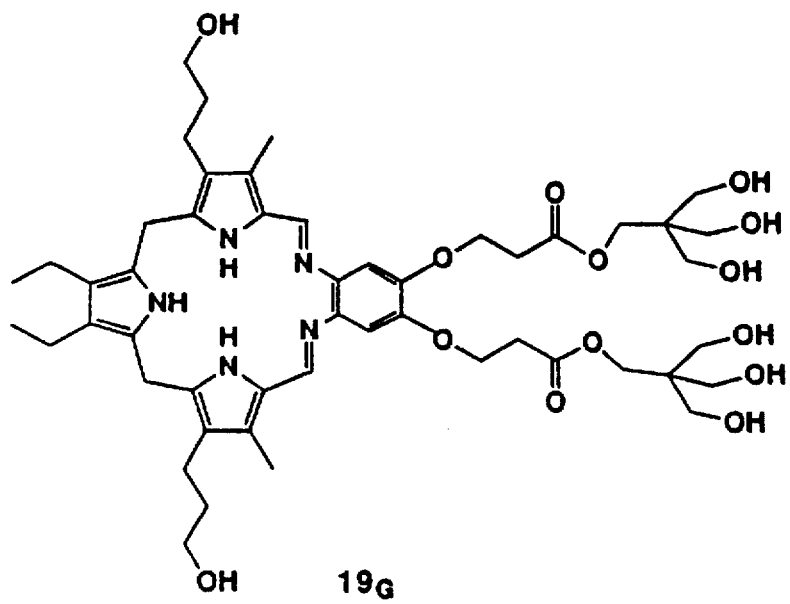
Figure 19B:
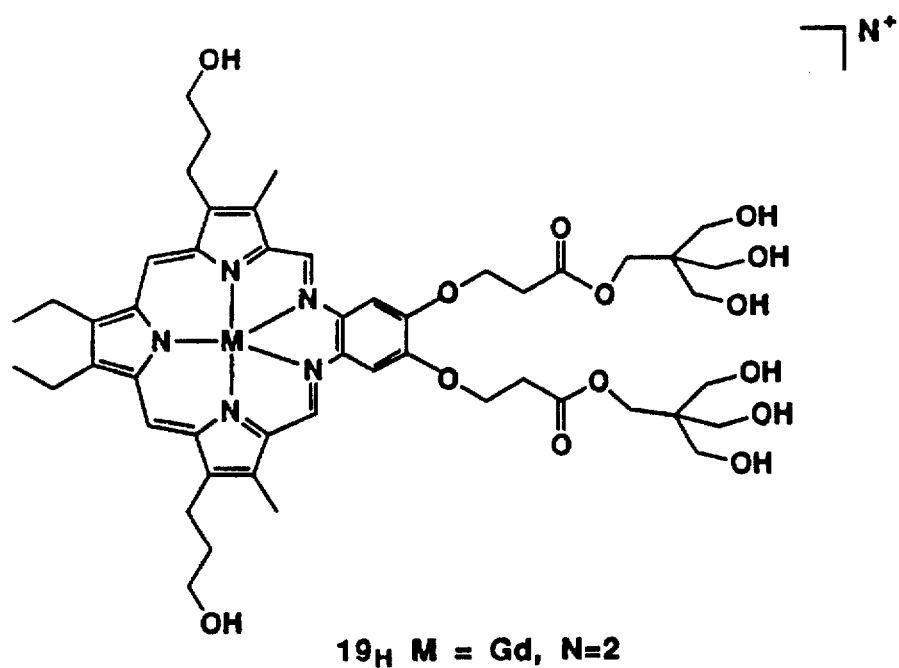

FIGS. 11-19 provide specific examples of how one skilled in the art could extend and refine the basic synthetic chemistry outlined in this application so as to produce other hydroxylated texaphyrins equivalent in basic utility to those specifically detailed in the examples. FIG. 11 summarizes the synthesis of polyether-linked polyhydroxylated texaphyrins. FIG. 12 summarizes the synthesis of catechol (i.e. benzene diol) texaphyrin derivatives bearing further hydroxyalkyl substituents off the tripyrrane-derived portion of the macrocycle. FIG. 13 provides an example of a saccharide substituted texaphyrin in which the saccharide is appended via an acetal-like glycosidic linkage. FIG. 14 summarizes the synthesis of a doubly carboxylated texaphyrin system in which the carboxyl groups are linked to the texaphyrin core via aryl ethers or functionalized alkyl substituents. The products of this scheme, compounds $14_H$ and $14_I$ could be converted to various esterified products wherein the ester linkages serve to append further hydroxyl-containing substituents. FIG. 15 summarizes the synthesis of polyhydroxylated texaphyrin derivatives via the use of secondary amide linkages. FIG. 16 summarizes the synthesis of another set of polyhydroxyl substituted texaphyrin derivatives using similar amide bonds as in FIG. 15. FIG. 17 summarizes the synthesis of saccharide substituted texaphyrins, wherein the saccharide moieties are appended via amide bonds. FIG. 18 summarizes the synthesis of polyhydroxylated texaphyrin derivatives containing branched polyhydroxyl (polyol) subunits appended to the texaphyrin core via aryl ethers. FIG. 19 summarizes how similar polyol subunits may be appended via ester linkages.

EXAMPLE 7
Characterization of new derivatives

New texaphyrin derivatives may be characterized fully using normal spectroscopic and analytical means, including, X-ray diffraction methods. A complete analysis of the optical properties may be made for new systems under a range of experimental conditions including conditions designed to approximate those in vivo. Detailed analyses, including triplet lifetime and singlet oxygen quantum yield determinations may be made. The objective is to obtain a complete ground and excited state reactivity profile for each new texaphyrin produced. Questions such as when singlet oxygen production is maximized, how the quantum yield for its formation is influenced by the position of the lowest energy (Q-type) transition, whether aggregation is more prevalent in certain solvents or in the presence of certain biologically important components (e.g. lipids, proteins, etc.), and, finally, whether significant differences in in vitro optical properties are derived from the use of elaborated texaphyrins bearing cationic, anionic, or neutral substituents may be answered.

With newly prepared complexes, screening experiments are carried out. Standard in vitro protocols are used to evaluate the in vitro photo-killing ability of the texaphyrin derivatives in question. For instance, the texaphyrin complexes of choice may be administered in varying concentrations to a variety of cancerous cells and the rate of cell replication determined both in the presence and absence of light. Similarly, texaphyrin complexes of choice may be added to standard viral cultures and the rate of viral growth retardation determined in the presence and absence of light. A variety of solubilizing carriers will be used to augment the solubility and/or monomeric nature of the texaphyrin photosensitizers and the effect, if any, that these carriers have in adjusting the biodistribution properties of the dyes will be assessed (using primarily fluorescence spectroscopy). Appropriate control experiments are carried out with normal cells so that the intrinsic dark and light toxicity of the texaphyrins may be determined.

From a generalized set of in vitro experimental procedures, a clear picture of the photodynamic capabilities of the texaphyrin derivatives will emerge. Preliminary toxicity and stability information will result from the in vitro experiments. Particular questions of interest include the texaphyrin derivatives half life under physiological conditions, whether the nature of the central metal influences stability and whether the central cation is affecting cytotoxicity. As discussed in papers published by the present inventors,[129] it is not possible to remove the larger bound cations (e.g. $Cd^{2+}$ or $Gd^{3+}$) by simple chemical means ($Zn^{2+}$, however, appears to "fall out" with ease) Preliminary results indicate that the lanthanum(III)-containing texaphyrin complex is not appreciably cytotoxic. Nonetheless, the question of intrinsic toxicity is one of such central importance that the cytotoxicity of all new systems should be screened in vitro and, where appropriate, further in vivo toxicity studies carried out.

EXAMPLE 8
Viral Inactivation by Texaphyrin Macrocycles

One aspect of the utility of the present invention is the use of complexes described herein for photon-induced deactivation of viruses and virally infected or potentially infected eucaryotic cells. The general photodeactivation method used in this example was developed by the Infectious Disease and Advanced Laser Applications Laboratories of the Baylor Research Foundation, Dallas, Tex. and is a subject of U.S. Pat. No. 4,878,891 which is incorporated herein by reference.

The efficiency of some of the porphyrin-like macrocycles in photosensitized inactivation of Herpes Simplex Virus Type 1 (HSV-1) and of human lymphocytes and monocytes, both peripheral mononucleated vascular cells (PMC) and cellular hosts of HIV-1 has been initiated. Previous studies of viral inactivation using the macrocyclic photosensitizers dihematoporphyrin ether (DHE) or hematoporphyrin derivative (HPD) have shown that with the porphyrins, only those viruses studied which are enveloped or possess a membraneous coat are inactivated. The enveloped viruses studied include HSV-1, cytomegalovirus, measles virus[133], and the human immunodeficiency virus HIV-1[134].

The photosensitized inactivation of Herpes Simplex Virus, Type 1 (HSV-1) was investigated in culture medium using various macrocycles. Results are listed in Table 1.

TABLE 1

Herpes Simplex Virus I Inactivation with
Expanded Porphyrin Macrocycle Complexes*

| Complex** | Conc. (μM) | % Survival Viral Infectivity |
|---|---|---|
| $1_c$ | 20 | 12 |
|  | 10 | 8 |
|  | 2.5 | 20 |
|  | 0.25 | 100 |
| $5_B$(where M = Cd) | 20 | 4 |
|  | 10 | 14 |
|  | 2.5 | 42 |
|  | 0.25 | 100 |

Figure 5A:
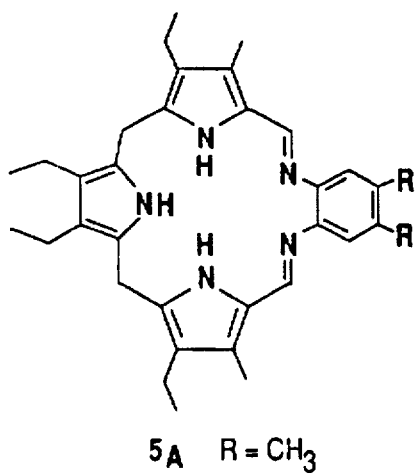
FIG. 5 shows metal complexes and derivatives ($5_A$-$5_E$) of compounds of the parent patent application.
Figure 5B:
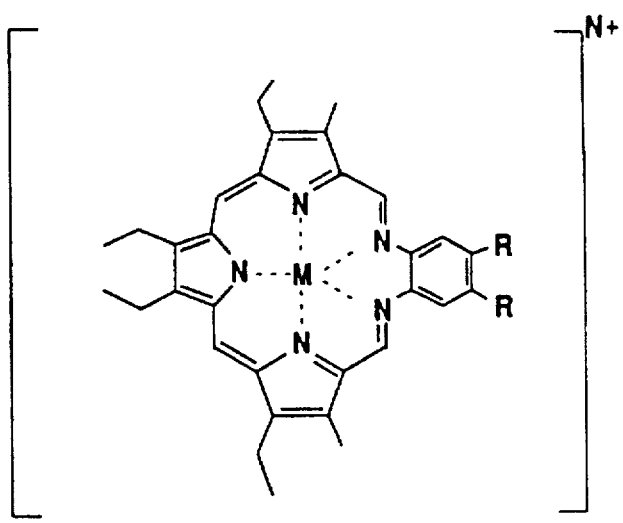

*All light irradiation at λ max absorption and to give a light fluence of 10 J/cm²
**Structural formulas in FIGS. 1 and 5.

The two cadmium-containing macrocycles ($1_C$, $5_B$ (where M is Cd)), at concentrations of 20 μM demonstrated≈90% viral inactivation as judged by viral plaque assay.

The macrocycle photosensitizing studies employed enveloped HSV-1 as the model for screening based on its ease of propagation and assessment of infectivity in cell culture. The screening procedure for photoinactivation of HSV-1 was similar to the methods previously described.[135] Essentially, selected macrocycles at different concentrations were added to a cell-free suspension of $10^6$ PFU/ml of HSV-1. The viral suspensions were irradiated at the optimal absorption wavelength of the selected dye at different light-energy densities. Controls consisted of (1) nonirradiated virus, (2) virus irradiated in the absence of macrocycle, and (3) virus treated with selected concentrations of macrocycle and maintained in the dark. All samples were then assessed for viral infectivity by determining the number of PFU/ml in Vero cells.

Viral suspensions were serially diluted and subsequently absorbed onto Vero cell monolayers for 1½ hours at 37° C. An overlay medium was added and the cells incubated at 37° C. for 3–4 days. The overlay medium was then removed, the monolayers fixed with methanol and tinctured with Giemsa, and individual plaques counted under a dissecting microscope. Uninfected cell cultures also were exposed to the macrocycle complexes to rule out direct cytotoxic effects.

Figure 10:
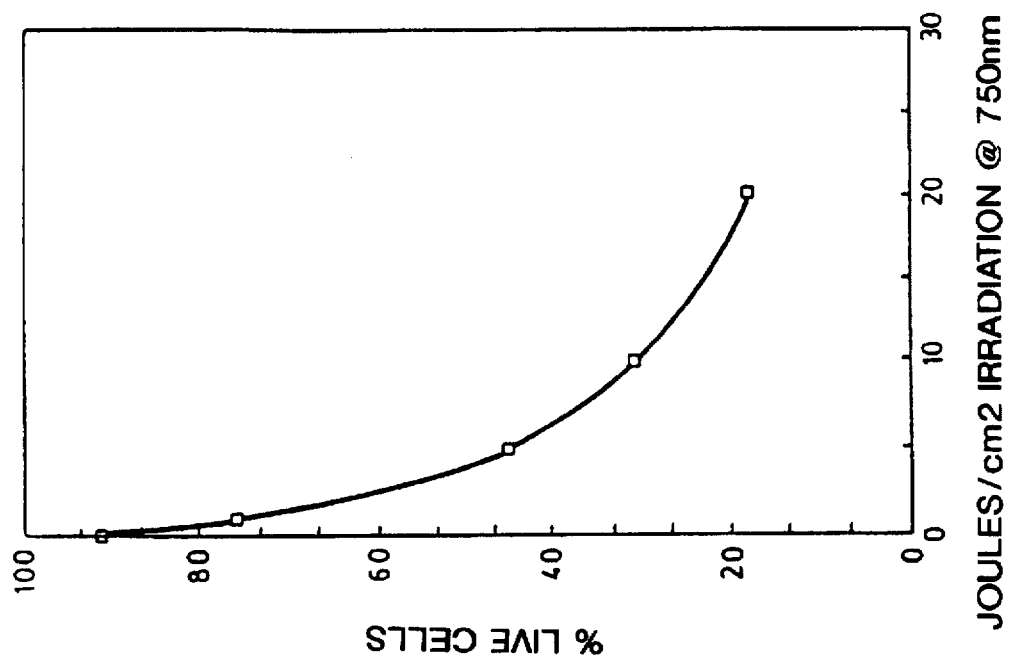
FIG. 10 shows mononuclear cell killing by 1 µg/ml complex $1_C$ and irradiation. Cell kill was determined by [$^3$H]-Thy uptake after PHA stimulation.
Figure 9:
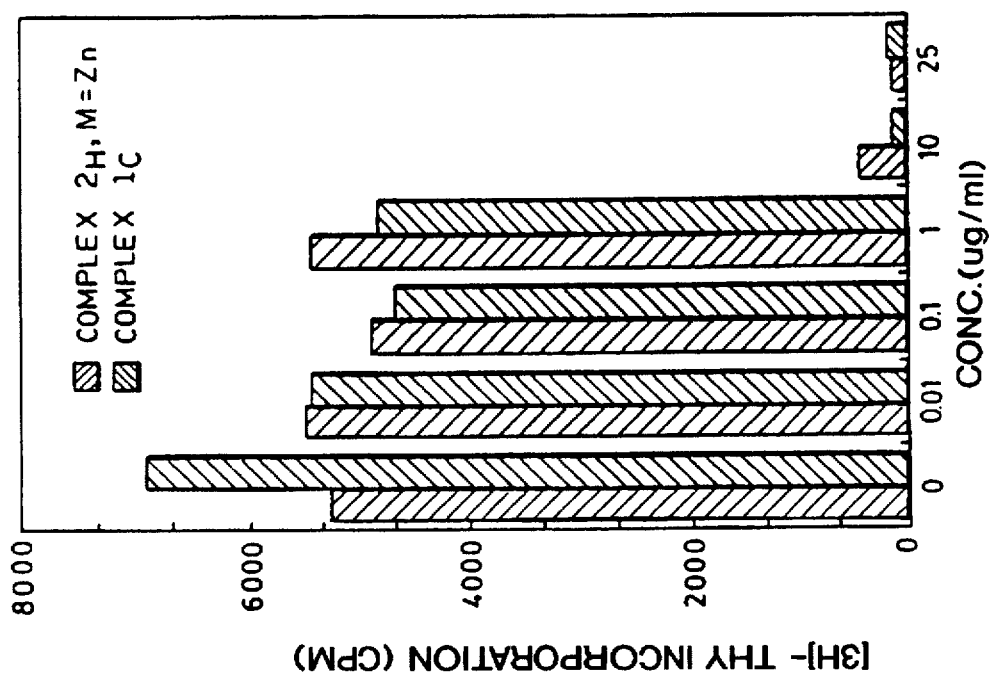
FIG. 9 shows mononuclear cell killing by complexes $2_H$(M=Zn$^{+2}$) and $1_C$ without irradiation. Cell kill was determined by [3H]-Thy uptake after phytohemagglutinin (PHA) stimulation.

The inactivation of PMC's in the absence and presence of light after exposure to concentrations of complex $1_C$ in whole human plasma ranging from 0.015 to 38 μM is shown in FIGS. 9 and 10. Inactivation was judged by mitogenic assay. Toxicity onset with $1_C$ (see FIG. 1) and $2_H$ (M=$Zn^{++}$, see FIG. 2) in the absence of light was between 0.15 and 1.5 μM (FIG. 9). As shown by mitogenic assay in FIG. 10, aerobic photosensitization of cells exposed to $1_C$ at 0.15 μM concentration and 20 joules/$cm^2$ of 770 nm wavelength light caused significant inhibition of the cellular division of PMC's. Moderate increase in either photosensitizer concentration or light dosage is expected to result in essentially complete cellular inactivation.

Results indicate that the expanded porphyrin-like macrocycles should be efficient photosensitizers for free HIV-1 and infected mononuclear cells. Altering the polarity and electrical charges of side groups of these macrocycles is anticipated to alter the degree, rate, and perhaps site(s) of binding to free enveloped viruses such as HIV-1 and to virally-infected peripheral mononuclear cells, thus modulating photosensitizer take-up and photosensitization of leukemia or lymphoma cells contaminating bone-marrow as well.

EXAMPLE 9

Antibody Conjugates

Radioisotopes play a central role in the detection and treatment of neoplastic disorders. Improving their efficacy in medical applications involves attaching radioisotopes to tumor-directed monoclonal antibodies and their fragments. Radiolabeled antibodies could therefore serve as "magic bullets" and allow the direct transport of radioisotopes to neoplastic sites thus minimizing whole body exposure to radiation.[177-187] The use of bifunctional metal chelating agents in radioimmunodiagnostics (RID) and therapy (RIT) is most closely related to the present invention.

Bifunctional metal chelating agents for use in antibody conjugate-based treatment and diagnostic applications must 1) have functional groups suitable for conjugation to the antibody, 2) form covalent linkages that are stable in vivo and which do not destroy the immunological competence of the antibody, 3) be relatively nontoxic, and 4) bind and retain the radiometal of interest under physiological conditions.[187-191] The last of these conditions is particularly severe. The potential damage arising from "free" radioisotopes, released from the conjugate, can be very serious. On the other hand, only nanomole concentrations of isotopes, and hence ligand, are generally required for RID and RIT applications, so that the concerns associated with intrinsic metal and/or free ligand toxicity are somewhat relaxed.

For the purposes of imaging, an ideal isotope should be readily detectable by available monitoring techniques and induce a minimal radiation-based toxic response. In practice these and other necessary requirements implicate the use of a γ-ray emitter in the 100 to 250 KeV range, which possesses a short effective half-life (biological and/or nuclear), decays to stable products, and, of course, is readily available under clinical conditions.[178-180] To date, therefore, most attention has focused on $^{131}$I ($t_{1/2}$=193 h), $^{123}$I($t_{1/2}$=13 h), $^{99m}$Tc($t_{1/2}$=6.0 h), $^{67}$Ga($t_{1/2}$=78 h), and $^{111}$In($t_{1/2}$=67.4 h) which come closest to meeting these criteria.[192] Each of these enjoys advantages and disadvantages with respect to antibody labeling for RID. $^{131}$I and $^{123}$I, for instance, are easily conjugated to antibodies via electrophilic aromatic substitution of tyrosine residues.[193] The metabolism of $^{131}$I or $^{123}$I labeled proteins, however, produces free radioactive iodide anion and as a result can lead to a fair concentration of radioactivity at sites other than those targeted by the antibody-derived "magic bullet".[193] The half-lives of both $^{131}$I and $^{123}$I are relatively inconvenient for optimal use, being too long and too short, respectively, and the fact that $^{131}$I is also a β emitter.[192] $^{99m}$Tc, $^{67}$Ga, and $^{111}$In all suffer from the disadvantage that they cannot be bound directly to the antibody in a satisfactory fashion and require the use of a bifunctional conjugate. The chemistry of such systems is furthest advanced in the case of $^{99m}$Tc, and a number of effective ligands, are now available for the purpose of $^{99m}$Tc administration.[178-188,194] This radioisotope has a very short half-life which makes it technically very difficult to work with. Both $^{67}$Ga and $^{111}$In have longer half-lives and possess desirable emission energies. Both are "hard" cations with high charge density in their most common trivalent forms. No suitable ligands exist for either $^{111}$In$^{3+}$ or $^{67}$Ga$^{3+}$ which form stable nonlabile complexes and which might be suitable for radioimmunological applications. As described elsewhere herein texaphyrin forms a kinetically and hydrolytically stable complex with In$^{3+}$. Such a ligand system may be elaborated and serve as the critical core of a bifunctional conjugate for use in $^{111}$In-based RID.

Many of the same considerations hold true for radioisotope-based therapy as do for radioisotope-based diagnostics: An ideal isotope must also be readily available under clinical conditions (i.e. from a simple decay-based generator),[178] possess a reasonable half-life (i.e. on the order of 6 hours to 4 weeks), and decay to stable products. In addition, the radioisotope must provide good ionizing radiation (i.e. in the 300 KeV to 3 MeV range). A number of β emitters, including $^{131}$I, are currently receiving attention as possible candidates for RIT. Among the more promising, are $^{186}$Re ($t_{1/2}$=90 h, $^{67}$Cu ($t_{1/2}$=58.5 h), and $^{90}$Y ($t_{1/2}$=65 h). Of these, $^{90}$Y is currently considered the best,[192,197] with an emission energy of 2.28 MeV, it is calculated to deliver roughly 3 to 4 times more energy (dose) to the tumor per nanomole than either $^{186}$Re or $^{67}$Cu. Good immuno-compatible chelands exist for only $^{186}$Re and $^{67}$Cu, the former may be attached using the same ligands as were developed for $^{99m}$Tc,[194] and the latter via the rationally-designed activated porphyrins developed by Prof. Lavallee of Hunter College and the Los Alamos INC-11 team.[191] Further benefits should be derived from a bifunctional conjugate which is capable of forming stable, nonlabile complexes with $^{90}$Y$^{3+}$ (which cannot be done with porphyrins). The texaphyrin ligand of the present invention not only forms stable complexes with In$^{3+}$ but also binds Y$^{3+}$ effectively. A texaphyrin-type bifunctional conjugate may be prepared for use in $^{111}$In-based RID and in $^{90}$Y-based RIT. Both $^{90}$Y and $^{111}$In could conceivably be attached to an antibody of choice using a functionalized texaphyrin. The $Y^{3+}$ and $In^{3+}$ complexes of texaphyrin are formed rapidly (insertion and oxidation times are less than 3 hours) from the methylene-linked reduced precursor, and are hydrolytically stable in 1:1 methanol-water mixtures (the half-lives for decomplexation and/or ligand decomposition exceed 3 weeks in both cases.

The hydroxy-substituted texaphyrin molecules of the present invention are especially suited for acting as bifunctional chelating agents in antibody conjugate-based treatment since they have functional groups suitable for conjugation to the antibody, they form covalent linkages that are stable in vivo which do not destroy the immunological competence of the antibody, they are relatively nontoxic, and they are readily soluble in a physiological environment. A further advantage of these soluble texaphyrins is that many of these would be suitable for further functionalization. Treatment of carboxylated texaphyrins with thionyl chloride or p-nitrophenol acetate would generate activated acyl species suitable for attachment to monoclonal antibodies or other biomolecules of interest. Standard in situ coupling methods (e.g. 1,1'-carbonyldiimidazole (CDI)[202]) could be used to effect the conjugation. The ability to attach and deliver a potent photosensitizer directly to a tumor locus could have tremendous potential benefit in the treatment of neoplastic disorders. In addition, this approach will allow a variety of useful radioisotopes such as $^{90}Y$ and $^{111}In$ to be attached to a monoclonal antibody.

The hydroxy-substituted texaphyrin molecules of the present invention are also suited for delivering radioactivity to a tumor on their own since they chelate radioisotopes and have intrinsic biolocalization selectivity.

EXAMPLE 10

Magnetic Resonance Imaging Enhancement, Imaging with B2T2 in vivo

In many respects the key to cancer control lies in early detection and diagnosis as it does in subsequent therapeutic management. New techniques which allow neoplastic tissue to be observed and recognized at an early stage of development thus have a critical role to play in the battle against these disorders. One such promising technique is magnetic resonance imaging (MRI).[136-140] Although quite new, this noninvasive, apparently innocuous method, is now firmly entrenched as a diagnostic tool of prime importance, complementing or, in some cases, supplanting computer assisted X-ray tomography as the method of choice for solid tumor detection.

The physical basis of current MRI methods has its origin in the fact that in a strong magnetic field the nuclear spins of water protons in different tissues relax back to equilibrium at different rates. When these local, tissue-dependent relaxation differences are large, tissue differentiation can be effected. Paramagnetic compounds, containing one or more unpaired spins, enhance the relaxation rates for the water protons in which they are dissolved.[141] The extent of this enhancement is termed relaxivity. At present, only one paramagnetic MRI contrast agent is in clinical use, the bis(N-methyl-glucamine) salt of Gd(III) diethylenetriaminepentaacetate, $(MEG)_2[Gd(DTPA)(H_2O)]$ (c.f. structure 10)[146-153] marketed by Berlex Laboratories. This dianionic complex localizes selectively in extracellular regions, and is being used primarily in the visualization of the capillary lesions associated with cerebral tumors.[146-148]

Considerable effort has been devoted to the development of new potential MRI contrast agents.[156] Most of this work has centered around preparing new complexes of Gd(III).[156-164,171-172] The emphasis on Gd(III) salts stems from the fact that this cation, with 7 unpaired f-electrons, has a higher magnetic moment than other paramagnetic cations such as Fe(III) and Mn(II).[139-140] Thus complexes of Gd(III) would be expected to be superior relaxation agents than those derived from Mn(II) or Fe(III). In addition, both iron and, to a lesser extent, manganese are sequestered and stored very efficiently in humans (and many other organisms) by a variety of specialized metal-binding systems.[173] Moreover both iron and manganese are capable of existing in a range of oxidation states and are known to catalyze a variety of deleterious Fenton-type free-radical reactions.[174] Gadolinium(III), which suffers from neither of these deficiencies, thus appears to offer many advantages. As is true for Fe(III) and Mn(II), the aqueous solution of Gd(III) is too toxic to be used directly for MRI imaging at the 0.01 to 1 mM concentrations required for effective enhancement.[139,140] Hence the emphasis is on developing new agents which, as is true for DTPA, form hydrolytically stable complexes in vivo with Gd(III) and/or other paramagnetic cations. A number of such ligands, including the very promising DOTA[156-162] and EHPG[163,164] systems, are now known (c.f. reference 140 for an extensive review). In almost all cases, however, reliance is made on the same basic philosophical approach. Specifically, for Gd(III) binding, carboxylates, phenolates, and/or other anionic chelating groups are being used to generate intrinsically labile complexes of high thermodynamic stability in the hope that such high thermodynamic stability will translate into a kinetic stability that is sufficient for in vivo applications. Little effort is currently being devoted to the preparation of nonlabile Gd(III) complexes that would in and of themselves enjoy a high kinetic stability. The problem seems to be quite simply that such systems are hard to make. For instance, unlike the transition metal cations which are bound well to porphyrins (a synthetically versatile ligand which is readily subject to modification and which, at least for [Mn(III)TPPS][138], and other water soluble analogues,[165-169] shows good relaxivity and good tumor localizing properties), Gd(III) forms only weak and/or hydrolytically unstable complexes with porphyrins,[165c,169,175] although other simple macrocyclic amine- and imine-derived ligands[171,172,176] will support stable complexes with certain members of the lanthanide series and do show some promise, as yet unrealized, of acting as supporting chelands for Gd(III)-based MRI applications.

According to the present invention nonlabile Gd(III) complexes of hydroxy-substituted texaphyrins prove to be useful contrast agents for MRI applications. Hydroxy-substituted texaphyrins are capable of stabilizing complexes with a variety of di- and trivalent cations, including $Cd^{2+}$, $Hg^{2+}$, $Lu^{+3}$, $Gd^{+3}$, and $La^{+3}$. Such complexes are particularly soluble in physiological environments.

Magnetic Resonance Imaging with B2T2 in vivo

The T2B2 gadolinium complex showed low toxicity and good tissue selectivity in magnetic resonance imaging enhancement.

Imaging: Scanning was performed using a circumferential transmit/receive coil (Medical Advances, Milwaukee, Wis.) in the bore of a 1.5 Tesla Signa scanner (GE Medical Systems, Milwaukee, Wis.). Normal male Sprague-Dawley rats (n=5) weighing from 280–320 grams and rats bearing subcutaneously implanted methylcholanthrene-induced fibrosarcomas in their left flanks (n=4) were studied. Tumor size at the time of the study ranged from 2.5 to 3.5 cm in widest diameter. The rats were anesthetized with 90 mg/kg of ketamine (Vetalar, Aveco Corporation, Fort Dodge, Iowa) and 10 mg/kg of xylazine (Rompun, Mobay Corporation, Shawnee, Kans.) intraperitoneally. Following the insertion of an intravenous catheter in the tail vein, each animal was placed in supine (normal rats) or prone (tumor-bearing rats) position in the center of the coil. Coronal and axial T1 weighted images were obtained of each animal using a spin echo pulse sequence with the following parameters: TR 300 msec, TE 15 msec, slice thickness 5 mm, matrix 128×256, field of view 10 cm, 4 excitations and no phase wrap. Next, 17 umol/kg of the Gd(III)texaphyrin complex dissolved in normal saline was infused at a rate of 0.25 ml/min intravenously and repeat images were obtained at 10–15 minutes post contrast. One tumor-bearing rat was studied at 6 and 28 hours post-contrast. All tuning parameters and the rats' positions were kept identical in the pre and post contrast scans.

Image Analysis: Operator defined regions of interest (ROI) measurements were made on axial slices of all pre and 10–15 minutes post contrast studies. Regions in which measurements were made included the right lobes of the livers and the whole kidneys in the normal rats and the whole tumor in tumor-bearing rats. In addition, large ROI's of background air were measured for standardization purposes. Standardized signal intensities (SSI) were calculated as follows: signal intensity (SI) of organ/SI air. An unpaired Student's t test was used to compare pre contrast and post contrast SSIs.

Toxicity: At 24 hours, there were no deaths in the mice injected i.p. although those receiving the highest dose (312.5 umol/kg) appeared lethargic. Autopsies of two mice from each dosage group revealed some edema and pallor of the liver and kidneys in the two groups receiving the highest doses (312.5 and 156.3 umol/kg). Autopsies from the remaining groups were normal. At 48 hours, the remaining mice (n=3 in each dosage group) in the two highest dosage groups died. The animals in the three lower dosage groups demonstrated no morbidity. There was no mortality or evidence of morbidity in the rats during the month of observation after scanning.

Enhancement: Liver SSI increased by 81.7% (p<0.001), kidney by 114.9% (p<0.001) and tumor by 49.7% (p<0.02) from pre to 10–15 minutes post contrast. There was no significant difference in enhancement between the right and left lobe of the liver and between the two kidneys. Pre contrast, tumor parenchyma appeared homogeneous and of an intensity similar to adjacent muscle. Post contrast, tumor tissue demonstrated a mottled pattern of enhancement and was easily distinguished from adjacent tissues. The MRI appearance reflected the heterogeneous appearance of the tumor grossly which consists of necrotic tissue surrounded by viable stroma. In addition, in the one animal studied at 6 and 28 hours post contrast, there was visible tumor enhancement throughout the study period. The pattern of enhancement, however, changed over time, with enhancement starting at the edges of the tumor initially and including the center by 28 hours.

These results show that the T2B2 gadolinium complex is an hepatic, renal and tumor-specific contrast agent. The agent was found to have relatively low toxicity in rodents. Intravenous administration resulted in statistically significant hepatic, renal and tumor enhancement in rats within 40–15 minutes with persistence of tumor enhancement for up to 28 hours. The early enhancement of tumor edges may represent contrast localization in areas of viable tumor. The later appearance of the tumor probably was caused by passive diffusion of some of the agent into central necrotic areas. It is unclear whether a selective transport or passive diffusion mechanism is responsible for initial tumor enhancement with GD(III)texaphyrin and whether intracellular binding to peripheral-type benzodiazepine receptors occurs. The tumor could be differentiated from adjacent tissues for up to 28 hours.

The chemical properties of this texaphyrin class of macrocyclic ligands can be varied by peripheral substitution, which would allow biological properties to be optimized in terms of biodistribution, pharmacokinetics and toxicity.

Magnetic Resonance Imaging of Atheroma

The gadolinium complex of B2T2 [4,5-diethyl-10,23-dimethyl-9,24-bis(3-hydroxypropyl)-16,17-(3-hydroxypropyloxy)-13,20,25,26,27-pentaaza pentacyclo[20.2.1.1$^{3,6}$.1$^{8,11}$.0$^{14,19}$]heptacosa-1,3,5,7,9,11(27),12,14(19),15,17,20,22(25),23-tridecaene] shows accumulation in human cadaveric aorta. Two aortas obtained from autopsies were examined using magnetic resonance imaging before and after incubation in vitro for 15 minutes with the gadolinium complex of B2T2. Selective labeling of the endothelial cell surface and atheromas plaque relative to surrounding tissue was observed. These data indicate that the Gd(III)B2T2 complex has utility in the non-invasive imaging of atheroma.

Magnetic Resonance Imaging of the Upper GI Tract. The gadolinium complex of B2T2 [4,5-diethyl-10,23-dimethyl-9,24-bis(3-hydroxypropyl)-16,17-(3-hydroxypropyloxy)-13,20,25,26,27-pentaaza pentacyclo[20.2.1.1$^{3,6}$.1$^{8,11}$.0$^{14,19}$]heptacosa-1,3,5,7,9,11(27),12,14(19),15,17,20,22(25),23-tridecaene] shows accumulation in the upper GI tract, especially the stomach, as determined by magnetic resonance imaging.

EXAMPLE 11

Photodynamic Therapy, In vitro and In vivo Experiments

In vitro data and experiments. The lanthanum complex of B2T2 [4,5-diethyl-10,23-dimethyl-9,24-bis(3-hydroxypropyl)-16,17-(3-hydroxypropyloxy)-13,20,25,26, 27-pentaaza pentacyclo[20.2.1.1$^{3,6}$.1$^{8,11}$.0$^{14,19}$]heptacosa-1, 3,5,7,9,11(27),12,14(19),15,17,20,22(25),23-tridecaene] (LaB2T2) was used at concentrations of 5.0, 1.0 or 0.1 micromolar in tissue culture medium. The murine mammary carcinoma cell line designated EMT-6 was cultured in medium containing LaB2T2 for 1 hour or 3 hours in the dark. Experimental cultures were irradiated with 10 Joules/cm$^2$ using an arc lamp with a 750 nanometer band pass filter. Cell survival was measured using a cell cloning assay. There was no dark toxicity indicating that LaB2T2 had no direct toxicity to the cells. Cultures which were irradiated with the visible red light showed viabilities of 3%, 50% and 100% for concentrations of LaB2T2 of 5.0, 1.0 and 0.1 micromolar respectively. The results were similar for 1 and 3 hour incubation periods. The results established that LaB2T2 was phototoxic to these tumor cells in vitro.

In vivo experiments. Murine adenocarcinoma cells were inoculated into both flanks of Balb/c mice. Four days later, palpable tumor masses were present on both flanks of the mice. Ten mg/kg of lutetium B2T2 (LuB2T2) in aqueous solution was injected IV. Seven hours later, one tumor mass was irradiated with 500 Joules of Argon laser light at 746 nanometers. The unirradiated tumor served as a control. Animals were monitored daily and tumor measurements were made using calipers. Following a single treatment, 65% cell kill was estimated based on the reduction in size of the treated tumors. No phototoxicity of skin or normal tissues surrounding the tumors was observed indicating relatively selective uptake of the LuB2T2 in the tumors. This experiment established the in vivo photodynamic activity of LuB2T2 in vivo.

The hydroxy-substituted texaphyrins can be conjugated to biological molecules, especially proteins of molecular weight greater than about 20,000 daltons, e.g. albumin and gamma globulin, in order to slow their clearance by the kidneys. A prolonged presence of these complexes in tissue may be desirable for photoirradiation purposes. The conjugation would be accomplished as described in Example 9 for antibody conjugates.

EXAMPLE 12
Hydroxy-Substituted Texaphyrins in Magnetic Resonance Imaging followed by Photodynamic Therapy for Tumor Destruction This example describes a use of the present invention of hydroxy substituted texaphyrins in the destruction of tumor tissue. A detectable metal complex of a water soluble hydroxy-substituted aromatic pentadentate expanded porphyrin analog retaining lipophilicity, said complex exhibiting selective biolocalization in benign or malignant tumor cells relative to surrounding tissue is administered as a first agent to a host harboring benign or malignant tumor cells. Localization sites in the host are determined by reference to the detectable metal. A water soluble hydroxy-substituted aromatic pentadentate expanded porphyrin analog-detectable-metal complex retaining lipophilicity and having essentially identical biolocalization property and exhibiting the ability to generate singlet oxygen upon exposure to light will be administered as a second agent. The second agent is photoirradiated in proximity to the benign or malignant tumor cells, as is using fiber optics, to cause tumor tissue destruction from the singlet oxygen produced. The water soluble hydroxy-substituted aromatic pentadentate expanded porphyrin analog retaining lipophilicity is a hydroxy-substituted texaphyrin although one skilled in the art can see from the foregoing that substituted sapphyrins, pentaphyrins or other macrocyclic ligands capable of chelating a metal, soluble in aqueous fluids and localizing in a lipid rich environment may be of particular value. The detectable metal in the first agent is a paramagnetic metal, preferably Gd(III) or a gamma emitting metal. The localization sites are determined using MRI when a paramagnetic metal is used and gamma body scanning when a gamma emitting metal is used. The detectable metal in the second agent is a diamagnetic metal, preferably La(III), Lu(III) or In(III). Texaphyrin-metal complexes will be chosen which themselves show a high intrinsic biolocalization selectivity for tumors or neoplastic tissues. For example, the B2T2 Gd(III) complex demonstrates in vivo affinity for tissue high in lipid content, atheroma, the liver, kidneys and tumors. When appropriately followed by fiber optic photodynamic therapy, cells in the atheroma or tumor can be deactivated.

The hydroxy substituted diamagnetic texaphyrin complexes are good candidates for such biomedical photosensitizers. They are easily available, have low intrinsic cytotoxicity, long wavelength absorption, generate singlet oxygen, are soluble in physiological environments, have the ability to be conjugated to site specific transport molecules, have quick elimination, are stable and are easily subject to synthetic modification.

Literature citations in the following list are incorporated by reference herein for the reasons cited.

REFERENCES

1. "The Porphyrins"; Dolphin, D., Ed.; Academic Press: New York, 1978–1979; Vols. I–VII.
2. "Superphthalocyanine", a pentaaza aromatic phthalocyanine-like system was prepared by a uranyl-medicated condensation; it is not obtainable as the free-base or in other metal-containing forms: (a) Day, V. W.; Marks, T. J.; Wachter, W. A. J. Am. Chem. Soc. 1975, 97, 4519–4527. (b) Marks, T. J.; Stojakovic, D. R. J. Am. Chem. Soc. 1978, 100, 1695–1705. (c) Cuellar, E. A.; Marks, T. J. Inorg. Chem. 1981, 20, 3766–3770.
3. Bauer, V. J.; Clive, D. R.; Dolphin, D.; Paine, J. B. III; Harris, F. L.; King, M. M.; Loder, J.; Wang, S.-W. C.; Woodward, R. B. J. Am. Chem. Soc. 1983, 105, 6429–6436. To date only tetracoordinated metal complexes have been prepared from these potentially pentadentate ligands.
4. For an example of a porphyrin-like system with a smaller central cavity, see: (a) Vogel, E.; Kocher, M.; Schmickler, H.; Lex, J. Angew. Chem. 1986, 98, 262–263; Angew. Chem., Int. Ed. Engl. 1986, 25, 257–258. (b) Vogel, E.; Balci, M.; Pramod, K.; Koch, P.; Lex, J.; Ermer, O. Angew. Chem. 1987, 26, 928–931; Angew. Chem., Int. Ed. Engl. 1987, 26, 928–931.
5. Mertes et al. have recently characterized a five-coordinate copper complex of an elegant (but nonaromatic) porphyrin-like "accordion" ligand derived from dipyrromethines: (a) Acholla, F. V.; Mertes, K. B. Tetrahedron Lett. 1984, 3269–3270. (b) Acholla, F. V.; Takusagawa, F.; Mertes, K. B. J. Am. Chem. Soc. 1985, 6902–6908. Four-coordinate copper complexes of other nonaromatic pyrrole-containing macrocycles have also been prepared recently: Adams, H.; Bailey, N. A.; Fenton, D. A.; Moss, S.; Rodriguez de Barbarin, C. O.; Jones, G. J. Chem. Soc., Dalton Trans. 1986, 693–699; Fenton, D. E.; Moody, R. J. Chem. Soc., Dalton Trans. 1987, 219–220.
6. Broadhurst, M. J.; Grigg, R.; Johnson, A. W. J. Chem. Soc., Perkin Trans. 1 1972, 2111–2116.
7. (a) Broadhurst, M. J.; Grigg, R.; Johnson, A. W. J. Chem. Soc., Chem. Commun. 1969, 23–24. Broadhurst, M. J.; Grigg, R.; Johnson, A. W. J. Chem. Soc., Chem. Commun. 1969, 1480–1482. Broadhurst, M. J.; Grigg, R.; Johnson, A. W. J. Chem. Soc., Chem. Commun. 1970, 807–809.
8. (a) Berger, R. A.; LeGoff, E. Tetrahedron Lett. 1978, 4225–4228. (b) LeGoff, E.; Weaver, O. G. J. Org. Chem. 1987, 710–711.
9. (a) Rexhausen, H.; Gossauer, A. J. Chem. Soc. Chem. Commun. 1983, 275. (b) Gossauer, A. Bull. Soc. Chim. Belg. 1983, 92, 793–795.
10. Gosmann, M.; Franck, B. Angew. Chem. 1986, 98, 1107–1108; Angew. Chem., Int. Ed. Engl. 1986, 25, 1100–1101.
11. The systematic name for compounds 2 is 4,5,9,24-tetraethyl-10,23-dimethyl-13,20,25,26,27-pentaazapentacyclo[20.2.1.1$^{3,6}$.1$^{8,11}$.0$^{14,19}$]heptacosa-1,3,5,7,9,11(27),12,14,16,18,20,22(25),23-tridecaene.
12. Nonaromatic planar pentadentate pyridine-derived ligands are known. See, for instance: (a) Curtis, N. F. In Coordination Chemistry of Macrocyclic Compounds; Melson, G. A., Ed.; Plenum: New York, 1979; Chapter 4. (b) Nelson, S. M. Pure Appl. Chem. 1980, 52, 2461–2476. (c) Ansell, C. W. G.; Lewis, J.; Raithby, P. R.; Ramsden, J. N.; Schroder, M. J. Chem. Soc., Chem. Commun. 1982, 546–547. (d) Lewis, J.; O'Donoghue, T. D.; Raithby, P. R. J. Chem. Soc., Dalton Trans. 1980, 1383–1389. (e) Constable, E. C.; Chung, L.-Y.; Lewis, J.; Raithby, P. R. J. Chem. Soc., Chem. Commun. 1986, 1719–1720. (f) Constable, E. C.; Holmes, J. M.; McQueen, R. C. S. J. Chem. Soc., Dalton Trans. 1987, 5–8.
13. (a) Sessler, J. L.; Johnson, M. R.; Lynch, V. J. Org. Chem. 1987, 52, 4394–4397. (b) Sessler, J. L.; Murai, T.; Lynch, V.; Cyr, M. J. Am. Chem. Soc. 1988, 110, 5586–5588.
14. Sessler, J. L.; Johnson, M. R.; Lynch, V.; Murai, T. J. Coord. Chem., 1988, 18, 99–104

15. Satisfactory spectroscopic, mass spectrometric, and/or analytical data were obtained for all new compounds.
16. OEP=octaethylporphyrin and TPP=tetraphenylporphyrin; the prefixes $H_2$ and Cd refer to the free-base and cadmium(II) forms, respectively; pyr=pyridine.
17. (a) Scheer, H.; Katz, J. J. In Porphyrins and Metalloporphyrins; Smith, K., Ed.; Elsevier: Amsterdam, 1975; Chapter 10. (b) Janson, T. R.; Katz, J. J.; in ref. 1, Vol. IV, Chapter 1.
18. Gouterman, M., in ref. 1, Vol. III, Chapter 1.
19. Becker, R. S.; Allison, J. B. J. Phys. Chem. 1963, 67, 2669.
20. Texaphyrin $1_C \cdot NO_3$ was crystallized from $CHCl_3$-hexanes in a triclinic space group.
21. Hoard, J. L.. In Porphyrins and Metalloporphyrins; Smith, K., Ed.; Elsevier: Amsterdam, 1975; Chapter 8.
22. Hazell, A. Acta Crystallogr., Sect. C: Cryst. Struct. Commun. 1986, C42, 296–299.
23. Rodesiler, P. F.; Griffith, E. H.; Ellis, P. D.; Amma, E. L. J. Chem. Soc. Chem. Commun. 1980, 492–493.
24. (a) Miller, J. R. Dorough, G. D. J. Am. Chem. Soc. 1952, 74, 3977–3981. (b) Kirksey, C. H.; Hambright, P. Inorg. Chem. 1970, 9, 958–960.
25. The bispyridine cadmium complex, of compound $1_C$, appears to be the first seven-coordinate cadmium complex derived from all nitrogen donors. For examples of other pentagonal bipyramidal cadmium complexes, see: (a) Cameron, A. F.; Taylor, D. W.; Nuttall, R. H. J. Chem. Soc., Dalton Trans. 1972, 1608–1614. (b) Liles, D. C.; McPartlin, M.; Tasker, P. A.; Lip, H. C.; Lindoy, L. F. J. Chem. Soc., Chem. Commun. 1976, 549–551. (c) Nelson, S. M.; McFall, S. G.; Drew, M. G. B.; Othman, A. H. B.; Mason, N. G. J. Chem. Soc. Chem. Commun. 1977, 167–168. (d) Drew, M. G. B. Othman, A. H. B.; McFall, S. G.; McIlroy, A. D. A.; Nelson, S. M. J. Chem. Soc., Dalton Trans. 1977, 1173–1180. (e) Charles, N. G. Griffith, E. A. H.; Rodesiler, P. F.; Amma, E. L. Inorg. Chem. 1983, 22, 2717–2723.
26. Of the many oxidants available, each would need to be tested individually for suitable oxidizing ability for each Texaphyrin derivative.
27. Whitlock, H. W., Jr.; Buchanan, D. H. Tetrahedron Lett. 1969, 42, 3711–3714.
28. Fischer, H.; Guggemos, H.; Schafer, A. Liebigs Ann. Chem. 1939, 540, 30–50.
29. Johnson, A. W.; Kay I. T.; Markham, E.; Price, P.; Shaw, K. B., J. Chem. Soc. 1959, 3416–3424.
30. Cotton, F. A.; Wilkinson, G. "Advanced Inorganic Chemistry, $4^{th}$ ed.," John Wiley, New York, 1980, pp. 589 and 982.
31. The systematic name for this compound is 4,5,9,24-tetraethyl-10,16,17,23-tetramethyl-13,20,25,26,27-pentaazapentacyclo-[20.2.1.1$^{3,6}$.1$^{8,11}$.0$^{14,19}$]heptacosa-1,3,5,7,9,11(27),12,14,16,18,20,22(25),23-tridecaene.
32. (a) Buchler, J. W.; Cian, A.D.; Fischer, J.; Kihn-Botulinski, M.; Paulus, H.; Weiss, R. J. Am. Chem. Soc. 1986, 108, 3652–2659. (b) Buchler, J. W.; Cian, A. D.; Fischer, J.; Kinh-Botulinski, M.; Weiss, R. Inorg. Chem. 1988, 27, 339–345. (c) Buchler, J. W.; Scharbert, B. J. Am. Chem. Soc. 1988, 110, 4272–4276. (d) Buchler, J. W.; Kapellmann, H. G.; Knoff, M.; Lay, K. L.; Pfeifer, S. Z. Naturforsch. 1983, 38b, 1339–1345.
33. Horrocks, W. D.; Hove, E. G. J. Am. Chem. Soc. 1978, 100, 4386–4392.
34. Lyon, R. C.; Faustino, P. J.; Cohen, J. S.; Katz, A.; Mornex, F.; Colcher, D.; Baglin, C.; Koenig, S. H.; Hambright, P. Magn. Reson. Med. 1987, 4, 24–33.
35. Sessler, J. L.; Cyr, M.; Murai, T. Comm. Inorg. Chem., 1988, 7, 333.
36. Stark, W. M.; Baker, M. G.; Raithby, P. R.; Leeper, F. J.; Battersby, A. R. J. Chem. Soc., Chem. Commun. 1985, 1294.
37. For reviews see: (a) Drew, M. G. B. Prog. Inorg. Chem. 1977, 23, 67–210. (b) Melson, G. A. in "Coordination Chemistry of Macrocyclic Compounds", Melson, G. A., Ed.; Plenum: New York, 1979, Chapter 1. (c) N. F. Curtis, in "Coordination Chemistry of Macrocyclic Compounds", Melson, G. A., Ed.; Plenum: New York, 1979, Chapter 4. (d) Nelson, S. M. Pure and Appl. Chem. 1980, 52, 2461–2476. (e) Lindoy, L. F. in "Synthesis of Macrocycles", Izatt, R. M. and Christensen, J. J., Eds.; J. Wiley: New York, 1987, Chapter 2. (f) Newkome, G. R.; Gupta, V. K.; Sauer, J. D. in "Heterocyclic Chemistry", Newkome, G. R., Ed.; J. Wiley: New York, 1984, Vol. 14, Chapter 3. (g) De Sousa, M.; Rest, A. J. Adv. Inorg. Chem. Radiochem. 1978, 21, 1–40. (h) See also ref. 12.
38. For recent examples of bipyridine-derived systems and related pentadentate ligands, see: (a) Ansell, C. W. G.; Lewis, J.; Raithby, P. R.; Ramsden, J. N.; Schroder, M. J. Chem. Soc., Chem. Commun., 1982, 546–547. (b) Lewis, J.; O'Donoghue, T. D.; Raithby, P. R. J. Chem. Soc., Dalton Trans., 1980, 1383–1389. (c) Constable, E. C.; Chung, L.-Y.; Lewis, J.; Raithby, P. R. J. Chem. Soc., Chem. Commun., 1986, 1719–1720. (d) Constable, E. C.; Holmes, J. M.; McQueen, R. C. S. J. Chem. Soc., Dalton Trans., 1987, 5–8.
39. Chemical & Engineering News Aug. 8, 1988, 26–27.
40. For a recent review see: Lauffer, R. B. Chem. Rev. 1987, 87, 901–927.
41. Kornguth, S. E.; Turski, P. A.; Perman, W. H.; Schultz, R.; Kalinke, T.; Reale, R.; Raybaud, F. J. Neurosurg. 1987, 66, 898–906.
42. Koenig, S. H.; Spiller, M.; Brown, R. D.; Wolf, G. L. Invest. Radiol. 1986, 21, 697–704.
43. Cacheris, W. P.; Nickle, S. K.; Sherry, A. D. Inorg. Chem. 1987, 26, 958–960.
44. (a) Loncin, M. F.; Desreux, J. F.; Merciny, E. Inorg. Chem. 1986, 25, 2646–2648. (b) Spirlet, M.-R.; Rebizant, J.; Desreux, J. F.; Loncin, M.-F. Inorg. Chem. 1984, 23, 359–363.
45. (a) Chang, C. A.; Sekhar, V. C. Inorg. Chem. 1987, 26, 1981–1985. (b) Chang, C. A.; Ochaya, V. O. Inorg. Chem. 1986, 25, 355–358. (c) Chang, C. A.; Rowland, M. E. Inorg. Chem. 1983, 22, 3866–3869.
46. Radzki, S.; Krauz, P.; Gaspard, S.; Giannotti, C. Inorg. Chim. Acta 1987, 138, 139–143.
47. Buchler, J. W. in "The Porphyrins," Dolphin, D. ed., Academic Press, New York, 1978, Vol. 1, Chapter 10.
48. Hoard, J. L. in "Porphyrins and Metalloporphyrins"; Smith, K., Ed; Elsevier, Amsterdam, 1975, Chapter 8.
49. (a)(Horrocks, W. D., Jr.; Wong, C.-P. J. Am. Chem. Soc. 1976, 98, 7157–7162. (b) Wong, C.-P.; Venteicher, R. F.; Horrocks, W. D., Jr. J. Am. Chem. Soc. 1974, 96, 7149–7150.
50. Srivastava, T. S. Bioinorg. Chem. 1978, 8, 61–76.
51. Although several large porphyrin-like aromatic macrocycles, including the "sapphyrins", "platyrins", "pentaphyrin", and "[26]porphyrin" have been prepared in their metal-free forms, and a uranyl complex has been stabilized with a large "superphthalocyanine", we are not aware of any lanthanide complexes formed from these systems.
52. Bauer, V. J.; Clive, D. R.; Dolphin, D.; Paine, J. B. III; Harris, F. L.; King, M. M.; Loder, J.; Wang, S.-W. C.; Woodward, R. B. J. Am. Chem. Soc. 1983, 105, 6429–6436.

53. Broadhurst, M. J.; Grigg, R.; Johnson, A. W. J. Chem. Soc. Perkin Trans. 1, 1972, 2111-2116.
54. (a) Berger, R. A.; LeGoff, E. Tetrahedron Lett. 1978, 4225-4228. (b) LeGoff, E.; Weaver, O. G. J. Org. Chem. 1987, 710-711.
55. (a) Rexhausen, H.; Gossauer, A. J. Chem. Soc., Chem. Commun. 1983, 275. (b) Gossauer, A. Bull. Soc. Chim. Belg. 1983, 92, 793-795.
56. Gosmann, M.; Franck, B. Angew. Chem. 1986, 98, 1107-1108; Angew. Chem. Int. Ed. Eng. 1986, 25, 1100-1101.
57. (a) Day, V. W.; Marks, T. J.; Wachter, W. A. J. Am. Chem. Soc. 1975, 97, 4519-4527. (b) Marks, T. J.; Stojakovic, D. R. J. Am. Chem. Soc. 1978, 100, 1695-1705. (c) Cuellar, E. A.; Marks, T. J. Inorg. Chem. 1981, 20, 3766-3770.
58. Sessler, J. L.; Cyr, M.; Murai, T. Comm. Inorg. Chem., 1988, 7, 333.
59. For examples of lanthanide cationic complexes stabilized by more conventional Schiff base macrocycles see for instance: (a) Backer-Dirks, J. D. J.; Gray, C. J.; Hart, F. A.; Hursthouse, M. B.; Schoop, B. C. J. Chem. Soc., Chem. Commmun. 1979, 774-775. (b) De Cola, L.; Smailes, D. L.; Vallarino, L. M. Inorg. Chem. 1986, 25, 1729-1732. (c) Sabbatini, N.; De Cola, L.; Vallarino, L. M.; Blasse, G. J. Phys. Chem. 1987, 91, 4681-4685. (d) Abid, K. K.; Fenton, D. E.; Casellato, U.; Vigato, P.; Graziani, R. J. Chem. Soc., Dalton Trans. 1984, 351. (e) Abid, K. K.; Fenton, D. E. Inorg. Chim. Acta 1984, 95, 119-125. (f) Sakamoto, M. Bull Chem. Soc. Jpn. 1987, 60, 1546-1548.
60. Confronting AIDS, National Academy of Sciences Press: Washington, D.C., 1988.
61. Dougherty, T. J.; Kaufman, J. E.; Goldfarg, A.; Weishaupt, K. R.; Boyle, D.; Mittleman, A. Cancer Res. 1978, 38, 2628.
62. Dahlman, A.; Wile, A. G.; Burns, R. G.; Mason, G. R.; Johnson, F. M.; Berns, M. W. Cancer Res. 1983, 43, 430.
63. Dougherty, T. J. in Methods in Porphyrin Photosensitization, Kessel, D., Ed.; Plenum Press: New York, 1985; pp. 313-328.
64. Dougherty, T. J. Photochem. Photobiol. 1987, 45, 879.
65. See for instance: (a) Figge, F. H. J.; Weiland, G. S. Anat. Rec. 1948, 100, 659; (b) Rasmussen-Taxdall, D. S.; Ward, G. E.; Figge, F. H. Cancer (Phila.) 1955, 8, 78.
66. Berenbaum, M. C.; Bonnett, R.; Scourides, P. A. Br. J. Cancer 1982, 47, 571.
67. Berns, W.; Dahlman, A; Johnson, F. M.; et al. Cancer Res. 1982, 42, 2326.
68. Dougherty, T. J.; Gomer, C. J.; Weishaupt, K. R. Cancer Res. 1976, 36, 2330.
69. Dougherty, T. J. Photochem. Photobiol. 1983, 38, 377.
70. Evensen, J. F.; Sommer, S.; Moan, J.; Chistensen, T. Cancer Res. 1984, 44, 482.
71. Gibson, S. L. Hilf, R. Photochem. Photobiol. 1985, 42, 367.
72. Gomer, C. J.; Smith, D. M. Photochem. Photobiol. 1980, 32, 341.
73. Herra-Ornelas, L.; Petrelli, N. J.; Mittleman, A.; Dougherty, T. J.; Boyle, D. G. Cancer, 1986, 57, 677.
74. Kessel, D. Photochem. Photobiol. 1984, 39, 851.
75. Kessel, D. Photochem. Photobiol. 1986, 44, 489.
76. Kessel, D. Int. J. Radiat. Biol. 1986, 49, 901.
77. Klaunig, J. E.; Selman, S. H.; Shulok, J. R.; Schaefer, P. J.; Britton, S. L.; Goldblatt, P. J. Am. J. Path. 1985, 119, 230.
78. Moan, J.; Somer, S. Cancer Lett. 1987, 21, 167.
79. Moan, J.; Peng, Q.; Evensen, J. F.; Berg, K.; Western, A.; Rimington, C. Photochem. Photobiol. 1987, 46, 713.
80. Singh, G.; Jeeves, W. P.; Wilson, B. C.; Jang, D. Photochem. Photobiol. 1987, 46, 645.
81. Bonnett, R.; Ridge, R. J.; Scourides, P. A. J. Chem. Soc., Perkin Trans. I 1981, 3135.
82. Chang, C. K.; Takamura, S.; Musselman, B. D.; Kessel, D. ACS Adv. Chem. Ser. 1986, 321, 347.
83. Dougherty, T. J. Photochem. Photobiol. 1987, 46, 569.
84. Kessel, D. Photochem. Photobiol. 1986, 44, 193.
85. Moan, J.; Christensen, T.; Somer, S. Cancer Lett. 1982, 15, 161.
86. Scourides, P. A.; Bohmer, R. M.; Kaye, A. H.; Morstyn, G. Cancer Res. 1987, 47, 3439.
87. Blum, A.; Grossweiner, L. I. Photochem. Photbiol. 1985, 41, 27.
88. Henderson, B. W.; Miller, A. C. Radiat. Res. 1986, 108, 196.
89. Keene, J. P.; Kessel, D.; Land, E. J.; Redmond, R. W.; Truscott, T. G. Photochem. Photobiol. 1986, 43, 117.
90. Parker, J. G. Lasers Surg. Med. 1986, 6, 258.
91. Tanielian, C.; Heinrich, G.; Entezami, A. J. Chem. Soc., Chem. Commun. 1988, 1197.
92. Weishaupt, K. R.; Gomer, L. J.; Dougherty, T. J. Cancer Res. 1976, 36, 2326.
93. Gulliya, K. S.; Matthews, J. L.; Fay, J. W.; Dowben, R. M. Life Sciences 1988, 42, 2651.
94. Matthews, J. L.; Newman, J. T.; Sogandares-Bernal, F.; Judy, M. M.; Kiles, H.; Leveson, J. E.; Marengo-Rowe, A. J.; Chanh, T. C. Transfusion, 1988, 28, 81.
95. Skiles, H.; Sogandares-Bernal, F.; Judy, M. M.; Matthews, J. L.; Newman, J. T. Abstracts of 6th Southern Biomedical Engineering Conference, 1987, 83.
96. Skiles, H.; Judy, M. M. Newman, J. T. in Abstracts of the Annual Meeting of the American Society for Microbiology, 85th Annual Meeting, Mar. 3-7, 1985, p. 7, A 38.
97. Lewin, A. A.; Schnipper, L. E.; Crumpacker, C. S. Proc. Soc. Exptl. Biol. Med. 1980, 163, 81.
98. Schnipper, L. E.; Lewin, A. A.; Swartz, M.; Crumpacker, C. S. J. Clin. Invest. 1980, 65, 432.
99. (a) For an overview see: C. J. Gomer, Photochem. Photobiol. 1987, 46, 561 (this special issue is entirely devoted to this topic). See also: (b) T. J. Dougherty, Photochem. Photobiol. 1987, 45, 879; (c) A. R. Oseroff, D. Ohuoha, G. Ara, D. McAuliffe, J. Foley, and L. Cincotta, Proc. Natl. Acad. Sci. U.S.A., 1986, 83, 9729; (d) S. Wan, J. A. Parrish, R. R. Anderson, and M. Madden, Photochem. Photobiol., 1981, 34, 679; (e) A. Dahlman, A. G. Wile, R. B. Burns, G. R. Mason, F. M. Johnson, and M. W. Berns, Cancer Res., 1983, 43, 430.
100. J. L. Matthews, J. T. Newsam, F. Sogandares-Bernal, M. M. Judy, H. Skiles, J. E. Levenson, A. J. Marengo-Rowe, and T. C. Chanh, Transfusion, 1988, 28, 81.
101. (a) M. R. Detty, P. B. Merkel, and S. K. Powers, J. Am. Chem. Soc., 1988, 110, 5920; (b) R. Bonnett, D. J. McGarvey, A. Harriman, E. J. Land, T. G. Truscott, and U.-J. Winfield, Photochem. Photobiol., 1988, 48, 271; (c) R. Bonnett, S. Ioannou, R. D. White, U.-J. Winfield, and M. C. Berenbaum, Photobiochem. Photobiophys. 1987, Suppl., 45; (d) P. A. Scourides, R. M. Bohmer, A. H. Kaye, and G. Morstyn, Cancer Res., 1987, 47, 3439; (e) M. C. Berenbaum, S. L. Akande, R. Bonnett, H. Kaur, S. Ioannou, R. D. White, and U.-J. Winfield, Br. J. Cancer, 1986, 54, 717; (f) J.-D. Spikes, Photochem. Photobiol., 1986, 43, 691; (g) D. Kessel and C. J. Dutton, Photochem. Photobiol., 1984, 40, 403.
102. P. A. Firey and M. A. J. Rodgers, Photochem. Photobiol., 1987, 45, 535.

103. (a) J. L. Sessler, T. Murai, V. Lynch, and M. Cyr. J. Am. Chem. Soc., 1988, 110, 5586. (b) J. L. Sessler, T. Murai, and G. Hemmi, Inorg. Chem. 1989, 28, 3390.

104. Curran, J. W.; Lawrence, D. N.; Jaffe, H.; et al. N. Engl. J. Med. 1984, 310, 69.

105. Groopman, J. E.; Hartzband, P. I.; Shulman, L.; et al. Blood 1985, 66, 742.

106. Ward, J. W.; Deppe, D. A.; Samson, S.; et al. Ann. Intern. Med. 1987, 106, 61.

107. Ward, J. W.; Holmber, S. D.; Allen, J. R.; et al. N. Engl. J. Med. 1988, 318, 473.

108. Ho, D. D.; Pomerantz, R. J.; Kaplan, J. C. New Engl. J. Med. 1987, 317, 278.

109. Christensen, T.; Sandquist, T.; Feven, K.; Waksvik, H.; Moan, J. Br. J. Cancer 1983, 48, 35.

110. Profio, A. E.; Doiron, D. R. Photochem. Photobiol. 1987, 46, 591.

111. Wan, S.; Parrish, J. A.; Anderson, R. R.; Madden, M. Photochem. Photobiol 1981, 34, 679.

112. Eichler, J.; Knop, J.; Lenz, H. Rad. Environ. Biophys. 1977, 14, 239.

113. Oseroff, A. R.; Ohuoha, D.; Ara, G.; McAuliffe, D.; Foley, Jr.; Cincotta, L. Proc. Natl. Acad. Sci. USA 1986, 83, 9729; and references therein.

114. Gulliya, K. S.; Matthews, J. L. Cell Biol. Int. Rep. 1988, 12, 305; and references therein.

115. Detty, M. R.; Merkel, P. B.; Powers, S. K. J. Am. Chem. Soc. 1988, 110, 5920.

116. Morgan, A. R.; Rampersaud, A.; Keck, R. W.; Selman, S. H. Photochem. Photobiol. 1987, 46, 441.

117. Beems, E. M.; Dubbelman, T. M. A. R.; Lugtenburg, J; Van Best, J. A.; Smeets, M. F. M. A.; Boeheim, J.P. J. Photochem. Photobiol. 1987, 46, 639.

118. Cubeddu, R. Keir, W. F.; Ramponi, R.; Truscott, T. G. Photochem. Photobiol. 1987, 46, 633.

119. (a) Kessel, D.; Dutton, C. J. Photochem. Photobiol. 1984, 40, 403; (b) Kessel, D. Cancer Res. 1986, 46, 2248.

120. (a) Dolphin, D. 196th American Chemical Society Meeting, Los Angeles, September 1988, Abstract no. 312; (b) Richter, A. M.; Kelly, B.; Chow, J.; Liu, D. J.; Towers, G. H. N.; Dolphin, D.; Levy, J. of Natl. Cancer Inst., 1987, 79, 1327.

121. (a) Ben-Hur, E.; Rosenthal, I. Inter. J. Radiat. Biol. 1985, 47, 145; (b) Ben-Hur, E.; Rosenthal, I. Photochem. Photobiol. 1985, 42, 129; (c) Ben-Hur, E.; Rosenthal, I. Rad. Res. 1985, 103, 403; (d) Selman, S. H.; Kreimer-Birnbaum, M.; Chaudhuri, K.; Garbo, G. M.; Seaman, D. A.; Keck, R. W.; Ben-Hur, E.; Rosenthal, I. J. Urol. 1986, 136, 141; (e) Ben-Hur, E.; Rosenthal, I. Cancer Lett. 1986, 30, 321; (f) Ben-Hur, E.; Rosenthal, I. Photochem. Photobiol. 1986, 43, 615; (g) Ben-Hur, E.; Green, M.; Prager, A.; Kol, R.; Rosenthal, I. Photochem. Photobiol. 1987, 46, 651.

122. (a) Firey, P. A.; Rodgers, M. A. J. Photochem. Photobiol. 1987, 45, 535; (b) Firey, P. A.; Ford, W. E.; Sounik, J. R.; Kenney, M. E.; Rodgers, M. A. J. J. Am. Chem. Soc. 1988, 110, 7626.

123. (a) Skikes, J. D. Photochem. Photobiol. 1986, 43, 691; (b) Spikes, J. D.; Bommer, J. C. Int. J. Rad. Res. 1986, 50, 41.

124. Brasseur, N.; Ali, H. Autenrieth, D.; Langlois, R.; van Lier, J. E. Photochem. Photobiol. 1985, 42, 515.

125. Bown, S. G.; Tralau, C. J.: Coleridge Smith, P. D.; Akdemir, D.; Wieman, T. V. Br. J. Cancer 1986, 54, 43.

126. Chan, W.-S; Svensen, R.; Phillips, D.; Hart, I. R., Br. J. Cancer 1986, 53, 255.

127. Sonoda, M.; Krishna, C. M.; Riesz, P. Photochem. Photobiol. 1987, 46, 625.

128. For a review see: Sessler, J. L.; Cyr, M.; Murai, T. Comm. Inorg. Chem. 1988, 7, 333.

129. (a) Sessler, J. L.; Murai, T.; Lynch, V.; Cyr, M. J. Am. Chem. Soc. 1988, 110, 5586; (b) Sessler, J. L.; Murai, T.; Lynch, Inorg. Chem. 1989, 28, 1333; (c) Harriman, T.; Maiya, B. G.; Murai, T.; Hemmi, G.; Sessler, J. L.; Mallouk, T. E. J. Chem. Soc., Chem. Commun., Issue 5, 1989, 314; (d) Sessler, J. L.; Murai, T.; Hemmi, G. Inorg. Chem., 1989, 28, 3390.

130. (a) Gosmann, M.; Franck, B. Angew. Chem. 1986, 98, 1107; Angew. Chem. Int. Ed. Eng. 1986, 25, 1100. (b) Knubel, G.; Franck, B. Angew. Chem. 1988, 100, 1203; Angew. Chem. Int. Ed. Eng. 1988, 27, 1170.

131. (a) Vogel, A.; Jux, N.; Rodriquez-Val, E.; Lex, J.; Schmickler, H. Angew. Chem. Int. Ed. Eng. 1990, 29, 1387. (b) Vogel, E.; Kocher, M.; Schmickler, H.; Lex, J. Angew. Chem. 1986, 98, 262; Angew. Chem. Int. Ed. Eng. 1986, 25, 257. (b) Vogel, E.; Balci, M.; Pramod, K.; Koch, P.; Lex, J. Ermer, O. Angew. chem. 1987, 26, 928; Angew. Chem. Int. Ed. Eng. 1987, 26, 928.

132. Aramendia, P. F.; Redmond, R. W.; Nonell, S.; Schuster, W.; Braslavsky, S. E.; Schaffner, K.; Vogel, E. Photochem. Photobiol. 1986, 44, 555.

133. Skiles, H. L., Judy, M. M. and Newman, J. T. Abstracts to the Annual Meeting of the ASM, A38, pg. 7, 1985.

134. Matthews, J. L., Newman, J. T., Songandares-Bernal, F., Judy, M. M., Skiles, H., Leveson, J. E., Marengo-Rowe, A., J., and Chanh, T. C. Transfusion, 28:81, 1988.

135. Skiles, H. F., Sogandares-Bernal, F., Judy, M. M., Matthews, J. L. and Newman, J. T. Biomedical Engineering VI: Recent developments. Sixth Southern Biomedical Engineering Conference, 1987.

136. For an historical overview see: Budinger, T. F.; Lauterbur, P. C. Science 1984, 226, 288.

137. Morris, P. G. Nuclear Magnetic Resonance Imaging in Medicine and Biology, Claredon Press: Oxford; 1986.

138. For a review of biological applications of NMR see: MacKenzie, N. E.; Gooley, P. R. Med. Res. Rev. 1988, 8, 57.

139. For an introductory discussion of MRI contrast agents see: Tweedle, M. F.; Brittain, H. G.; Eckelman, W. C.; Gaughan, G. T.; Hagan, J. J.; Wedeking, P. W.; Runge, V. M. in Magnetic Resonance Imaging, 2nd ed., Partain, C. L., et al. Eds.; W. B. Saunders: Philadelphia; 1988, Vol. I, pp. 793–809.

140. For a comprehensive review of paramagnetic MRI contrast agents see: Lauffer, R. B. Chem. Rev. 1987, 87, 901.

141. Bloch, F. Phys. Rev. 1946, 70, 460.

142. (a) Bloembergen, N; Purcell, E. M.; Pound, E. V. Phys. Rev. 1948, 73, 679. (b) Solomon, I. Phys. Rev. 1955, 99, 559.

143. (a) Koenig, S. H.; Brown, R. D. III Magn. Res. Med. 1984, I, 437. (b) Koenig, S. H.; Brown, R. D. III Magn. Res. Med. 1984, 1, 478. (c) Koenig, S. H.; Brown, R. D. III Magn. Res. Med. 1985, 2, 159.

144. Tweedle, M. F.; Gaughan, G. T.; Hagan, J; Wedeking, P. W.; Sibley, P.; Wilson, L. J.; Lee, D. W. Nucl. Med. Biol. 1988, 15, 31.

145. Burton, D. R.; Forsen S.; Karlstrom, G; Dwek, R. A. Prog. NMR Sprectr. 1979, 13, 1.

146. Carr, F. H.; Brown, J; Bydder, G. M.; et al. Lancet 1984, 1, 484.

147. (a) Weinmann, H.-J.; Brasch, R. C.; Press, W. R.; Wesby, G. Am. J. Roentg. 1984, 142, 619. (b) Brasch, R. C.; Weinmann, H.-J.; Wesbey, G. E. Am J. Roentg. 1984, 145, 655.

148. (a) Runge, V. M.; Schoerner, W.; Niendorf, H. P.; et al. Mag. Res. Imaging 1985, 3, 27. (b) Runge, V. M.; Price, A. C.; Alleng, James, A. E. Radiology, 1985, 157(P), 37.

149. Koenig, S. H.; Spiller, M.; Brown, R. D. III; Wolf, G. L. Invest. Radiology 1986, 21, 697.

150. Johnston, D. L.; Lieu, P.; Lauffer, R. B.; Newell, J. B.; Wedeen, V. J.; Rosen, B. R.; Brady, T. J.; Okada, R. D. J. Nucl. Med. 1987, 28, 871.

151. Schmiedl, U.; Ogan, M.; paajanen, H.; Marotti, M. Crooks, L. E.; Brito, A. C.; Brasch, R. C. Radiology 1987, 162, 205.

152. Kornguth, S. E.; Turski, P. A.; Perman, W. H.; Schultz, R.; Kalinke, T.; Reale, R.; Raybaud, F. J. Neurosug. 1987, 66, 898.

153. (a) Lauffer, R. B.; Brady, T. J. Magn. Reson. Imaging 1985, 3, 11. (b) Lauffer, R. B.; Brady, T. J.; Brown, R. D.; Baglin, C.; Koenig, S. H. Magn. Reson. Med. 1986, 3, 541.

154. Southwood-Jones, R. V.; Earl, W. L.; Newman, K. E.; Merbach, A. E. J. Chem. Phys. 1980, 73, 5909.

155. Martell, A. E.; Smith, R. M. Critical Stability Constants. Plenum: New York; 1974, Vol. 4.

156. Cacheris, W. P.; Nickle, S. K.; Sherry, A. D. Inorg. Chem 1987, 26, 958.

157. Desreaux, J. F.; Loncin, M. F.; Spirlet, M. R. Inorg. Chim. Acta 1984, 94, 43.

158. Chu, S. C.; Pike, M. M., Fossel, E. T.; Smith, T. W.; Balschi, J. A.; Springer, C. S., Jr. J. Man. Reson. 1984, 56, 33.

159. (a) Spirlet, M.-R.; Rebizant, J.; Desreaux, J. F.; Loncin, M. F. Inorg. Chem. 1984, 23, 359. (b) Spirlet, M.-R.; Rebizant, J.; Loncin, M. F.; Desreaux, J. F. Inorg. Chem. 1984, 23, 4278.

160. Loncin, M. F.; Desreaux, J. F.; Merciny, E.; Inorg. Chem. 1986, 25, 2646.

161. (a) Chang, C. A.; Rowland, M. E. Inorg. Chem. 1983, 22, 3866. (b) Chang, C. A.; Ochaya, V. O. Inorg. Chem. 1986, 25, 355. (c) Chang, C. A.; Sekhar, V. C. Inorg. Chem. 1987, 26, 1981.

162. Geraldes, C. F. G. C.; Sherry, A. D.; Brown, R. D., III; Koenig, S. H.; Magn. Reson. Med. 1986, 3, 242.

163. Lauffer, R. B.; Greif, W. L.; Stark, D. D.; Vincent, A. C.; Saini, S.; Wedeen, V. J.; Brady, T. J. J. Comput. Assist. Tomogr. 1985, 9, 431.

164. Lauffer, R. B.; Vincent, A. C.; Padmanabhan, S.; Meade, T. J. J. Am. Chem. Soc. 1987, 109, 2216.

165. (a) Chen, C.; Cohen, J. S.; Myers, C. E.; Sohn, M. FEBS Lett. 1984, 168, 70. (b) Patronas, N.J.; Cohen, J. S.; Knop, R. H.; Dwyer, A. J.; Colcher, D.; Lundy, J.; Mornex, F.; Hambright, P. Cancer Treat. Rep. 1986, 70, 391. (c) Lyon, R. C.; Faustino, P. J.; Cohen, J. S.; Katz, A.; Mornex, F.; Colcher, D.; Baglin, C.; Koenig, S. H.; Hambright, P. Magn. Reson. Med. 1987, 4, 24. (d) Megnin, F.; Faustino, P. J.; Lyon, R. C.; Lelkes, P. I.; Cohen, J. S. Biochim. Biophys. Acta 1987, 929, 173.

166. Jackson, L. S.; Nelson, J. A.; Case, T. A.; Burnham, B. F. Invest. Radiology 1985, 20, 226.

167. Fiel, R. J.; Button, T. M.; Gilani, S.; et al. Magn. Reson. Imaging 1987, 5, 149.

168. Koenig, S. H.; Brown, R. D. III; Spiller, M. Magn. Reson. Med. 1987, 4, 252.

169. Hambright, P.; Adams, C.; Vernon, K. Inorg. Chem. 1988, 27, 1660.

170. Smith, P. H.; Raymond, K. N. Inorg. Chem. 1985, 24, 3469.

171. For examples of lanthanide cryptates see: (a) Gansow, O. A.; Kauser, A. R.; Triplett, K. M.; Weaver, M. J.; Yee, E. L. J. Am. Chem. Soc. 1977, 99, 7087. (b) Yee, E. L.; Gansow, O. A.; Weaver, M. J. J. Am. Chem. Soc. 1980, 102, 2278. (c) Sabbatini, N.; Dellonte, S.; Ciano, M.; Bonazzi, A.; Balzani; V. Chem. Phys. Let. 1984, 107, 212. (d) Sabbatini, N.; Dellont, S.; Blasse, G. Chem. Phys. Lett. 1986, 129, 541. (e) Desreux, J. F.; Barthelemy, P. P. Nucl. Med. Biol. 1988, 15, 9.

172. For examples of lanthanide complexes stablized by conventional Schiff base macrocycles see: (a) Backer-Dirks, J. D. J.; Gray, C. J.; Hart, F. A.; Hursthouse, M. B.; Schoop, B. C. J. Chem. Soc., Chem. Commun. 1979, 774. (b) De Cola, L.; Smailes, D. L.; Vallarino, L. M. Inorg. Chem. 1986, 25, 1729. (c) Sabbatini, N.; De Cola, L.; Vallarino, L. M.; Blasse, G. J. Phys. Chem. 1987, 91, 4681. (d) Abid, K. K.; Fenton, D. E.; Casellato, U.; Vigato, P.; Graziani, R. J. Chem. Soc., Dalton Trans. 1984, 351. (e) Abid, K. K.; Fenton, D. E. Inorg. Chim. Acta 1984, 95, 119–125. (f) Sakamoto, M. Bull Chem. Soc. Jpn. 1987, 60, 1546.

173. Ochai, E.-I. Bioinorganic Chemistry, an Introduction, Allyn and Bacon: Boston; 1977, p. 168(Fe) and p 436 (Mn).

174. For reviews see: (a) Cytochrome P-450: Structure, Mechanism, and Biochemistry, Ortiz de Montellano, P. R., Ed.; Plenum: New York, 1986. (b) Groves, J. T. Adv. Inorg. Biochem. 1979, I, 119.

175. (a) Buchler, J. W. in The Porphyrins, Dolphin, D.Ed., Academic Press: New York; 1978, Vol. 1, Chapter 10. (b) Srivastava, T. S. Bioinorg. Chem. 1978, 8, 61. (c) Horrocks, W. DeW., Jr. J. Am. Chem. Soc. 1978, 100, 4386.

176. (a) Forsberg, J. H. Coord. Chem. Rev. 1973, 10, 195. (b) Bunzli, J.-C.; Wesner, D. Coord. Chem. Rev. 1984, 60, 191.

177. Pressman, D.; Korngold, L. Cancer 1953, 6, 619.

178. Clinical Nuclear Medicine, Matin, P., Ed., Medical Examination: New York; 1981.

179. Radioimmunoimaging and Radioimmunotherapy, Burchiel, S. W. and Rhodes, B. A., Eds., Elsevier: New York; 1983.

180. Nuclear Imaging in Oncology, Kim, E. E.; Hayhie, T. P., Eds., Appleton-Century-Crofts: Norwalk, Conn.; 1984.

181. Chevru, L. R.; Nunn, A. D.; Loberg, M. D. Semin. Nucl. Med. 1984, 12, 5.

182. Order, S. E. Compr. Therapy 1984, 10, 9.

183. Spencer, R. P. Nuclear Medicine, Medical Examination: New York; 1984.

184. Radiopharmaceuticals and Labelled Compounds 1984 (proceedings of a 1984 conference of the same name), International Atomic Energy Agency: Vienna, 1985.

185. DeLand, F. H.; Goldenberg, D. M. Semin. Nucl. Med. 1985, 15, 2.

186. Radiopharmaceuticals: Progress and Clinical Perspectives, Fritzberg, A. R., Ed., CRC Press: Boca Raton, Fla.; 1986.

187. Goldenberg, D. M.; Goldenberg, H.; Primus, F. J. in Immunoconjugates: Antibody Conjugates in Radioimaging and Therapy of Cancer, Vogel, C.-W., Ed., Oxford University Press: Oxford; 1987, pp. 259–280.

188. Eckelman, W. C.; Paik, C. H.; Reba, R. C. Cancer Res. 1980, 40, 3036.

189. Cole, W. C.; DeNardo, S. J.; Meares, C. F.; McCall, M. J.; DeNardo, G. L.; Epstein, A. L.; O'brien, H. A.; Moi, M. K. J. Nucl. Med. 1987, 28, 83.

190. Deshpande, S. V.; DeNardo, S. J.; Meares, C. F.; McCall, M. J.; Adams, G. P.; Moi, M. K.; DeNardo, G. L. J. Nucl. Med. 1988, 29, 217.

191. Mercer-Smith, J. A.; Roberts, J. C.; Figard, S. D.; Lavallee, D. K. in Antibody-Mediated Delivery Systems, Rodwell, J. D. Ed., Marcel Dekker: New York; 1988, pp. 317–352.

192. (a) O'Brien, H. A., Jr. in reference 119, pp. 161–169. (b) Wessels, B. W.; Rogus, R. D. Med. Phys. 1984, 11, 638. (c) Jungerman, J. A.; Yu, K.-H. P.; Zanelli, C. I. Int. J. Appl. Radiat. Isot. 1984, 9, 883. (d) Humm, J. L. J. Nucl. Med. 1986, 27, 1490.

193. See for instance: (a) Primus, F. J.; DeLand, F. H.; Goldenberg, D. M. in Monoclonal Antibodies and Cancer, "Wright, G. L. Ed., Marcel Dekker: New York; 1984, pp. 305–323. (b) Weinstein, J. N.; Black, C. D. V.; Keenan, A. M.; Holten, O. D., III; Larson, S. M.; Sieber, S. M.; Covell, D. G.; Carrasquillo, J.; Barbet, J.; Parker, R. J. in "Monoclonal Antibodies and Cancer Therapy," Reisfeld, R. A. and Sell, S., Eds., Alan R. Liss: New York; 1985, pp. 473–488.

194. Burns, H. D.; Worley, P.; Wagner, H. N., Jr.; Marzilli, L.; Risch, V. in The Chemistry of Radiopharmaceuticals, Heindel, N. D.; Burns, H. D.; Honda, T.; Brady, L. W., Eds., Masson: New York; 1978.

195. Paik, C. H., Ebbert, M. A.; Murphy, P. R.; Lassman, C. R.; Reba, R. C.; Eckelman, W. C.; Pak, K. Y.; Powe, J.; Steplewski, Z.; Koprowski, H. J. Nucl. Med. 1983, 24, 1158.

196. See for instance: Hnatowich, D. J.; Childs, R. L.; Lanteigne, D.; Najafi, A. J. Immunol. Meth. 1983, 65, 147.

197. See for instance: Hnatowich, D. J.; Virzi, F.; Doherty, P. W. J. Nucl. Med. 1985, 26, 503.

198. Katagi, T.; Yamamura, T.; Saito, T.; Sasaki, Y. Chem. Lett. 1981, 503.

199. Sessler, J. L.; Johnson, M. R.; Lynch, V. J. Org. Chem. 1987, 52, 4394.

200. Niclas, H. J.; Bohle, M.; Rick, J.-D.; Zeuner, F.; Zolch, L. Z. Chem. 1985, 25, 137.

201. Beilstein 4th ed., Band 14, p. 785.

202. (a) Paul, R.; Anderson, G. W. J. Am. Chem. Soc. 1960, 82, 4596. (b) Davis, M.-T. B.; Preston, J. F. Anal. Biochem. 1981, 116, 402. (c) Anderson, G. W.; Zimmerman, J. E; Callahan, F. M. J. Am. Chem. Soc. 1964, 86, 1839.

203. Vollhardt, K. P. C. Synthesis 1985, 765.

204. Kati, H. A.; Siddappa, S. Indian J. Chem. 1983, 22B, 1205.

205. Hove, E.; Horrocks, W. D. J. Am. Chem. Soc. 1978, 100, 4386.

206. Furhop, J.-H.; Smith, K. M. in Porphyrins and Metalloporphyrins, Smith, K. M., Ed., Elsevier: Amsterdam; 1975.

207. Kyba et al., J. Am. Chem. Soc. 1981, 103:3868–3875.

What is claimed is:

1. A method of treating a host harboring neoplastic tissue, the method comprising:

administering to the host an effective amount of a water-soluble texaphyrin-diamagnetic metal complex; and photoirradiating the texaphyrin-diamagnetic metal complex in proximity to the neoplastic tissue.

2. A method of treating a host harboring neoplastic tissue, the method comprising:

administering to the host an effective amount of a water-soluble texaphyrin having the following structure:

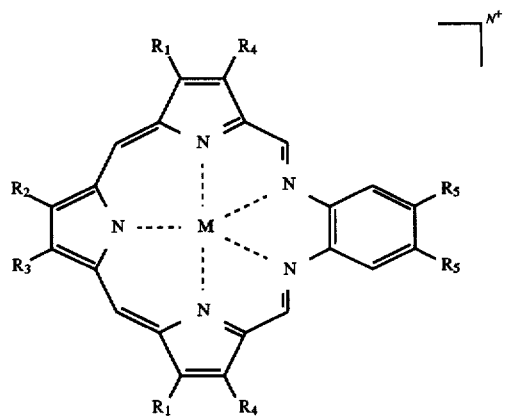

wherein,

M is a diamagnetic metal cation;

$R_1$, $R_2$, $R_3$, $R_4$ and $R_5$ are independently hydrogen, hydroxyl, alkyl, hydroxyalkyl, oxyalkyl, oxyhydroxyalkyl, saccharide, carboxyalkyl or carboxyamidealkyl where at least one of $R_1$, $R_2$, $R_3$, $R_4$ and $R_5$ is hydroxyl, hydroxyalkyl, oxyalkyl, oxyhydroxyalkyl, saccharide, carboxyalkyl or carboxyamidealkyl; and N is an integer less than or equal to 2; and photoirradiating the texaphyrin in proximity to the neoplastic tissue.

3. A method of treating a host harboring neoplastic tissue, the method comprising:

administering to the host an effective amount of a texaphyrin having the following structure:

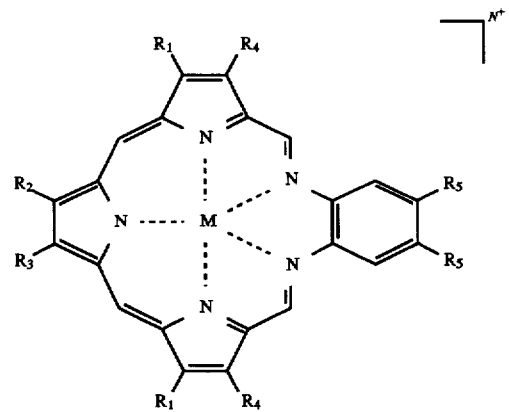

wherein,

M is a diamagnetic metal cation; $R_1$ is $CH_2CH_3$ or $(CH_2)_2CH_2OH$; $R_5$ is $O(CH_2)_2CH_2OH$ or $O(CH_2CH_2O)_2CH_2CH_2OR'$, where R' is H or $CH_3$; and N is an integer less than or equal to 2; and photoirradiating the texaphyrin in proximity to the neoplastic tissue.

4. The method according to claim 1 wherein the texaphyrin has the structure:

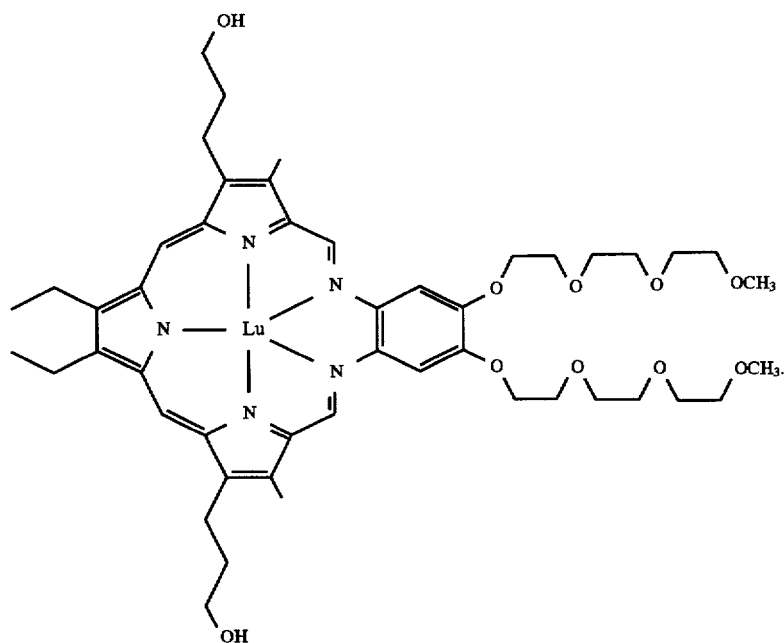

5. The method according to claim 1 wherein the texaphyrin has the structure:

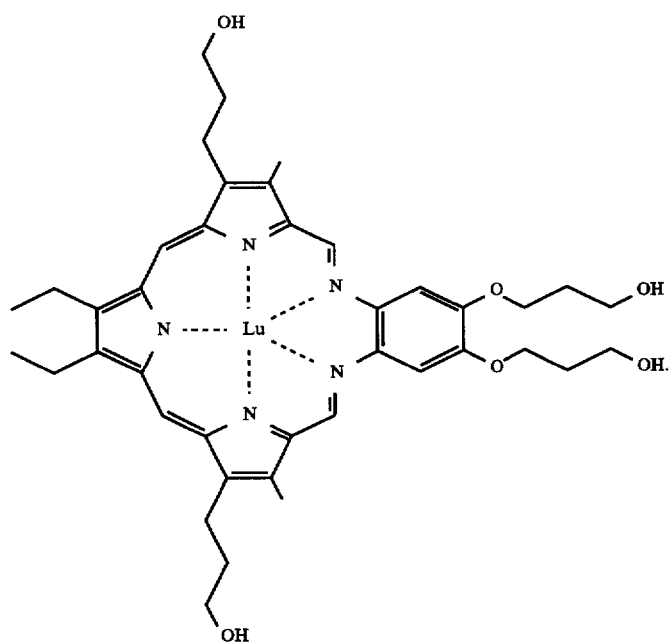

6. The method according to claim 1 wherein the neoplastic tissue is benign neoplastic tissue.

7. The method according to claim 2 wherein the neoplastic tissue is benign neoplastic tissue.

8. The method according to claim 3 wherein the neoplastic tissue is benign neoplastic tissue.

9. The method according to claim 4 wherein the neoplastic tissue is benign neoplastic tissue.

10. The method according to claim 5 wherein the neoplastic tissue is benign neoplastic tissue.

11. The method according to claim 1 wherein the neoplastic tissue malignant.

12. The method according to claim 2 wherein the neoplastic tissue is malignant.

13. The method according to claim 3 wherein the neoplastic tissue is malignant.

14. The method according to claim 4 wherein the neoplastic tissue is malignant.

15. The method according to claim 5 wherein the neoplastic tissue is malignant.

16. The method according to claim 2 wherein the diamagnetic metal cation is selected from the group consisting of In(III), Y(III), La(III) and Lu(III).

17. The method according to claim 3 wherein the diamagnetic metal cation is selected from the group consisting of In(III), Y(III), La(III) and Lu(III).

18. The method according to claim 1 wherein the photoirradiating is at a wavelength of about 700 to 770 nanometers.

19. The method according to claim 2 wherein the photoirradiating is at a wavelength of about 700 to 770 nanometers.

* * * * *

UNITED STATES PATENT AND TRADEMARK OFFICE
CERTIFICATE OF CORRECTION

PATENT NO. : 5,733,903
DATED : March 31, 1998
INVENTOR(S) : Sessler, et al.

It is certified that error appears in the above-identified patent and that said Letters Patent is hereby corrected as shown below:

On the cover page, item [ 54 ] and at column 1, line 2 (the Title) please change "TEXAPHYRINE" to --TEXAPHYRIN--.

At column 1, please replace the paragraph at lines 14-15 with the following:

--   The government may own certain rights in the present invention pursuant to one or more of the following: National Institutes of Health Grants CA68682, AI28845 and AI33577; and National Science Foundation Grants CHE8552768 and CHE9122161.--

Signed and Sealed this

Sixth Day of June, 2000

Attest:

Q. TODD DICKINSON

*Attesting Officer*          *Director of Patents and Trademarks*